(12) United States Patent
Nappa et al.

(10) Patent No.: US 8,012,368 B2
(45) Date of Patent: *Sep. 6, 2011

(54) COMPOSITIONS COMPRISING FLUOROOLEFINS AND USES THEREOF

(75) Inventors: Mario Joseph Nappa, Newark, DE (US); Barbara Haviland Minor, Elkton, MD (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/696,839

(22) Filed: Jan. 29, 2010

(65) Prior Publication Data

US 2010/0132387 A1 Jun. 3, 2010

Related U.S. Application Data

(62) Division of application No. 11/589,588, filed on Oct. 30, 2006, now Pat. No. 7,708,903.

(60) Provisional application No. 60/732,581, filed on Nov. 1, 2005.

(51) Int. Cl.
*C09K 5/04* (2006.01)

(52) U.S. Cl. ........................................ 252/67

(58) Field of Classification Search .................. 252/67, 252/68
See application file for complete search history.

(56) References Cited

U.S. PATENT DOCUMENTS

| | | | |
|---|---|---|---|
| 2,931,840 A | 4/1960 | Marquis |
| 2,996,555 A | 8/1961 | Rausch |
| 3,723,318 A | 3/1973 | Butler |
| 3,884,828 A | 5/1975 | Butler |
| 4,788,352 A | 11/1988 | Smutny |
| 5,037,573 A | 8/1991 | Merchant |
| 5,254,280 A | 10/1993 | Thomas et al. |
| 5,421,192 A | 6/1995 | Henry |
| 5,516,946 A | 5/1996 | Jackson et al. |
| 5,532,419 A | 7/1996 | Van Der Puy et al. |
| 5,616,275 A | 4/1997 | Chisolm et al. |
| 5,679,875 A | 10/1997 | Aoyama et al. |
| 5,714,655 A | 2/1998 | Yamamoto et al. |
| 5,736,063 A | 4/1998 | Richard et al. |
| 5,744,052 A | 4/1998 | Bivens |
| 5,788,886 A | 8/1998 | Minor et al. |
| 5,969,198 A | 10/1999 | Thenappan et al. |
| 6,053,008 A | 4/2000 | Arman et al. |
| 6,065,305 A | 5/2000 | Arman et al. |
| 6,076,372 A | 6/2000 | Acharya et al. |
| 6,111,150 A | 8/2000 | Sakyu et al. |
| 6,176,102 B1 | 1/2001 | Novak et al. |
| 6,258,292 B1 | 7/2001 | Turner |
| 6,300,378 B1 | 10/2001 | Tapscott |
| 6,426,019 B1 | 7/2002 | Acharya et al. |
| 6,858,571 B2 | 2/2005 | Pham et al. |
| 6,969,701 B2 | 11/2005 | Singh et al. |
| 2003/0042463 A1 | 3/2003 | Arman et al. |
| 2003/0209685 A1 | 11/2003 | Robin et al. |
| 2004/0089839 A1 | 5/2004 | Thomas et al. |
| 2004/0119047 A1 | 6/2004 | Singh et al. |
| 2004/0127383 A1 | 7/2004 | Pham et al. |
| 2004/0256594 A1 | 12/2004 | Singh et al. |
| 2005/0077501 A1 | 4/2005 | Pham et al. |
| 2005/0090698 A1 | 4/2005 | Merkel et al. |
| 2005/0233923 A1 | 10/2005 | Singh et al. |
| 2005/0233931 A1 | 10/2005 | Singh et al. |
| 2005/0233932 A1 | 10/2005 | Singh et al. |
| 2005/0233933 A1 | 10/2005 | Singh et al. |
| 2005/0233934 A1 | 10/2005 | Singh et al. |
| 2005/0241805 A1 | 11/2005 | Singh et al. |
| 2005/0245421 A1 | 11/2005 | Singh et al. |
| 2005/0247905 A1 | 11/2005 | Singh et al. |
| 2006/0010872 A1 | 1/2006 | Singh et al. |
| 2006/0022166 A1 | 2/2006 | Wilson et al. |
| 2006/0025322 A1 | 2/2006 | Wilson et al. |
| 2006/0043330 A1 | 3/2006 | Wilson et al. |
| 2006/0043331 A1 | 3/2006 | Shankland et al. |
| 2010/0127208 A1 | 5/2010 | Nappa et al. |

FOREIGN PATENT DOCUMENTS

| | | |
|---|---|---|
| CN | 1083474 C | 4/2004 |
| EP | 0 670 295 A1 | 9/1995 |
| EP | 1 016 839 A2 | 7/2000 |
| EP | 1 191 080 A2 | 3/2002 |
| EP | 1 686 111 A1 | 8/2006 |
| JP | 4-110388 A | 4/1992 |
| JP | 1993085970 A | 4/1993 |
| RU | 2073058 C1 | 2/1997 |
| WO | 93/16023 A1 | 8/1993 |
| WO | 2004/037752 A2 | 5/2004 |
| WO | 2004/037913 A2 | 5/2004 |
| WO | 2004/037552 A1 | 6/2004 |
| WO | 2005/042663 A1 | 5/2005 |
| WO | 2005/049761 A1 | 6/2005 |
| WO | 2005/083027 A1 | 9/2005 |

OTHER PUBLICATIONS

Office Action mailed Mar. 16, 2010, in co-pending U.S. Appl. No. 12/696,793.
Office Action mailed Jun. 29, 2010, in co-pending U.S. Appl. No. 12/696,793.
Office Action mailed Dec. 6, 2010, in co-pending U.S. Appl. No. 12/696,793. Chemical Abstracts, vol. 119, No. 10, Sep. 6, 1993, Columbus, Ohio, US; abstract No. 98469, Fujiwara et. al. "2-trifluoromethyl-3,3,3-trifluoropropene" XP002431016.
Derwent Abstract XP-002343594: JP 4-110388, Apr. 1992.
English Translation—Claims: CN 1083474C, Apr. 2004.
Grzyll, L. R., et al., "Development of Nontoxic Heat Transport Fluids for Habitat Two-Phase Thermal Control Systems", Energy Conversion Engineering Conference, 1996. IECEC 96., Proceedings of the 31st Intersociety Washington, DC; Aug. 11-16, 1996, New York, NY; IEEE vol. 2, pp. 1506-1511 (Aug. 11, 2006).
Haszeldine, R. N., et al., "Free-Radical Additions to Unsaturated Systems. Part SVII. Reaction of Trifluoroiodomethane with Mixtures of Ethylene and Vinyl Fluoride and of Ethylene and Propene", Chemistry Department, University of Manchester Institute of Science and Technology, Manchester M60 1QD, J. Chem. Soc. (C), 1970, pp. 414-421.

(Continued)

*Primary Examiner* — John R Hardee

(57) ABSTRACT

The present invention relates to fluoroolefin compositions. The fluoroolefin compositions of the present invention are useful as refrigerants or heat transfer fluids and in processes for producing cooling or heat. Additionally, the fluoroolefin compositions of the present invention may be used to replace currently used refrigerant or heat transfer fluid compositions that have higher global warming potential.

11 Claims, No Drawings

OTHER PUBLICATIONS

Henne, A. L., et al., "Fluorinated Derivatives of Propane and Propylene", Department of Chemistry, The Ohio State University, vol. 68, pp. 496-497 (Mar. 1946).

International Search Report (Date of Mailing: May 14, 2007).

Knunyants, I. L., et al., "Reactions of Fluoro Olefins, Communication 13. Catalytic Hydrogenation of Perfluoro Olefins", Institute of Heteroorganic Compounds, Academy of Sciences of the USSR, Otdelenie Khimicheskikh Nauk, No. 8, pp. 1312-1317, (Aug. 1960).

Tarrant, P., et al., "Free Radical Additions Involving Fluorine Compounds. IV. The Addition of Dibromodifluoromethane to Some Fluoroolefins", Department of Chemistry, University of Florida, pp. 2783-2787 (May 20, 1955).

Vineyard, E. A., et al., "Selection of Ozone-Safe, Nonazeotropic Refrigerant Mixtures for Capacity Modulation in Residential Heat Pumps", ASHRAE Transactions, Technical and Symposium Papers, Chicago Technical Program, vol. 95, Part 1, pp. 34-46 (Jan. 29, 1989).

Written Opinion of the International Searching Authority (Date of Mailing: May 14, 2007).

COMPOSITIONS COMPRISING FLUOROOLEFINS AND USES THEREOF

CROSS REFERENCE(S) TO RELATED APPLICATION(S)

This application is a divisional application of and claims the priority benefit of U.S. patent application Ser. No. 11/589,588, filed Oct. 30, 2006, now U.S. Pat. No. 7,708,903, which claims the priority benefit of U.S. Provisional Application 60/732,581, filed Nov. 1, 2005.

FIELD OF THE INVENTION

The present invention relates to compositions for use in refrigeration, air-conditioning or heat pump systems wherein the composition comprises at least one fluoroolefin. The compositions of the present invention are useful in processes for producing refrigeration or heat, as heat transfer fluids and many other uses.

BACKGROUND OF THE INVENTION

The refrigeration industry has been working for the past few decades to find replacement refrigerants for the ozone depleting chlorofluorocarbons (CFCs) and hydrochlorofluorocarbons (HCFCs) being phased out as a result of the Montreal Protocol. The solution for most refrigerant producers has been the commercialization of hydrofluorocarbon (HFC) refrigerants. The new HFC refrigerants, HFC-134a being the most widely used at this time, have zero ozone depletion potential and thus are not affected by the current regulatory phase out as a result of the Montreal Protocol.

Further environmental regulations may ultimately cause global phase out of certain HFC refrigerants. Currently, the automobile industry is facing regulations relating to global warming potential for refrigerants used in mobile air-conditioning. Therefore, there is a great current need to identify new refrigerants with reduced global warming potential for the mobile air-conditioning market. Should the regulations be more broadly applied in the future, an even greater need will be felt for refrigerants that can be used in all areas of the refrigeration and air-conditioning industry.

Currently proposed replacement refrigerants for HFC-134a include HFC-152a, pure hydrocarbons such as butane or propane, or "natural" refrigerants such as $CO_2$. Many of these suggested replacements are toxic, flammable, and/or have low energy efficiency. Therefore, new alternative refrigerants are being sought.

The object of the present invention is to provide novel refrigerant compositions and heat transfer fluid compositions that provide unique characteristics to meet the demands of low or zero ozone depletion potential and lower global warming potential as compared to current refrigerants.

BRIEF SUMMARY OF THE INVENTION

The present invention relates to a refrigerant or heat transfer fluid composition comprising at least one compound selected from the group consisting of:
(i) fluoroolefins of the formula E- or $Z-R^1CH=CHR^2$, wherein $R^1$ and $R^2$ are, independently, $C_1$ to $C_6$ perfluoroalkyl groups, and wherein the total number of carbons in the compound is at least 5;
(ii) cyclic fluoroolefins of the formula cyclo-$[CX=CY(CZW)_n-]$, wherein X, Y, Z, and W, independently, are H or F, and n is an integer from 2 to 5; and
(iii) fluoroolefins selected from the group consisting of: 2,3,3-trifluoro-1-propene ($CHF_2CF=CH_2$); 1,1,2-trifluoro-1-propene ($CH_3CF=CF_2$); 1,2,3-trifluoro-1-propene ($CH_2FCF=CF_2$); 1,1,3-trifluoro-1-propene ($CH_2FCH=CF_2$); 1,3,3-trifluoro-1-propene ($CHF_2CH=CHF$); 1,1,1,2,3,4,4,4-octafluoro-2-butene ($CF_3CF=CFCF_3$); 1,1,2,3,3,4,4,4-octafluoro-1-butene ($CF_3CF_2CF=CF_2$); 1,1,1,2,4,4,4-heptafluoro-2-butene ($CF_3CF=CHCF_3$); 1,2,3,3,4,4,4-heptafluoro-1-butene ($CHF=CFCF_2CF_3$); 1,1,1,2,3,4,4-heptafluoro-2-butene ($CHF_2CF=CFCF_3$); 1,3,3,3-tetrafluoro-2-(trifluoromethyl)-1-propene (($CF_3)_2C=CHF$); 1,1,3,3,4,4,4-heptafluoro-1-butene ($CF_2=CHCF_2CF_3$); 1,1,2,3,4,4,4-heptafluoro-1-butene ($CF_2=CFCHFCF_3$); 1,1,2,3,3,4,4-heptafluoro-1-butene ($CF_2=CFCF_2CHF_2$); 2,3,3,4,4,4-hexafluoro-1-butene ($CF_3CF_2CF=CH_2$); 1,3,3,4,4,4-hexafluoro-1-butene ($CHF=CHCF_2CF_3$); 1,2,3,4,4,4-hexafluoro-1-butene ($CHF=CFCHFCF_3$); 1,2,3,3,4,4-hexafluoro-1-butene ($CHF=CFCF_2CHF_2$); 1,1,2,3,4,4-hexafluoro-2-butene ($CHF_2CF=CFCHF_2$); 1,1,1,2,3,4-hexafluoro-2-butene ($CH_2FCF=CFCF_3$); 1,1,1,2,4,4-hexafluoro-2-butene ($CHF_2CH=CFCF_3$); 1,1,3,4,4,4-hexafluoro-2-butene ($CF_3CH=CFCHF_2$); 1,1,2,3,3,4-hexafluoro-1-butene ($CF_2=CFCF_2CH_2F$); 1,1,2,3,4,4-hexafluoro-1-butene ($CF_2=CFCHFCHF_2$); 3,3,3-trifluoro-2-(trifluoromethyl)-1-propene ($CH_2=C(CF_3)_2$); 1,1,1,2,4-pentafluoro-2-butene ($CH_2FCH=CFCF_3$); 1,1,1,3,4-pentafluoro-2-butene ($CF_3CH=CFCH_2F$); 3,3,4,4,4-pentafluoro-1-butene ($CF_3CF_2CH=CH_2$); 1,1,1,4,4-pentafluoro-2-butene ($CHF_2CH=CHCF_3$); 1,1,1,2,3-pentafluoro-2-butene ($CH_3CF=CFCF_3$); 2,3,3,4,4-pentafluoro-1-butene ($CH_2=CFCF_2CHF_2$); 1,1,2,4,4-pentafluoro-2-butene ($CHF_2CF=CHCHF_2$); 1,1,2,3,3-pentafluoro-1-butene ($CH_3CF_2CF=CF_2$); 1,1,2,3,4-pentafluoro-2-butene ($CH_2FCF=CFCHF_2$); 1,1,3,3,3-pentafluoro-2-methyl-1-propene ($CF_2=C(CF_3)(CH_3)$); 2-(difluoromethyl)-3,3,3-trifluoro-1-propene ($CH_2=C(CHF_2)(CF_3)$); 2,3,4,4,4-pentafluoro-1-butene ($CH_2=CFCHFCF_3$); 1,2,4,4,4-pentafluoro-1-butene ($CHF=CFCH_2CF_3$); 1,3,4,4,4-pentafluoro-1-butene ($CHF=CHCHFCF_3$); 1,3,3,4,4-pentafluoro-1-butene ($CHF=CHCF_2CHF_2$); 1,2,3,4,4-pentafluoro-1-butene ($CHF=CFCHFCHF_2$); 3,3,4,4-tetrafluoro-1-butene ($CH_2=CHCF_2CHF_2$); 1,1-difluoro-2-(difluoromethyl)-1-propene ($CF_2=C(CHF_2)(CH_3)$); 1,3,3,3-tetrafluoro-2-methyl-1-propene ($CHF=C(CF_3)(CH_3)$); 3,3-difluoro-2-(difluoromethyl)-1-propene ($CH_2=C(CHF_2)_2$); 1,1,1,2-tetrafluoro-2-butene ($CF_3CF=CHCH_3$); 1,1,1,3-tetrafluoro-2-butene ($CH_3CF=CHCF_3$); 1,1,1,2,3,4,4,5,5,5-decafluoro-2-pentene ($CF_3CF=CFCF_2CF_3$); 1,1,2,3,3,4,4,5,5,5-decafluoro-1-pentene ($CF_2=CFCF_2CF_2CF_3$); 1,1,1,4,4,4-hexafluoro-2-(trifluoromethyl)-2-butene (($CF_3)_2C=CHCF_3$); 1,1,1,2,4,4,5,5,5-nonafluoro-2-pentene ($CF_3CF=CHCF_2CF_3$); 1,1,1,3,4,4,5,5,5-nonafluoro-2-pentene ($CF_3CH=CFCF_2CF_3$); 1,2,3,3,4,4,5,5,5-nonafluoro-1-pentene ($CHF=CFCF_2CF_2CF_3$); 1,1,3,3,4,4,5,5,5-nonafluoro-1-pentene ($CF_2=CHCF_2CF_2CF_3$); 1,1,2,3,3,4,4,5,5-nonafluoro-1-pentene ($CF_2=CFCF_2CF_2CHF_2$); 1,1,2,3,4,4,5,5,5-nonafluoro-2-pentene ($CHF_2CF=CFCF_2CF_3$); 1,1,1,2,3,4,4,5,5-nonafluoro-2-pentene ($CF_3CF=CFCF_2CHF_2$); 1,1,1,2,3,4,5,5,5-nonafluoro-2-pentene ($CF_3CF=CFCHFCF_3$); 1,2,3,4,4,4-hexafluoro-3-(trifluoromethyl)-1-butene ($CHF=CFCF(CF_3)_2$); 1,1,2,4,4,4-hexafluoro-3-(trifluoromethyl)-1-butene ($CF_2$=$CFCH(CF_3)_2$); 1,1,1,4,4,4-hexafluoro-2-(trifluoromethyl)-2-butene ($CF_3CH$=$C(CF_3)_2$); 1,1,3,4,4,4-hexafluoro-3-(trifluoromethyl)-1-butene ($CF_2$=$CHCF(CF_3)_2$); 2,3,3,4,4,5,5,5-octafluoro-1-pentene ($CH_2$=$CFCF_2CF_2CF_3$); 1,2,3,3,4,4,5,5-octafluoro-1-pentene ($CHF$=$CFCF_2CF_2CHF_2$); 3,3,4,4-pentafluoro-2-(trifluoromethyl)-1-butene ($CH_2$=$C(CF_3)CF_2CF_3$); 1,1,4,4,4-pentafluoro-3-(trifluoromethyl)-1-butene ($CF_2$=$CHCH(CF_3)_2$); 1,3,4,4,4-pentafluoro-3-(trifluoromethyl)-1-butene ($CHF$=$CHCF(CF_3)_2$); 1,1,4,4,4-pentafluoro-2-(trifluoromethyl)-1-butene ($CF_2$=$C(CF_3)CH_2CF_3$); 3,4,4,4-tetrafluoro-3-(trifluoromethyl)-1-butene (($CF_3)_2CFCH$=$CH_2$); 3,3,4,4,5,5,5-heptafluoro-1-pentene ($CF_3CF_2CF_2CH$=$CH_2$); 2,3,3,4,4,5,5-heptafluoro-1-pentene ($CH_2$=$CFCF_2CF_2CHF_2$); 1,1,3,3,5,5,5-heptafluoro-1-butene ($CF_2$=$CHCF_2CH_2CF_3$); 1,1,1,2,4,4,4-heptafluoro-3-methyl-2-butene ($CF_3CF$=$C(CF_3)(CH_3)$); 2,4,4,4-tetrafluoro-3-(trifluoromethyl)-1-butene ($CH_2$=$CFCH(CF_3)_2$); 1,4,4,4-tetrafluoro-3-(trifluoromethyl)-1-butene ($CHF$=$CHCH(CF_3)_2$); 1,1,1,4-tetrafluoro-2-(trifluoromethyl)-2-butene ($CH_2FCH$=$C(CF_3)_2$); 1,1,1,3-tetrafluoro-2-(trifluoromethyl)-2-butene ($CH_3CF$=$C(CF_3)_2$); 1,1,1-trifluoro-2-(trifluoromethyl)-2-butene (($CF_3)_2C$=$CHCH_3$); 3,4,4,5,5,5-hexafluoro-2-pentene ($CF_3CF_2CF$=$CHCH_3$); 1,1,1,4,4,4-hexafluoro-2-methyl-2-butene ($CF_3C(CH_3)$=$CHCF_3$); 3,3,4,5,5,5-hexafluoro-1-pentene ($CH_2$=$CHCF_2CHFCF_3$); 4,4,4-trifluoro-3-(trifluoromethyl)-1-butene ($CH_2$=$C(CF_3)CH_2CF_3$); 1,1,2,3,3,4,4,5,5,6,6,6-dodecafluoro-1-hexene ($CF_3(CF_2)_3CF$=$CF_2$); 1,1,1,2,2,3,4,5,5,6,6,6-dodecafluoro-3-hexene ($CF_3CF_2CF$=$CFCF_2CF_3$); 1,1,1,4,4,4-hexafluoro-2,3-bis(trifluoromethyl)-2-butene (($CF_3)_2C$=$C(CF_3)_2$); 1,1,1,2,3,4,5,5,5-nonafluoro-4-(trifluoromethyl)-2-pentene (($CF_3)_2CFCF$=$CFCF_3$); 1,1,1,4,4,5,5,5-octafluoro-2-(trifluoromethyl)-2-pentene (($CF_3)_2C$=$CHC_2F_5$); 1,1,1,3,4,5,5,5-octafluoro-4-(trifluoromethyl)-2-pentene (($CF_3)_2CFCF$=$CHCF_3$); 3,3,4,4,5,5,6,6,6-nonafluoro-1-hexene ($CF_3CF_2CF_2CF_2CH$=$CH_2$); 4,4,4-trifluoro-3,3-bis(trifluoromethyl)-1-butene ($CH_2$=$CHC(CF_3)_3$); 1,1,1,4,4,4-hexafluoro-2-(trifluoromethyl)-3-methyl-2-butene (($CF_3)_2C$=$C(CH_3)(CF_3)$); 2,3,3,5,5,5-hexafluoro-4-(trifluoromethyl)-1-pentene ($CH_2$=$CFCF_2CH(CF_3)_2$); 1,1,2,4,4,5,5,5-nonafluoro-3-methyl-2-pentene ($CF_3CF$=$C(CH_3)CF_2CF_3$); 1,1,1,5,5,5-hexafluoro-4-(trifluoromethyl)-2-pentene ($CF_3CH$=$CHCH(CF_3)_2$); 3,4,4,5,5,6,6,6-octafluoro-2-hexene ($CF_3CF_2CF_2CF$=$CHCH_3$); 3,3,4,4,5,5,6,6-octafluoro1-hexene ($CH_2$=$CHCF_2CF_2CF_2CHF_2$); 1,1,1,4,4-pentafluoro-2-(trifluoromethyl)-2-pentene (($CF_3)_2C$=$CHCF_2CH_3$); 4,4,5,5,5-pentafluoro-2-(trifluoromethyl)-1-pentene ($CH_2$=$C(CF_3)CH_2C_2F_5$); 3,3,4,4,5,5,5-heptafluoro-2-methyl-1-pentene ($CF_3CF_2CF_2C(CH_3)$=$CH_2$); 4,4,5,5,6,6,6-heptafluoro-2-hexene ($CF_3CF_2CF_2CH$=$CHCH_3$); 4,4,5,5,6,6,6-heptafluoro-1-hexene ($CH_2$=$CHCH_2CF_2C_2F_5$); 1,1,1,2,2,3,4-heptafluoro-3-hexene ($CF_3CF_2CF$=$CFC_2H_5$); 4,5,5,5-tetrafluoro-4-(trifluoromethyl)-1-pentene ($CH_2$=$CHCH_2CF(CF_3)_2$); 1,1,1,2,5,5,5-heptafluoro-4-methyl-2-pentene ($CF_3CF$=$CHCH(CF_3)(CH_3)$); 1,1,1,3-tetrafluoro-2-(trifluoromethyl)-2-pentene (($CF_3)_2C$=$CFC_2H_5$); 1,1,1,2,3,4,4,5,5,6,6,7,7,7-tetradecafluoro-2-heptene ($CF_3CF$=$CFCF_2CF_2C_2F_5$); 1,1,1,2,2,3,4,5,5,6,6,7,7,7-tetradecafluoro-3-heptene ($CF_3CF_2CF$=$CFCF_2C_2F_5$); 1,1,1,3,4,4,5,5,6,6,7,7,7-tridecafluoro-2-heptene ($CF_3CH$=$CFCF_2CF_2C_2F_5$); 1,1,1,2,4,4,5,5,6,6,7,7,7-tridecafluoro-2-heptene ($CF_3CF$=$CHCF_2CF_2C_2F_5$); 1,1,1,2,2,4,5,5,6,6,7,7,7-tridecafluoro-3-heptene ($CF_3CF_2CH$=$CFCF_2C_2F_5$); 1,1,1,2,2,3,5,5,6,6,7,7,7-tridecafluoro-3-heptene ($CF_3CF_2CF$=$CHCF_2C_2F_5$); $CF_2$=$CFOCF_2CF_3$ (PEVE) and $CF_2$=$CFOCF_3$ (PMVE).

The present invention further relates to a composition comprising: (i) at least one fluoroolefin compound; and (ii) at least one flammable refrigerant; wherein said fluoroolefin is selected from the group consisting of:

(a) fluoroolefins of the formula E- or Z—$R^1CH$=$CHR^2$, wherein $R^1$ and $R^2$ are, independently, $C_1$ to $C_6$ perfluoroalkyl groups;

(b) cyclic fluoroolefins of the formula cyclo-[$CX$=$CY(CZW)_n$—], wherein X, Y, Z, and W, independently, are H or F, and n is an integer from 2 to 5; and (c) fluoroolefins selected from the group consisting of: 1,2,3,3,3-pentafluoro-1-propene ($CF_3CF$=$CHF$); 1,1,3,3,3-pentafluoro-1-propene ($CF_3CH$=$CF_2$); 1,1,2,3,3-pentafluoro-1-propene ($CHF_2CF$=$CF_2$); 1,1,1,2,3,4,4-octafluoro-2-butene ($CF_3CF$=$CFCF_3$); 1,1,2,3,3,4,4-octafluoro-1-butene ($CF_3CF_2CF$=$CF_2$); 1,1,1,2,4,4,4-heptafluoro-2-butene ($CF_3CF$=$CHCF_3$); 1,2,3,3,4,4-heptafluoro-1-butene ($CHF$=$CFCF_2CF_3$); 1,1,1,2,3,4,4-heptafluoro-2-butene ($CHF_2CF$=$CFCF_3$); 1,3,3,3-tetrafluoro-2-(trifluoromethyl)-1-propene (($CF_3)_2C$=$CHF$); 1,1,3,3,4,4,4-heptafluoro-1-butene ($CF_2$=$CHCF_2CF_3$); 1,1,2,3,4,4,4-heptafluoro-1-butene ($CF_2$=$CFCHFCF_3$); 1,1,2,3,3,4,4-heptafluoro-1-butene ($CF_2$=$CFCF_2CHF_2$); 2,3,3,4,4,4-hexafluoro-1-butene ($CF_3CF_2CF$=$CH_2$); 1,3,3,4,4,4-hexafluoro-1-butene ($CHF$=$CHCF_2CF_3$); 1,2,3,4,4,4-hexafluoro-1-butene ($CHF$=$CFCHFCF_3$); 1,2,3,3,4,4-hexafluoro-1-butene ($CHF$=$CFCF_2CHF_2$); 1,1,2,3,4,4-hexafluoro-2-butene ($CHF_2CF$=$CFCHF_2$); 1,1,1,2,3,4-hexafluoro-2-butene ($CH_2FCF$=$CFCF_3$); 1,1,1,2,4-hexafluoro-2-butene ($CHF_2CH$=$CFCF_3$); 1,1,1,3,4,4-hexafluoro-2-butene ($CF_3CH$=$CFCHF_2$); 1,1,2,3,3,4-hexafluoro-1-butene ($CF_2$=$CFCF_2CH_2F$); 1,1,2,3,4,4-hexafluoro-1-butene ($CF_2$=$CFCHFCHF_2$); 3,3,3-trifluoro-2-(trifluoromethyl)-1-propene ($CH_2$=$C(CF_3)_2$); 1,1,1,2,3,4,4,5,5,5-decafluoro-2-pentene ($CF_3CF$=$CFCF_2CF_3$); 1,1,2,3,3,4,4,5,5,5-decafluoro-1-pentene ($CF_2$=$CFCF_2CF_2CF_3$); 1,1,1,4,4,4-hexafluoro-2-(trifluoromethyl)-2-butene (($CF_3)_2C$=$CHCF_3$); 1,1,1,2,4,4,5,5,5-nonafluoro-2-pentene ($CF_3CF$=$CHCF_2CF_3$); 1,1,1,3,4,4,5,5,5-nonafluoro-2-pentene ($CF_3CH$=$CFCF_2CF_3$); 1,2,3,3,4,4,5,5,5-nonafluoro-1-pentene ($CHF$=$CFCF_2CF_2CF_3$); 1,1,3,3,4,4,5,5,5-nonafluoro-1-pentene ($CF_2$=$CHCF_2CF_2CF_3$); 1,1,2,3,3,4,4,5,5-nonafluoro-1-pentene ($CF_2$=$CFCF_2CF_2CHF_2$); 1,1,2,3,4,4,5,5,5-nonafluoro-2-pentene ($CHF_2CF$=$CFCF_2CF_3$); 1,1,1,2,3,4,4,5,5-nonafluoro-2-pentene ($CF_3CF$=$CFCF_2CHF_2$); 1,1,1,2,3,4,5,5,5-nonafluoro-2-pentene ($CF_3CF$=$CFCHFCF_3$); 1,2,3,4,4,4-hexafluoro-3-(trifluoromethyl)-1-butene ($CHF$=$CFCF(CF_3)_2$); 1,1,2,4,4,4-hexafluoro-3-(trifluoromethyl)-1-butene ($CF_2$=$CFCH(CF_3)_2$); 1,1,1,4,4,4-hexafluoro-2-(trifluoromethyl)-2-butene ($CF_3CH$=$C(CF_3)_2$); 1,1,3,4,4,4-hexafluoro-3-(trifluoromethyl)-1-butene ($CF_2$=$CHCF(CF_3)_2$); 2,3,3,4,4,5,5,5-octafluoro-1-pentene ($CH_2$=$CFCF_2CF_2CF_3$); 1,2,3,3,4,4,5,5-octafluoro-1-pentene ($CHF$=$CFCF_2CF_2CHF_2$); 3,3,4,4-pentafluoro-2-(trifluoromethyl)-1-butene ($CH_2$=$C$ (CF₃)CF₂CF₃); 1,1,4,4-pentafluoro-3-(trifluoromethyl)-1-butene (CF₂=CHCH(CF₃)₂); 1,3,4,4,4-pentafluoro-3-(trifluoromethyl)-1-butene (CHF=CHCF(CF₃)₂); 1,1,4,4,4-pentafluoro-2-(trifluoromethyl)-1-butene (CF₂=C(CF₃)CH₂CF₃); 3,4,4,4-tetrafluoro-3-(trifluoromethyl)-1-butene ((CF₃)₂CFCH=CH₂); 3,3,4,4,5,5,5-heptafluoro-1-pentene (CF₃CF₂CF₂CH=CH₂); 2,3,3,4,4,5,5-heptafluoro-1-pentene (CH₂=CFCF₂CF₂CHF₂); 1,1,3,3,5,5,5-heptafluoro-1-butene (CF₂=CHCF₂CH₂CF₃); 1,1,1,2,4,4,4-heptafluoro-3-methyl-2-butene (CF₃CF=C(CF₃)(CH₃)); 2,4,4,4-tetrafluoro-3-(trifluoromethyl)-1-butene (CH₂=CFCH(CF₃)₂); 1,4,4,4-tetrafluoro-3-(trifluoromethyl)-1-butene (CHF=CHCH(CF₃)₂); 1,1,1,4-tetrafluoro-2-(trifluoromethyl)-2-butene (CH₂FCH=C(CF₃)₂); 1,1,1,3-tetrafluoro-2-(trifluoromethyl)-2-butene (CH₃CF=C(CF₃)₂); 1,1,2,3,3,4,4,5,5,6,6,6-dodecafluoro-1-hexene (CF₃(CF₂)₃CF=CF₂); 1,1,1,2,2,3,4,5,5,6,6,6-dodecafluoro-3-hexene (CF₃CF₂CF=CFCF₂CF₃); 1,1,1,4,4,4-hexafluoro-2,3-bis(trifluoromethyl)-2-butene ((CF₃)₂C=C(CF₃)₂); 1,1,1,2,3,4,5,5,5-nonafluoro-4-(trifluoromethyl)-2-pentene ((CF₃)₂CFCF=CFCF₃); 1,1,1,4,4,5,5,5-octafluoro-2-(trifluoromethyl)-2-pentene ((CF₃)₂C=CHC₂F₅); 1,1,1,3,4,5,5,5-octafluoro-4-(trifluoromethyl)-2-pentene ((CF₃)₂CFCF=CHCF₃); 3,3,4,4,5,5,6,6,6-nonafluoro-1-hexene (CF₃CF₂CF₂CF₂CH=CH₂); 4,4,4-trifluoro-3,3-bis(trifluoromethyl)-1-butene (CH₂=CHC(CF₃)₃); 1,1,1,4,4,4-hexafluoro-2-(trifluoromethyl)-3-methyl-2-butene ((CF₃)₂C=C(CH₃)(CF₃)); 2,3,3,5,5,5-hexafluoro-4-(trifluoromethyl)-1-pentene (CH₂=CFCF₂CH(CF₃)₂); 1,1,1,2,4,4,5,5,5-nonafluoro-3-methyl-2-pentene (CF₃CF=C(CH₃)CF₂CF₃); 1,1,1,5,5,5-hexafluoro-4-(trifluoromethyl)-2-pentene (CF₃CH=CHCH(CF₃)₂); 1,1,1,2,3,4,4,5,5,6,6,7,7,7-tetradecafluoro-2-heptene (CF₃CF=CFCF₂CF₂C₂F₅); 1,1,1,2,2,3,4,5,5,6,6,7,7,7-tetradecafluoro-3-heptene (CF₃CF₂CF=CFCF₂C₂F₅); 1,1,1,3,4,4,5,5,6,6,7,7,7-tridecafluoro-2-heptene (CF₃CH=CFCF₂CF₂C₂F₅); 1,1,1,2,4,4,5,5,6,6,7,7,7-tridecafluoro-2-heptene (CF₃CF=CHCF₂CF₂C₂F₅); 1,1,1,2,2,4,5,5,6,6,7,7,7-tridecafluoro-3-heptene (CF₃CF₂CH=CFCF₂C₂F₅); and 1,1,1,2,2,3,5,5,6,6,7,7,7-tridecafluoro-3-heptene (CF₃CF₂CF=CHCF₂C₂F₅).

The present invention further relates to a method of using a refrigerant or heat transfer fluid composition in refrigeration, air-conditioning, or heat pump apparatus, said method comprising introducing said composition into said apparatus having (a) centrifugal compressor; (b) multi-stage centrifugal compressor, or (c) single slab/single pass heat exchanger; wherein said refrigerant or heat transfer composition is employed in said apparatus to result in heating or cooling; and wherein said refrigerant or heat transfer composition comprises at least one fluoroolefin selected from the group consisting of:
(i) fluoroolefins of the formula E- or Z—R¹CH=CHR², wherein R¹ and R² are, independently, C₁ to C₆ perfluoroalkyl groups;
(ii) cyclic fluoroolefins of the formula cyclo-[CX=CY(CZW)ₙ—], wherein X, Y, Z, and W, independently, are H or F, and n is an integer from 2 to 5; or
(iii) fluoroolefins selected from the group consisting of: 1,2,3,3,3-pentafluoro-1-propene (CF₃CF=CHF); 1,1,3,3,3-pentafluoro-1-propene (CF₃CH=CF₂); 1,1,2,3,3-pentafluoro-1-propene (CHF₂CF=CF₂); 1,2,3,3-tetrafluoro-1-propene (CHF₂CF=CHF); 2,3,3,3-tetrafluoro-1-propene (CF₃CF=CH₂); 1,3,3,3-tetrafluoro-1-propene (CF₃CH=CHF); 1,1,2,3-tetrafluoro-1-propene (CH₂FCF=CF₂); 1,1,3,3-tetrafluoro-1-propene (CHF₂CH=CF₂); 2,3,3-trifluoro-1-propene (CHF₂CF=CH₂); 3,3,3-trifluoro-1-propene (CF₃CH=CH₂); 1,1,2-trifluoro-1-propene (CH₃CF=CF₂); 1,1,3-trifluoro-1-propene (CH₂FCH=CF₂); 1,2,3-trifluoro-1-propene (CH₂FCF=CHF); 1,3,3-trifluoro-1-propene (CHF₂CH=CHF); 1,1,1,2,3,4,4,4-octafluoro-2-butene (CF₃CF=CFCF₃); 1,1,2,3,3,4,4,4-octafluoro-1-butene (CF₃CF₂CF=CF₂); 1,1,1,2,4,4,4-heptafluoro-2-butene (CF₃CF=CHCF₃); 1,2,3,3,4,4,4-heptafluoro-1-butene (CHF=CFCF₂CF₃); 1,1,1,2,3,4,4-heptafluoro-2-butene (CHF₂CF=CFCF₃); 1,3,3,3-tetrafluoro-2-(trifluoromethyl)-1-propene ((CF₃)₂C=CHF); 1,1,3,3,4,4,4-heptafluoro-1-butene (CF₂=CHCF₂CF₃); 1,1,2,3,4,4,4-heptafluoro-1-butene (CF₂=CFCHFCF₃); 1,1,2,3,3,4,4-heptafluoro-1-butene (CF₂=CFCF₂CHF₂); 2,3,3,4,4,4-hexafluoro-1-butene (CF₃CF₂CF=CH₂); 1,3,3,4,4,4-hexafluoro-1-butene (CHF=CHCF₂CF₃); 1,2,3,4,4,4-hexafluoro-1-butene (CHF=CFCHFCF₃); 1,2,3,3,4,4-hexafluoro-1-butene (CHF=CFCF₂CHF₂); 1,1,2,3,4,4-hexafluoro-2-butene (CHF₂CF=CFCHF₂); 1,1,1,2,3,4-hexafluoro-2-butene (CH₂FCF=CFCF₃); 1,1,1,2,4,4-hexafluoro-2-butene (CHF₂CH=CFCF₃); 1,1,1,3,4,4-hexafluoro-2-butene (CF₃CH=CFCHF₂); 1,1,2,3,3,4-hexafluoro-1-butene (CF₂=CFCF₂CH₂F); 1,1,2,3,4,4-hexafluoro-1-butene (CF₂=CFCHFCHF₂); 3,3,3-trifluoro-2-(trifluoromethyl)-1-propene (CH₂=C(CF₃)₂); 1,1,1,2,4-pentafluoro-2-butene (CH₂FCH=CFCF₃); 1,1,1,3,4-pentafluoro-2-butene (CF₃CH=CFCH₂F); 3,3,4,4,4-pentafluoro-1-butene (CF₃CF₂CH=CH₂); 1,1,1,4,4-pentafluoro-2-butene (CHF₂CH=CHCF₃); 1,1,1,2,3-pentafluoro-2-butene (CH₃CF=CFCF₃); 2,3,3,4,4-pentafluoro-1-butene (CH₂=CFCF₂CHF₂); 1,1,2,4,4-pentafluoro-2-butene (CHF₂CF=CHCHF₂); 1,1,2,3,3-pentafluoro-1-butene (CH₃CF₂CF=CF₂); 1,1,2,3,4-pentafluoro-2-butene (CH₂FCF=CFCHF₂); 1,1,3,3,3-pentafluoro-2-methyl-1-propene (CF₂=C(CF₃)(CH₃)); 2-(difluoromethyl)-3,3,3-trifluoro-1-propene (CH₂=C(CHF₂)(CF₃)); 2,3,4,4,4-pentafluoro-1-butene (CH₂=CFCHFCF₃); 1,2,4,4,4-pentafluoro-1-butene (CHF=CFCH₂CF₃); 1,3,4,4,4-pentafluoro-1-butene (CHF=CHCHFCF₃); 1,3,3,4,4-pentafluoro-1-butene (CHF=CHCF₂CHF₂); 1,2,3,4,4-pentafluoro-1-butene (CHF=CFCHFCHF₂); 3,3,4,4-tetrafluoro-1-butene (CH₂=CHCF₂CHF₂); 1,1-difluoro-2-(difluoromethyl)-1-propene (CF₂=C(CHF₂)(CH₃)); 1,3,3,3-tetrafluoro-2-methyl-1-propene (CHF=C(CF₃)(CH₃)); 2-difluoromethyl-3,3-difluoro-1-propene (CH₂=C(CHF₂)₂); 1,1,1,2-tetrafluoro-2-butene (CF₃CF=CHCH₃); 1,1,1,3-tetrafluoro-2-butene (CH₃CF=CHCF₃); 1,1,1,2,3,4,4,5,5-decafluoro-2-pentene (CF₃CF=CFCF₂CF₃); 1,1,2,3,3,4,4,5,5,5-decafluoro-1-pentene (CF₂=CFCF₂CF₂CF₃); 1,1,1,4,4,4-hexafluoro-2-(trifluoromethyl)-2-butene ((CF₃)₂C=CHCF₃); 1,1,1,2,4,4,5,5,5-nonafluoro-2-pentene (CF₃CF=CHCF₂CF₃); 1,1,1,3,4,4,5,5,5-nonafluoro-2-pentene (CF₃CH=CFCF₂CF₃); 1,2,3,3,4,4,5,5,5-nonafluoro-1-pentene (CHF=CFCF₂CF₂CF₃); 1,1,3,3,4,4,5,5,5-nonafluoro-1-pentene (CF₂=CHCF₂CF₂CF₃); 1,1,2,3,3,4,4,5,5-nonafluoro-1-pentene (CF₂=CFCF₂CF₂CHF₂); 1,1,2,3,4,4,5,5,5-nonafluoro-2-pentene (CHF₂CF=CFCF₂CF₃); 1,1,1,2,3,4,4,5,5-nonafluoro-2-pentene (CF₃CF=CFCF₂CHF₂); 1,1,1,2,3,4,5,5,5-nonafluoro-2-pentene (CF₃CF=CFCHFCF₃); 1,2,3, 4,4,4-hexafluoro-3-(trifluoromethyl)-1-butene (CHF=CFCF(CF$_3$)$_2$); 1,1,2,4,4,4-hexafluoro-3-(trifluoromethyl)-1-butene (CF$_2$=CFCH(CF$_3$)$_2$); 1,1,1,4,4,4-hexafluoro-3-(trifluoromethyl)-2-butene (CF$_3$CH=C(CF$_3$)$_2$); 1,1,3,4,4,4-hexafluoro-3-(trifluoromethyl)-1-butene (CF$_2$=CHCF(CF$_3$)$_2$); 2,3,3,4,4,5,5,5-octafluoro-1-pentene (CH$_2$=CFCF$_2$CF$_2$CF$_3$); 1,2,3,3,4,4,5,5-octafluoro-1-pentene (CHF=CFCF$_2$CF$_2$CHF$_2$); 3,3,4,4,4-pentafluoro-2-(trifluoromethyl)-1-butene (CH$_2$=C(CF$_3$)CF$_2$CF$_3$); 1,1,4,4,4-pentafluoro-3-(trifluoromethyl)-1-butene (CF$_2$=CHCH(CF$_3$)$_2$); 1,3,4,4,4-pentafluoro-3-(trifluoromethyl)-1-butene (CHF=CHCF(CF$_3$)$_2$); 1,1,4,4,4-pentafluoro-2-(trifluoromethyl)-1-butene (CF$_2$=C(CF$_3$)CH$_2$CF$_3$); 3,4,4,4-tetrafluoro-3-(trifluoromethyl)-1-butene ((CF$_3$)$_2$CFCH=CH$_2$); 3,3,4,4,5,5,5-heptafluoro-1-pentene (CF$_3$CF$_2$CF$_2$CH=CH$_2$); 2,3,3,4,4,5,5-heptafluoro-1-pentene (CH$_2$=CFCF$_2$CF$_2$CHF$_2$); 1,1,3,3,5,5,5-heptafluoro-1-butene (CF$_2$=CHCF$_2$CH$_2$CF$_3$); 1,1,1,2,4,4,4-heptafluoro-3-methyl-2-butene (CF$_3$CF=C(CF$_3$)(CH$_3$)); 2,4,4,4-tetrafluoro-3-(trifluoromethyl)-1-butene (CH$_2$=CFCH(CF$_3$)$_2$); 1,4,4,4-tetrafluoro-3-(trifluoromethyl)-1-butene (CHF=CHCH(CF$_3$)$_2$); 1,1,1,4-tetrafluoro-2-(trifluoromethyl)-2-butene (CH$_2$FCH=C(CF$_3$)$_2$); 1,1,1,3-tetrafluoro-2-(trifluoromethyl)-2-butene (CH$_3$CF=C(CF$_3$)$_2$); 1,1,1-trifluoro-2-(trifluoromethyl)-2-butene ((CF$_3$)$_2$C=CHCH$_3$); 3,4,4,5,5,5-hexafluoro-2-pentene (CF$_3$CF$_2$CF=CHCH$_3$); 1,1,1,4,4,4-hexafluoro-2-methyl-2-butene (CF$_3$C(CH$_3$)=CHCF$_3$); 3,3,4,5,5,5-hexafluoro-1-pentene (CH$_2$=CHCF$_2$CHFCF$_3$); 3-(trifluoromethyl)-4,4,4-trifluoro-1-butene (CH$_2$=C(CF$_3$)CH$_2$CF$_3$); 1,1,2,3,3,4,4,5,5,6,6,6-dodecafluoro-1-hexene (CF$_3$(CF$_2$)$_3$CF=CF$_2$); 1,1,1,2,2,3,4,5,5,6,6,6-dodecafluoro-3-hexene (CF$_3$CF$_2$CF=CFCF$_2$CF$_3$); 1,1,1,4,4,4-hexafluoro-2,3-bis(trifluoromethyl)-2-butene ((CF$_3$)$_2$C=C(CF$_3$)$_2$); 1,1,1,2,3,4,5,5,5-nonafluoro-4-(trifluoromethyl)-2-pentene ((CF$_3$)$_2$CFCF=CFCF$_3$); 1,1,1,4,4,5,5,5-octafluoro-2-(trifluoromethyl)-2-pentene ((CF$_3$)$_2$C=CHC$_2$F$_5$); 1,1,1,3,4,5,5,5-octafluoro-4-(trifluoromethyl)-2-pentene ((CF$_3$)$_2$CFCF=CHCF$_3$); 3,3,4,4,5,5,6,6,6-nonafluoro-1-hexene (CF$_3$CF$_2$CF$_2$CF$_2$CH=CH$_2$); 4,4,4-trifluoro-3,3-bis(trifluoromethyl)-1-butene (CH$_2$=CHC(CF$_3$)$_3$); 1,1,1,4,4,4-hexafluoro-3-methyl-2-(trifluoromethyl)-2-butene ((CF$_3$)$_2$C=C(CH$_3$)(CF$_3$)); 2,3,3,5,5,5-hexafluoro-4-(trifluoromethyl)-1-pentene (CH$_2$=CFCF$_2$CH(CF$_3$)$_2$); 1,1,1,2,4,4,5,5,5-nonafluoro-3-methyl-2-pentene (CF$_3$CF=C(CH$_3$)CF$_2$CF$_3$); 1,1,1,5,5,5-hexafluoro-4-(trifluoromethyl)-2-pentene (CF$_3$CH=CHCH(CF$_3$)$_2$); 3,4,4,5,5,6,6,6-octafluoro-2-hexene (CF$_3$CF$_2$CF$_2$CF=CHCH$_3$); 3,3,4,4,5,5,6,6-octafluoro-1-hexene (CH$_2$=CHCF$_2$CF$_2$CF$_2$CHF$_2$); 1,1,1,4,4-pentafluoro-2-(trifluoromethyl)-2-pentene ((CF$_3$)$_2$C=CHCF$_2$CH$_3$); 4,4,5,5,5-pentafluoro-2-(trifluoromethyl)-1-pentene (CH$_2$=C(CF$_3$)CH$_2$C$_2$F$_5$); 3,3,4,4,5,5,5-heptafluoro-2-methyl-1-pentene (CF$_3$CF$_2$CF$_2$C(CH$_3$)=CH$_2$); 4,4,5,5,6,6,6-heptafluoro-2-hexene (CF$_3$CF$_2$CF$_2$CH=CHCH$_3$); 4,4,5,5,6,6,6-heptafluoro-1-hexene (CH$_2$=CHCH$_2$CF$_2$C$_2$F$_5$); 1,1,1,2,2,3,4-heptafluoro-3-hexene (CF$_3$CF$_2$CF=CFC$_2$H$_5$); 4,5,5,5-tetrafluoro-4-trifluoromethyl-1-pentene (CH$_2$=CHCH$_2$CF(CF$_3$)$_2$); 1,1,1,2,5,5,5-heptafluoro-4-methyl-2-pentene (CF$_3$CF=CHCH(CF$_3$)(CH$_3$)); 1,1,1,3-tetrafluoro-2-trifluoromethyl-2-pentene ((CF$_3$)$_2$C=CFC$_2$H$_5$); 1,1,1,2,3,4,4,5,5,6,6,7,7,7-tetradecafluoro-2-heptene (CF$_3$CF=CFCF$_2$CF$_2$C$_2$F$_5$); 1,1,1,2,2,3,4,5,5,6,6,7,7,7-tetradecafluoro-3-heptene (CF$_3$CF$_2$CF=CFCF$_2$C$_2$F$_5$); 1,1,1,3,4,4,5,5,6,6,7,7,7-tridecafluoro-2-heptene (CF$_3$CH=CFCF$_2$CF$_2$C$_2$F$_5$); 1,1,1,2,4,4,5,5,6,6,7,7,7-tridecafluoro-2-heptene (CF$_3$CF=CHCF$_2$CF$_2$C$_2$F$_5$); 1,1,1,2,2,4,5,5,6,6,7,7,7-tridecafluoro-3-heptene (CF$_3$CF$_2$CH=CFCF$_2$C$_2$F$_5$); 1,1,1,2,2,3,5,5,6,6,7,7,7-tridecafluoro-3-heptene (CF$_3$CF$_2$CF=CHCF$_2$C$_2$F$_5$); CF$_2$=CFOCF$_2$CF$_3$ (PEVE); CF$_2$=CFOCF$_3$ (PMVE) and combinations thereof.

DETAILED DESCRIPTION OF THE INVENTION

The present invention relates to compositions comprising at least one fluoroolefin. By fluoroolefin is meant any compound containing carbon, fluorine and optionally, hydrogen or oxygen that also contains at least one double bond. These fluoroolefins may be linear, branched or cyclic.

These compositions have a variety of utilities in working fluids, which include use as foaming agents, blowing agents, fire extinguishing agents, heat transfer mediums (such as heat transfer fluids and refrigerants for use in refrigeration systems, refrigerators, air-conditioning systems, heat pumps, chillers, and the like), to name a few.

A heat transfer fluid (also referred to herein as a heat transfer composition or heat transfer fluid composition) is a working fluid used to carry heat from a heat source to a heat sink.

A refrigerant is a compound or mixture of compounds that function as a heat transfer fluid in a cycle wherein the fluid undergoes a phase change from a liquid to a gas and back.

The present invention provides fluoroolefins having the formula E- or Z—R$^1$CH=CHR$^2$ (Formula I), wherein R$^1$ and R$^2$ are, independently, C$_1$ to C$_6$ perfluoroalkyl groups. Examples of R$^1$ and R$^2$ groups include, but are not limited to, CF$_3$, C$_2$F$_5$, CF$_2$CF$_2$CF$_3$, CF(CF$_3$)$_2$, CF$_2$CF$_2$CF$_2$CF$_3$, CF(CF$_3$)CF$_2$CF$_3$, CF$_2$CF(CF$_3$)$_2$, C(CF$_3$)$_3$, CF$_2$CF$_2$CF$_2$CF$_2$CF$_3$, CF$_2$CF$_2$CF(CF$_3$)$_2$, C(CF$_3$)$_2$C$_2$F$_5$, CF$_2$CF$_2$CF$_2$CF$_2$CF$_2$CF$_3$, CF(CF$_3$) CF$_2$CF$_2$C$_2$F$_5$, and C(CF$_3$)$_2$ CF$_2$C$_2$F$_5$. In one embodiment the fluoroolefins of Formula I, have at least about 3 carbon atoms in the molecule. In another embodiment, the fluoroolefins of Formula I have at least about 4 carbon atoms in the molecule. In yet another embodiment, the fluoroolefins of Formula I have at least about 5 carbon atoms in the molecule. Exemplary, non-limiting Formula I compounds are presented in Table 1.

TABLE 1

| Code | Structure | Chemical Name |
| --- | --- | --- |
| F11E | CF$_3$CH=CHCF$_3$ | 1,1,1,4,4,4-hexafluoro-2-butene |
| F12E | CF$_3$CH=CHC$_2$F$_5$ | 1,1,1,4,4,5,5,5-octafluoro-2-pentene |
| F13E | CF$_3$CH=CHCF$_2$C$_2$F$_5$ | 1,1,1,4,4,5,5,6,6,6-decafluoro-2-hexene |
| F13iE | CF$_3$CH=CHCF(CF$_3$)$_2$ | 1,1,1,4,5,5,5-heptafluoro-4-(trifluoromethyl)-2-pentene |
| F22E | C$_2$F$_5$CH=CHC$_2$F$_5$ | 1,1,1,2,2,5,5,6,6,6-decafluoro-3-hexene |
| F14E | CF$_3$CH=CH(CF$_2$)$_3$CF$_3$ | 1,1,1,4,4,5,5,6,6,7,7,7-dodecafluoro-2-heptene |
| F14iE | CF$_3$CH=CHCF$_2$CF(CF$_3$)$_2$ | 1,1,1,4,4,5,6,6,6-nonafluoro-5-(trifluoromethyl)-2-hexene |
| F14sE | CF$_3$CH=CHCF(CF$_3$)C$_2$F$_5$ | 1,1,1,4,5,5,6,6,6-nonfluoro-4-(trifluoromethyl)-2-hexene |
| F14tE | CF$_3$CH=CHC(CF$_3$)$_3$ | 1,1,1,5,5,5-hexafluoro-4,4-bis(trifluoromethyl)-2-pentene |
| F23E | C$_2$F$_5$CH=CHCF$_2$C$_2$F$_5$ | 1,1,1,2,2,5,5,6,6,7,7,7-dodecafluoro-3-heptene |
| F23iE | C$_2$F$_5$CH=CHCF(CF$_3$)$_2$ | 1,1,1,2,2,5,6,6,6-nonafluoro-5-(trifluoromethyl)-3-hexene |
| F15E | CF$_3$CH=CH(CF$_2$)$_4$CF$_3$ | 1,1,1,4,4,5,5,6,6,7,7,8,8,8-tetradecafluoro-2-octene |

TABLE 1-continued

| Code | Structure | Chemical Name |
|---|---|---|
| F15iE | $CF_3CH=CH-CF_2CF_2CF(CF_3)_2$ | 1,1,1,4,4,5,5,6,7,7,7-undecafluoro-6-(trifluoromethyl)-2-heptene |
| F15tE | $CF_3CH=CH-C(CF_3)_2C_2F_5$ | 1,1,1,5,5,6,6,6-octafluoro-4,4-bis(trifluoromethyl)-2-hexene |
| F24E | $C_2F_5CH=CH(CF_2)_3CF_3$ | 1,1,1,2,2,5,5,6,6,7,7,8,8,8-tetradecafluoro-3-octene |
| F24iE | $C_2F_5CH=CHCF_2CF(CF_3)_2$ | 1,1,1,2,2,5,5,6,7,7,7-undecafluoro-6-(trifluoromethyl)-3-heptene |
| F24sE | $C_2F_5CH=CHCF(CF_3)C_2F_5$ | 1,1,1,2,2,5,6,6,7,7,7-undecafluoro-5-(trifluoromethyl)-3-heptene |
| F24tE | $C_2F_5CH=CHC(CF_3)_3$ | 1,1,1,2,2,6,6,6-octafluoro-5,5-bis(trifluoromethyl)-3-hexene |
| F33E | $C_2F_5CF_2CH=CHCF_2C_2F_5$ | 1,1,1,2,2,3,3,6,6,7,7,8,8,8-tetradecafluoro-4-octene |
| F3i3iE | $(CF_3)_2CFCH=CHCF(CF_3)_2$ | 1,1,1,2,5,6,6,6-octafluoro-2,5-bis(trifluoromethyl)-3-hexene |
| F33iE | $C_2F_5CF_2CH=CHCF(CF_3)_2$ | 1,1,1,2,5,5,6,6,7,7,7-undecafluoro-2-(trifluoromethyl)-3-heptene |
| F16E | $CF_3CH=CH(CF_2)_5CF_3$ | 1,1,1,4,4,5,5,6,6,7,7,8,8,9,9,9-hexadecafluoro-2-nonene |
| F16sE | $CF_3CH=CHCF(CF_3)(CF_2)_2C_2F_5$ | 1,1,1,4,5,5,6,6,7,7,8,8,8-tridecafluoro-4-(trifluoromethyl)-2-heptene |
| F16tE | $CF_3CH=CHC(CF_3)_2CF_2C_2F_5$ | 1,1,1,6,6,6-octafluoro-4,4-bis(trifluoromethyl)-2-heptene |
| F25E | $C_2F_5CH=CH(CF_2)_4CF_3$ | 1,1,1,2,2,5,5,6,6,7,7,8,8,9,9,9-hexadecafluoro-3-nonene |
| F25iE | $C_2F_5CH=CH-CF_2CF_2CF(CF_3)_2$ | 1,1,1,2,2,5,5,6,6,7,8,8,8-tridecafluoro-7-(trifluoromethyl)-3-octene |
| F25tE | $C_2F_5CH=CH-C(CF_3)_2C_2F_5$ | 1,1,1,2,2,6,6,7,7,7-decafluoro-5,5-bis(trifluoromethyl)-3-heptene |
| F34E | $C_2F_5CF_2CH=CH-(CF_2)_3CF_3$ | 1,1,1,2,2,3,3,6,6,7,7,8,8,9,9,9-hexadecafluoro-4-nonene |
| F34iE | $C_2F_5CF_2CH=CH-CF_2CF(CF_3)_2$ | 1,1,1,2,2,3,3,6,6,7,8,8,8-tridecafluoro-7-(trifluoromethyl)-4-octene |
| F34sE | $C_2F_5CF_2CH=CHCF(CF_3)C_2F_5$ | 1,1,1,2,2,3,3,6,7,7,8,8,8-tridecafluoro-6-(trifluoromethyl)-4-octene |
| F34tE | $C_2F_5CF_2CH=CHC(CF_3)_3$ | 1,1,1,5,5,6,6,7,7,7-decafluoro-2,2-bis(trifluoromethyl)-3-heptene |
| F3i4E | $(CF_3)_2CFCH=CH(CF_2)_3CF_3$ | 1,1,1,2,5,5,6,6,7,7,8,8,8-tridecafluoro-2(trifluoromethyl)-3-octene |
| F3i4iE | $(CF_3)_2CFCH=CHCF_2CF(CF_3)_2$ | 1,1,1,2,5,5,6,7,7,7-decafluoro-2,6-bis(trifluoromethyl)-3-heptene |
| F3i4sE | $(CF_3)_2CFCH=CHCF(CF_3)C_2F_5$ | 1,1,1,2,5,6,6,7,7,7-decafluoro-2,5-bis(trifluoromethyl)-3-heptene |
| F3i4tE | $(CF_3)_2CFCH=CHC(CF_3)_3$ | 1,1,1,2,6,6,6-heptafluoro-2,5,5-tris(trifluoromethyl)-3-hexene |
| F26E | $C_2F_5CH=CH(CF_2)_5CF_3$ | 1,1,1,2,2,5,5,6,6,7,7,8,8,9,9,10,10,10-octadecafluoro-3-decene |
| F26sE | $C_2F_5CH=CHCF(CF_3)(CF_2)_2C_2F_5$ | 1,1,1,2,2,5,5,6,6,7,7,8,8,9,9,9-pentadecafluoro-5-(trifluoromethyl)-3-nonene |
| F26tE | $C_2F_5CH=CHC(CF_3)_2-CF_2C_2F_5$ | 1,1,1,2,2,6,6,7,7,8,8,8-dodecafluoro-5,5-bis(trifluoromethyl)-3-octene |
| F35E | $C_2F_5CF_2CH=CH-(CF_2)_4CF_3$ | 1,1,1,2,2,3,3,6,6,7,7,8,8,9,9,10,10,10-octadecafluoro-4-decene |
| F35iE | $C_2F_5CF_2CH=CHCF_2CF_2-CF(CF_3)_2$ | 1,1,1,2,2,3,3,6,6,7,7,8,9,9,9-pentadecafluoro-8-(trifluoromethyl)-4-nonene |
| F35tE | $C_2F_5CF_2CH=CH-C(CF_3)_2C_2F_5$ | 1,1,1,2,2,3,3,7,7,8,8-dodecafluoro-6,6-bis(trifluoromethyl)-4-octene |
| F3i5E | $(CF_3)_2CFCH=CH-(CF_2)_4CF_3$ | 1,1,1,2,5,5,6,6,7,7,8,8,9,9,9-pentadecafluoro-2-(trifluoromethyl)-3-nonene |
| F3i5iE | $(CF_3)_2CFCH=CHCF_2CF_2-CF(CF_3)_2$ | 1,1,1,2,5,5,6,6,7,8,8,8-dodecafluoro-2,7-bis(trifluoromethyl)-3-octene |
| F3i5tE | $(CF_3)_2CFCH=CHC(CF_3)_2C_2F_5$ | 1,1,1,2,6,6,7,7,7-nonafluoro-2,5,5-tris(trifluoromethyl)-3-heptene |
| F44E | $CF_3(CF_2)_3CH=CH(CF_2)_3CF_3$ | 1,1,1,2,2,3,3,4,4,7,7,8,8,9,9,10,10,10-octadecafluoro-5-decene |
| F44iE | $CF_3(CF_2)_3CH=CH-CF_2CF(CF_3)_2$ | 1,1,1,2,3,3,6,6,7,7,8,8,9,9,9-pentadecafluoro-2-(trifluoromethyl)-4-nonene |
| F44sE | $CF_3(CF_2)_3CH=CHCF(CF_3)C_2F_5$ | 1,1,1,2,2,3,6,6,7,7,8,8,9,9,9-pentadecafluoro-3-(trifluoromethyl)-4-nonene |
| F44tE | $CF_3(CF_2)_3CH=CHC(CF_3)_3$ | 1,1,1,5,5,6,6,7,7,8,8,8-dodecafluoro-2,2,-bis(trifluoromethyl)-3-octene |
| F4i4iE | $(CF_3)_2CFCF_2CH=CHCF_2CF-(CF_3)_2$ | 1,1,1,2,3,3,6,6,7,8,8,8-dodecafluoro-2,7-bis(trifluoromethyl)-4-octene |
| F4i4sE | $(CF_3)_2CFCF_2CH=CHCF(CF_3)-C_2F_5$ | 1,1,1,2,3,3,6,7,7,8,8,8-dodecafluoro-2,6-bis(trifluoromethyl)-4-octene |
| F4i4tE | $(CF_3)_2CFCF_2CH=CHC(CF_3)_3$ | 1,1,1,5,5,6,7,7,7-nonafluoro-2,2,6-tris(trifluoromethyl)-3-heptene |
| F4s4sE | $C_2F_5CF(CF_3)CH=CH-CF(CF_3)C_2F_5$ | 1,1,1,2,2,3,6,7,7,8,8,8-dodecafluoro-3,6-bis(trifluoromethyl)-4-octene |
| F4s4tE | $C_2F_5CF(CF_3)CH=CH-C(CF_3)_3$ | 1,1,1,5,6,6,7,7,7-nonafluoro-2,2,5-tris(trifluoromethyl)-3-heptene |
| F4t4tE | $(CF_3)_3CCH=CH-C(CF_3)_3$ | 1,1,1,6,6,6-hexafluoro-2,2,5,5-tetrakis(trifluoromethyl)-3-hexene |

Compounds of Formula I may be prepared by contacting a perfluoroalkyl iodide of the formula $R^{11}$ with a perfluoroalkyltrihydroolefin of the formula $R^2CH=CH_2$ to form a trihydroiodoperfluoroalkane of the formula $R^1CH_2CHIR^2$. This trihydroiodoperfluoroalkane can then be dehydroiodinated to form $R^1CH=CHR^2$. Alternatively, the olefin $R^1CH=CHR^2$ may be prepared by dehydroiodination of a trihydroiodoperfluoroalkane of the formula $R^1CHICH_2R^2$ formed in turn by reacting a perfluoroalkyl iodide of the formula $R^2I$ with a perfluoroalkyltrihydroolefin of the formula $R^1CH=CH_2$.

Said contacting of a perfluoroalkyl iodide with a perfluoroalkyltrihydroolefin may take place in batch mode by combining the reactants in a suitable reaction vessel capable of operating under the autogenous pressure of the reactants and products at reaction temperature. Suitable reaction vessels include fabricated from stainless steels, in particular of the austenitic type, and the well-known high nickel alloys such as Monel® nickel-copper alloys, Hastelloy® nickel based alloys and Inconel® nickel-chromium alloys.

Alternatively, the reaction may take be conducted in semibatch mode in which the perfluoroalkyltrihydroolefin reactant is added to the perfluoroalkyl iodide reactant by means of a suitable addition apparatus such as a pump at the reaction temperature.

The ratio of perfluoroalkyl iodide to perfluoroalkyltrihydroolefin should be between about 1:1 to about 4:1, preferably from about 1.5:1 to 2.5:1. Ratios less than 1.5:1 tend to result in large amounts of the 2:1 adduct as reported by Jeanneaux, et. al. in Journal of Fluorine Chemistry, Vol. 4, pages 261-270 (1974).

Preferred temperatures for contacting of said perfluoroalkyl iodide with said perfluoroalkyltrihydroolefin are preferably within the range of about 150° C. to 300° C., preferably from about 170° C. to about 250° C., and most preferably from about 180° C. to about 230° C. Suitable contact times for the reaction of the perfluoroalkyl iodide with the perfluoroalkyltrihydroolefin are from about 0.5 hour to 18 hours, preferably from about 4 to about 12 hours.

The trihydroiodoperfluoroalkane prepared by reaction of the perfluoroalkyl iodide with the perfluoroalkyltrihydroolefin may be used directly in the dehydroiodination step or may preferably be recovered and purified by distillation prior to the dehydroiodination step.

The dehydroiodination step is carried out by contacting the trihydroiodoperfluoroalkane with a basic substance. Suitable basic substances include alkali metal hydroxides (e.g., sodium hydroxide or potassium hydroxide), alkali metal oxide (for example, sodium oxide), alkaline earth metal hydroxides (e.g., calcium hydroxide), alkaline earth metal oxides (e.g., calcium oxide), alkali metal alkoxides (e.g., sodium methoxide or sodium ethoxide), aqueous ammonia, sodium amide, or mixtures of basic substances such as soda lime. Preferred basic substances are sodium hydroxide and potassium hydroxide.

Said contacting of the trihydroiodoperfluoroalkane with a basic substance may take place in the liquid phase preferably in the presence of a solvent capable of dissolving at least a portion of both reactants. Solvents suitable for the dehydroiodination step include one or more polar organic solvents such as alcohols (e.g., methanol, ethanol, n-propanol, isopropanol, n-butanol, isobutanol, and tertiary butanol), nitriles (e.g., acetonitrile, propionitrile, butyronitrile, benzonitrile, or adiponitrile), dimethyl sulfoxide, N,N-dimethylformamide, N,N-dimethylacetamide, or sulfolane. The choice of solvent may depend on the boiling point product and the ease of separation of traces of the solvent from the product during purification. Typically, ethanol or isopropanol are good solvents for the reaction.

Typically, the dehydroiodination reaction may be carried out by addition of one of the reactants (either the basic substance or the trihydroiodoperfluoroalkane) to the other reactant in a suitable reaction vessel. Said reaction may be fabricated from glass, ceramic, or metal and is preferably agitated with an impeller or stirring mechanism.

Temperatures suitable for the dehydroiodination reaction are from about 10° C. to about 100° C., preferably from about 20° C. to about 70° C. The dehydroiodination reaction may be carried out at ambient pressure or at reduced or elevated pressure. Of note are dehydroiodination reactions in which the compound of Formula I is distilled out of the reaction vessel as it is formed.

Alternatively, the dehydroiodination reaction may be conducted by contacting an aqueous solution of said basic substance with a solution of the trihydroiodoperfluoroalkane in one or more organic solvents of lower polarity such as an alkane (e.g., hexane, heptane, or octane), aromatic hydrocarbon (e.g., toluene), halogenated hydrocarbon (e.g., methylene chloride, chloroform, carbon tetrachloride, or perchloroethylene), or ether (e.g., diethyl ether, methyl tert-butyl ether, tetrahydrofuran, 2-methyl tetrahydrofuran, dioxane, dimethoxyethane, diglyme, or tetraglyme) in the presence of a phase transfer catalyst. Suitable phase transfer catalysts include quaternary ammonium halides (e.g., tetrabutylammonium bromide, tetrabutylammonium hydrosulfate, triethylbenzylammonium chloride, dodecyltrimethylammonium chloride, and tricaprylylmethylammonium chloride), quaternary phosphonium halides (e.g., triphenylmethylphosphonium bromide and tetraphenylphosphonium chloride), or cyclic polyether compounds known in the art as crown ethers (e.g., 18-crown-6 and 15-crown-5).

Alternatively, the dehydroiodination reaction may be conducted in the absence of solvent by adding the trihydroiodoperfluoroalkane to a solid or liquid basic substance.

Suitable reaction times for the dehydroiodination reactions are from about 15 minutes to about six hours or more depending on the solubility of the reactants. Typically the dehydroiodination reaction is rapid and requires about 30 minutes to about three hours for completion.

The compound of formula I may be recovered from the dehydroiodination reaction mixture by phase separation after addition of water, by distillation, or by a combination thereof.

In another embodiment of the present invention, fluoroolefins comprise cyclic fluoroolefins (cyclo-[CX=CY(CZW)$_n$—] (Formula II), wherein X, Y, Z, and W are independently selected from H and F, and n is an integer from 2 to 5). Representative cyclic fluoroolefins of Formula II are listed in Table 2.

TABLE 2

| Cyclic fluoroolefins | Structure | Chemical name |
|---|---|---|
| FC-C1316cc | cyclo-CF$_2$CF$_2$CF=CF— | 1,2,3,3,4,4-hexafluorocyclobutene |
| HFC-C1334cc | cyclo-CF$_2$CF$_2$CH=CH— | 3,3,4,4-tetrafluorocyclobutene |
| HFC-C1436 | cyclo-CF$_2$CF$_2$CF$_2$CH=CH— | 3,3,4,4,5,5,-hexafluorocyclopentene |
| FC-C1418y | cyclo-CF$_2$CF=CFCF$_2$CF$_2$— | 1,2,3,3,4,4,5,5-octafluorocyclopentene |
| FC-C151-10y | cyclo-CF$_2$CF=CFCF$_2$CF$_2$CF$_2$— | 1,2,3,3,4,4,5,5,6,6-decafluorocyclohexene |

In another embodiment, fluoroolefins may comprise those compounds listed in Table 3.

TABLE 3

| Name | Structure | Chemical name |
|---|---|---|
| HFC-1225ye | CF$_3$CF=CHF | 1,2,3,3,3-pentafluoro-1-propene |
| HFC-1225zc | CF$_3$CH=CF$_2$ | 1,1,3,3,3-pentafluoro-1-propene |
| HFC-1225yc | CHF$_2$CF=CF$_2$ | 1,1,2,3,3-pentafluoro-1-propene |
| HFC-1234ye | CHF$_2$CF=CHF | 1,2,3,3-tetrafluoro-1-propene |
| HFC-1234yf | CF$_3$CF=CH$_2$ | 2,3,3,3-tetrafluoro-1-propene |
| HFC-1234ze | CF$_3$CH=CHF | 1,3,3,3-tetrafluoro-1-propene |
| HFC-1234yc | CH$_2$FCF=CF$_2$ | 1,1,2,3-tetrafluoro-1-propene |
| HFC-1234zc | CHF$_2$CH=CF$_2$ | 1,1,3,3-tetrafluoro-1-propene |
| HFC-1243yf | CHF$_2$CF=CH$_2$ | 2,3,3-trifluoro-1-propene |
| HFC-1243zf | CF$_3$CH=CH$_2$ | 3,3,3-trifluoro-1-propene |
| HFC-1243yc | CH$_3$CF=CF$_2$ | 1,1,2-trifluoro-1-propene |
| HFC-1243zc | CH$_2$FCH=CF$_2$ | 1,1,3-trifluoro-1-propene |
| HFC-1243ye | CH$_2$FCF=CHF | 1,2,3-trifluoro-1-propene |
| HFC-1243ze | CHF$_2$CH=CHF | 1,3,3-trifluoro-1-propene |
| FC-1318my | CF$_3$CF=CFCF$_3$ | 1,1,1,2,3,4,4,4-octafluoro-2-butene |
| FC-1318cy | CF$_3$CF$_2$CF=CF$_2$ | 1,1,2,3,3,4,4,4-octafluoro-1-butene |
| HFC-1327my | CF$_3$CF=CHCF$_3$ | 1,1,1,2,4,4,4-heptafluoro-2-butene |
| HFC-1327ye | CHF=CFCF$_2$CF$_3$ | 1,2,3,3,4,4,4-heptafluoro-1-butene |

TABLE 3-continued

| Name | Structure | Chemical name |
|---|---|---|
| HFC-1327py | $CHF_2CF=CFCF_3$ | 1,1,1,2,3,4,4-heptafluoro-2-butene |
| HFC-1327et | $(CF_3)_2C=CHF$ | 1,3,3,3-tetrafluoro-2-(trifluoromethyl)-1-propene |
| HFC-1327cz | $CF_2=CHCF_2CF_3$ | 1,1,3,3,4,4,4-heptafluoro-1-butene |
| HFC-1327cye | $CF_2=CFCHFCF_3$ | 1,1,2,3,4,4,4-heptafluoro-1-butene |
| HFC-1327cyc | $CF_2=CFCF_2CHF_2$ | 1,1,2,3,3,4,4-heptafluoro-1-butene |
| HFC-1336yf | $CF_3CF_2CF=CH_2$ | 2,3,3,4,4,4-hexafluoro-1-butene |
| HFC-1336ze | $CHF=CHCF_2CF_3$ | 1,3,3,4,4,4-hexafluoro-1-butene |
| HFC-1336eye | $CHF=CFCHFCF_3$ | 1,2,3,4,4,4-hexafluoro-1-butene |
| HFC-1336eyc | $CHF=CFCF_2CHF_2$ | 1,2,3,3,4,4-hexafluoro-1-butene |
| HFC-1336pyy | $CHF_2CF=CFCHF_2$ | 1,1,2,3,4,4-hexafluoro-2-butene |
| HFC-1336qy | $CH_2FCF=CFCF_3$ | 1,1,1,2,3,4-hexafluoro-2-butene |
| HFC-1336pz | $CHF_2CH=CFCF_3$ | 1,1,1,2,4,4-hexafluoro-2-butene |
| HFC-1336mzy | $CF_3CH=CFCHF_2$ | 1,1,1,3,4,4-hexafluoro-2-butene |
| HFC-1336qc | $CF_2=CFCF_2CH_2F$ | 1,1,2,3,3,4-hexafluoro-1-butene |
| HFC-1336pe | $CF_2=CFCHFCHF_2$ | 1,1,2,3,4,4-hexafluoro-1-butene |
| HFC-1336ft | $CH_2=C(CF_3)_2$ | 3,3,3-trifluoro-2-(trifluoromethyl)-1-propene |
| HFC-1345qz | $CH_2FCH=CFCF_3$ | 1,1,1,2,4-pentafluoro-2-butene |
| HFC-1345mzy | $CF_3CH=CFCH_2F$ | 1,1,1,3,4-pentafluoro-2-butene |
| HFC-1345fz | $CF_3CF_2CH=CH_2$ | 3,3,4,4,4-pentafluoro-1-butene |
| HFC-1345mzz | $CHF_2CH=CHCF_3$ | 1,1,1,4,4-pentafluoro-2-butene |
| HFC-1345sy | $CH_3CF=CFCF_3$ | 1,1,1,2,3-pentafluoro-2-butene |
| HFC-1345fyc | $CH_2=CFCF_2CHF_2$ | 2,3,3,4,4-pentafluoro-1-butene |
| HFC-1345pyz | $CHF_2CF=CHCHF_2$ | 1,1,2,4,4-pentafluoro-2-butene |
| HFC-1345cyc | $CH_3CF_2CF=CF_2$ | 1,1,2,3,3-pentafluoro-1-butene |
| HFC-1345pyy | $CH_2FCF=CFCHF_2$ | 1,1,2,3,4-pentafluoro-2-butene |
| HFC-1345eyc | $CH_2FCF_2CF=CF_2$ | 1,2,3,3,4-pentafluoro-1-butene |
| HFC-1345ctm | $CF_2=C(CF_3)(CH_3)$ | 1,1,3,3,3-pentafluoro-2-methyl-1-propene |
| HFC-1345ftp | $CH_2=C(CHF_2)(CF_3)$ | 2-(difluoromethyl)-3,3,3-trifluoro-1-propene |
| HFC1345fye | $CH_2=CFCHFCF_3$ | 2,3,4,4,4-pentafluoro-1-butene |
| HFC-1345eyf | $CHF=CFCH_2CF_3$ | 1,2,4,4,4-pentafluoro-1-butene |
| HFC-1345eze | $CHF=CHCHFCF_3$ | 1,3,4,4,4-pentafluoro-1-butene |
| HFC-1345ezc | $CHF=CHCF_2CHF_2$ | 1,3,3,4,4-pentafluoro-1-butene |
| HFC-1345eye | $CHF=CFCHFCHF_2$ | 1,2,3,4,4-pentafluoro-1-butene |
| HFC-1354fzc | $CH_2=CHCF_2CHF_2$ | 3,3,4,4-tetrafluoro-1-butene |
| HFC-1354ctp | $CF_2=C(CHF_2)(CH_3)$ | 1,1,3,3-tetrafluoro-2-methyl-1-propene |
| HFC-1354etm | $CHF=C(CF_3)(CH_3)$ | 1,3,3,3-tetrafluoro-2-methyl-1-propene |
| HFC-1354tfp | $CH_2=C(CHF_2)_2$ | 2-(difluoromethyl)-3,3-difluoro-1-propene |
| HFC-1354my | $CF_3CF=CHCH_3$ | 1,1,1,2-tetrafluoro-2-butene |
| HFC-1354mzy | $CH_3CF=CHCF_3$ | 1,1,1,3-tetrafluoro-2-butene |
| FC-141-10myy | $CF_3CF=CFCF_2CF_3$ | 1,1,1,2,3,4,4,5,5,5-decafluoro-2-pentene |
| FC-141-10cy | $CF_2=CFCF_2CF_2CF_3$ | 1,1,2,3,3,4,4,5,5,5-decafluoro-1-pentene |
| HFC-1429mzt | $(CF_3)_2C=CHCF_3$ | 1,1,1,4,4,4-hexafluoro-2-(trifluoromethyl)-2-butene |
| HFC-1429myz | $CF_3CF=CHCF_2CF_3$ | 1,1,1,2,4,4,5,5,5-nonafluoro-2-pentene |
| HFC-1429mzy | $CF_3CH=CFCF_2CF_3$ | 1,1,1,3,4,4,5,5,5-nonafluoro-2-pentene |
| HFC-1429eyc | $CHF=CFCF_2CF_2CF_3$ | 1,2,3,3,4,4,5,5,5-nonafluoro-1-pentene |
| HFC-1429czc | $CF_2=CHCF_2CF_2CF_3$ | 1,1,3,3,4,4,5,5,5-nonafluoro-1-pentene |
| HFC-1429cycc | $CF_2=CFCF_2CF_2CHF_2$ | 1,1,2,3,3,4,4,5,5-nonafluoro-1-pentene |
| HFC-1429pyy | $CHF_2CF=CFCF_2CF_3$ | 1,1,2,3,4,4,5,5,5-nonafluoro-2-pentene |
| HFC-1429myyc | $CF_3CF=CFCF_2CHF_2$ | 1,1,1,2,3,4,4,5,5-nonafluoro-2-pentene |
| HFC-1429myye | $CF_3CF=CFCHFCF_3$ | 1,1,1,2,3,4,5,5,5-nonafluoro-2-pentene |
| HFC-1429eyym | $CHF=CFCF(CF_3)_2$ | 1,2,3,4,4,4-hexafluoro-3-(trifluoromethyl)-1-butene |
| HFC-1429cyzm | $CF_2=CFCH(CF_3)_2$ | 1,1,2,4,4,4-hexafluoro-3-(trifluoromethyl)-1-butene |
| HFC-1429mzt | $CF_3CH=C(CF_3)_2$ | 1,1,1,4,4,4-hexafluoro-2-(trifluoromethyl)-2-butene |
| HFC-1429czym | $CF_2=CHCF(CF_3)_2$ | 1,1,3,4,4,4-hexafluoro-3-(trifluoromethyl)-1-butene |
| HFC-1438fy | $CH_2=CFCF_2CF_2CF_3$ | 2,3,3,4,4,5,5,5-octafluoro-1-pentene |
| HFC-1438eycc | $CHF=CFCF_2CF_2CHF_2$ | 1,2,3,3,4,4,5,5-octafluoro-1-pentene |
| HFC-1438ftmc | $CH_2=C(CF_3)CF_2CF_3$ | 3,3,4,4,4-pentafluoro-2-(trifluoromethyl)-1-butene |
| HFC-1438czzm | $CF_2=CHCH(CF_3)_2$ | 1,1,4,4,4-pentafluoro-3-(trifluoromethyl)-1-butene |
| HFC-1438ezym | $CHF=CHCF(CF_3)_2$ | 1,3,4,4,4-pentafluoro-3-(trifluoromethyl)-1-butene |
| HFC-1438ctmf | $CF_2=C(CF_3)CH_2CF_3$ | 1,1,4,4,4-pentafluoro-2-(trifluoromethyl)-1-butene |
| HFC-1447fzy | $(CF_3)_2CFCH=CH_2$ | 3,4,4,4-tetrafluoro-3-(trifluoromethyl)-1-butene |
| HFC-1447fz | $CF_3CF_2CF_2CH=CH_2$ | 3,3,4,4,5,5,5-heptafluoro-1-pentene |
| HFC-1447fycc | $CH_2=CFCF_2CF_2CHF_2$ | 2,3,3,4,4,5,5-heptafluoro-1-pentene |
| HFC-1447czcf | $CF_2=CHCF_2CH_2CF_3$ | 1,1,3,3,5,5,5-heptafluoro-1-pentene |
| HFC-1447mytm | $CF_3CF=C(CF_3)(CH_3)$ | 1,1,1,2,4,4,4-heptafluoro-3-methyl-2-butene |
| HFC-1447fyz | $CH_2=CFCH(CF_3)_2$ | 2,4,4,4-tetrafluoro-3-(trifluoromethyl)-1-butene |
| HFC-1447ezz | $CHF=CHCH(CF_3)_2$ | 1,4,4,4-tetrafluoro-3-(trifluoromethyl)-1-butene |

TABLE 3-continued

| Name | Structure | Chemical name |
|---|---|---|
| HFC-1447qzt | $CH_2FCH=C(CF_3)_2$ | 1,4,4,4-tetrafluoro-2-(trifluoromethyl)-2-butene |
| HFC-1447syt | $CH_3CF=C(CF_3)_2$ | 2,4,4,4-tetrafluoro-2-(trifluoromethyl)-2-butene |
| HFC-1456szt | $(CF_3)_2C=CHCH_3$ | 3-(trifluoromethyl)-4,4,4-trifluoro-2-butene |
| HFC-1456szy | $CF_3CF_2CF=CHCH_3$ | 3,4,4,5,5,5-hexafluoro-2-pentene |
| HFC-1456mstz | $CF_3C(CH_3)=CHCF_3$ | 1,1,1,4,4,4-hexafluoro-2-methyl-2-butene |
| HFC-1456fzce | $CH_2=CHCF_2CHFCF_3$ | 3,3,4,5,5,5-hexafluoro-1-pentene |
| HFC-1456ftmf | $CH_2=C(CF_3)CH_2CF_3$ | 4,4,4-trifluoro-2-(trifluoromethyl)-1-butene |
| FC-151-12c | $CF_3(CF_2)_3CF=CF_2$ | 1,1,2,3,3,4,4,5,5,6,6,6-dodecafluoro-1-hexene (or perfluoro-1-hexene) |
| FC-151-12mcy | $CF_3CF_2CF=CFCF_2CF_3$ | 1,1,1,2,2,3,4,5,5,6,6,6-dodecafluoro-3-hexene (or perfluoro-3-hexene) |
| FC-151-12mmtt | $(CF_3)_2C=C(CF_3)_2$ | 1,1,1,4,4,4-hexafluoro-2,3-bis(trifluoromethyl)-2-butene |
| FC-151-12mmzz | $(CF_3)_2CFCF=CFCF_3$ | 1,1,1,2,3,4,5,5,5-nonafluoro-4-(trifluoromethyl)-2-pentene |
| HFC-152-11mmtz | $(CF_3)_2C=CHC_2F_5$ | 1,1,1,4,4,5,5,5-octafluoro-2-(trifluoromethyl)-2-pentene |
| HFC-152-11mmyyz | $(CF_3)_2CFCF=CHCF_3$ | 1,1,1,3,4,5,5,5-octafluoro-4-(trifluoromethyl)-2-pentene |
| PFBE (or HFC-1549fz) | $CF_3CF_2CF_2CF_2CH=CH_2$ | 3,3,4,4,5,5,6,6,6-nonafluoro-1-hexene (or perfluorobutylethylene) |
| HFC-1549fztmm | $CH_2=CHC(CF_3)_3$ | 4,4,4-trifluoro-3,3-bis(trifluoromethyl)-1-butene |
| HFC-1549mmtts | $(CF_3)_2C=C(CH_3)(CF_3)$ | 1,1,1,4,4,4-hexafluoro-3-methyl-2-(trifluoromethyl)-2-butene |
| HFC-1549fycz | $CH_2=CFCF_2CH(CF_3)_2$ | 2,3,3,5,5,5-hexafluoro-4-(trifluoromethyl)-1-pentene |
| HFC-1549myts | $CF_3CF=C(CH_3)CF_2CF_3$ | 1,1,1,2,4,4,5,5,5-nonafluoro-3-methyl-2-pentene |
| HFC-1549mzzz | $CF_3CH=CHCH(CF_3)_2$ | 1,1,1,5,5,5-hexafluoro-4-(trifluoromethyl)-2-pentene |
| HFC-1558szy | $CF_3CF_2CF_2CF=CHCH_3$ | 3,4,4,5,5,6,6,6-octafluoro-2-hexene |
| HFC-1558fzccc | $CH_2=CHCF_2CF_2CF_2CHF_2$ | 3,3,4,4,5,5,6,6-octafluoro-2-hexene |
| HFC-1558mmtzc | $(CF_3)_2C=CHCF_2CH_3$ | 1,1,1,4,4-pentafluoro-2-(trifluoromethyl)-2-pentene |
| HFC-1558ftmf | $CH_2=C(CF_3)CH_2C_2F_5$ | 4,4,5,5,5-pentafluoro-2-(trifluoromethyl)-1-pentene |
| HFC-1567fts | $CF_3CF_2CF_2C(CH_3)=CH_2$ | 3,3,4,4,5,5,5-heptafluoro-2-methyl-1-pentene |
| HFC-1567szz | $CF_3CF_2CF_2CH=CHCH_3$ | 4,4,5,5,6,6,6-heptafluoro-2-hexene |
| HFC-1567fzfc | $CH_2=CHCH_2CF_2C_2F_5$ | 4,4,5,5,6,6,6-heptafluoro-1-hexene |
| HFC-1567sfyy | $CF_3CF_2CF=CFC_2H_5$ | 1,1,1,2,2,3,4-heptafluoro-3-hexene |
| HFC-1567fzfy | $CH_2=CHCH_2CF(CF_3)_2$ | 4,5,5,5-tetrafluoro-4-(trifluoromethyl)-1-pentene |
| HFC-1567myzzm | $CF_3CF=CHCH(CF_3)(CH_3)$ | 1,1,1,2,5,5,5-heptafluoro-4-methyl-2-pentene |
| HFC-1567mmtyf | $(CF_3)_2C=CFC_2H_5$ | 1,1,1,3-tetrafluoro-2-(trifluoromethyl)-2-pentene |
| FC-161-14myy | $CF_3CF=CFCF_2CF_2C_2F_5$ | 1,1,1,2,3,4,4,5,5,6,6,7,7,7-tetradecafluoro-2-heptene |
| FC-161-14mcyy | $CF_3CF_2CF=CFCF_2C_2F_5$ | 1,1,1,2,2,3,4,5,5,6,6,7,7,7-tetradecafluoro-2-heptene |
| HFC-162-13mzy | $CF_3CH=CFCF_2CF_2C_2F_5$ | 1,1,1,3,4,4,5,5,6,6,7,7,7-tridecafluoro-2-heptene |
| HFC162-13myz | $CF_3CF=CHCF_2CF_2C_2F_5$ | 1,1,1,2,4,4,5,5,6,6,7,7,7-tridecafluoro-2-heptene |
| HFC-162-13mczy | $CF_3CF_2CH=CFCF_2C_2F_5$ | 1,1,1,2,2,4,5,5,6,6,7,7,7-tridecafluoro-3-heptene |
| HFC-162-13mcyz | $CF_3CF_2CF=CHCF_2C_2F_5$ | 1,1,1,2,2,3,5,5,6,6,7,7,7-tridecafluoro-3-heptene |
| PEVE | $CF_2=CFOCF_2CF_3$ | pentafluoroethyl trifluorovinyl ether |
| PMVE | $CF_2=CFOCF_3$ | trifluoromethyl trifluorovinyl ether |

The compounds listed in Table 2 and Table 3 are available commercially or may be prepared by processes known in the art or as described herein.

1,1,1,4,4-pentafluoro-2-butene may be prepared from 1,1,1,2,4,4-hexafluorobutane ($CHF_2CH_2CHFCF_3$) by dehydrofluorination over solid KOH in the vapor phase at room temperature. The synthesis of 1,1,1,2,4,4-hexafluorobutane is described in U.S. Pat. No. 6,066,768, incorporated herein by reference.

1,1,1,4,4,4-hexafluoro-2-butene may be prepared from 1,1,1,4,4,4-hexafluoro-2-iodobutane ($CF_3CHICH_2CF_3$) by reaction with KOH using a phase transfer catalyst at about 60° C. The synthesis of 1,1,1,4,4,4-hexafluoro-2-iodobutane may be carried out by reaction of perfluoromethyl iodide ($CF_3I$) and 3,3,3-trifluoropropene ($CF_3CH=CH_2$) at about 200° C. under autogenous pressure for about 8 hours.

3,4,4,5,5,5-hexafluoro-2-pentene may be prepared by dehydrofluorination of 1,1,1,2,2,3,3-heptafluoropentane ($CF_3CF_2CF_2CH_2CH_3$) using solid KOH or over a carbon catalyst at 200-300° C. 1,1,1,2,2,3,3-heptafluoropentane may be prepared by hydrogenation of 3,3,4,4,5,5,5-heptafluoro-1-pentene ($CF_3CF_2CF_2CH=CH_2$).

1,1,1,2,3,4-hexafluoro-2-butene may be prepared by dehydrofluorination of 1,1,1,2,3,3,4-heptafluorobutane ($CH_2FCF_2CHFCF_3$) using solid KOH.

1,1,1,2,4,4-hexafluoro-2-butene may be prepared by dehydrofluorination of 1,1,1,2,2,4,4-heptafluorobutane ($CHF_2CH_2CF_2CF_3$) using solid KOH.

1,1,1,3,4,4-hexafluoro2-butene may be prepared by dehydrofluorination of 1,1,1,3,3,4,4-heptafluorobutane ($CF_3CH_2CF_2CHF_2$) using solid KOH.

1,1,1,2,4-pentafluoro-2-butene may be prepared by dehydrofluorination of 1,1,1,2,2,3-hexafluorobutane ($CH_2FCHCF_2CF_3$) using solid KOH.

1,1,1,3,4-pentafluoro-2-butene may be prepared by dehydrofluorination of 1,1,1,3,3,4-hexafluorobutane ($CF_3CH_2CF_2CH_2F$) using solid KOH.

1,1,1,3-tetrafluoro-2-butene may be prepared by reacting 1,1,1,3,3-pentafluorobutane ($CF_3CH_2CF_2CH_3$) with aqueous KOH at 120° C.

1,1,1,4,4,5,5,5-octafluoro-2-pentene may be prepared from ($CF_3CHICH_2CF_2CF_3$) by reaction with KOH using a phase transfer catalyst at about 60° C. The synthesis of 4-iodo-1,1,1,2,2,5,5,5-octafluoropentane may be carried out by reaction of perfluoroethyliodide ($CF_3CF_2I$) and 3,3,3-trifluoropropene at about 200° C. under autogenous pressure for about 8 hours.

1,1,1,2,2,5,5,6,6,6-decafluoro-3-hexene may be prepared from 1,1,1,2,2,5,5,6,6,6-decafluoro-3-iodohexane ($CF_3CF_2CHICH_2CF_2CF_3$) by reaction with KOH using a phase transfer catalyst at about 60° C. The synthesis of 1,1,1,2,2,5,5,6,6,6-decafluoro-3-iodohexane may be carried out by reaction of perfluoroethyliodide ($CF_3CF_2I$) and 3,3,4,4,4-pentafluoro-1-butene ($CF_3CF_2CH=CH_2$) at about 200° C. under autogenous pressure for about 8 hours.

1,1,1,4,5,5,5-heptafluoro-4-(trifluoromethyl)-2-pentene may be prepared by the dehydrofluorination of 1,1,1,2,5,5,5-heptafluoro-4-iodo-2-(trifluoromethyl)-pentane ($CF_3CHICH_2CF(CF_3)_2$) with KOH in isopropanol. $CF_3CHICH_2CF(CF_3)_2$ is made from reaction of $(CF_3)_2CFI$ with $CF_3CH=CH_2$ at high temperature, such as about 200° C.

1,1,1,4,4,5,5,6,6,6-decafluoro-2-hexene may be prepared by the reaction of 1,1,1,4,4,4-hexafluoro-2-butene ($CF_3CH=CHCF_3$) with tetrafluoroethylene ($CF_2=CF_2$) and antimony pentafluoride ($SbF_5$).

2,3,3,4,4-pentafluoro-1-butene may be prepared by dehydrofluorination of 1,1,2,2,3,3-hexafluorobutane over fluorided alumina at elevated temperature.

2,3,3,4,4,5,5,5-ocatafluoro-1-pentene may be prepared by dehydrofluorination of 2,2,3,3,4,4,5,5,5-nonafluoropentane over solid KOH.

1,2,3,3,4,4,5,5-octafluoro-1-pentene may be prepared by dehydrofluorination of 2,2,3,3,4,4,5,5,5-nonafluoropentane over fluorided alumina at elevated temperature.

The compositions of the present invention may comprise a single compound of Formula I, Formula II, or Table 3 or may comprise a combination of said compounds. Additionally, many of the compounds of Formula I, Formula II, and Table 3 may exist as different configurational isomers or stereoisomers. The present invention is intended to include all single configurational isomers, single stereoisomers or any combination thereof. For instance, 1,3,3,3-tetrafluoropropene (HFC-1234ze) is meant to represent the E-isomer, Z-isomer, or any combination or mixture of both isomers in any ratio. Another example is F12E, by which is represented the E-isomer, Z-isomer, or any combination or mixture of both isomers in any ratio.

Compositions of the present invention have zero or low ozone depletion potential and low global warming potential (GWP). The fluoroolefins of the present invention or mixtures of fluoroolefins of this invention with other refrigerants will have global warming potentials that are less than many hydrofluorocarbon refrigerants currently in use. One aspect of the present invention is to provide a refrigerant with a global warming potential of less than 1000, less than 500, less than 150, less than 100, or less than 50. Another aspect of the present invention is to reduce the net GWP of refrigerant mixtures by adding fluoroolefins to said mixtures.

The compositions of the present invention that are combinations or mixtures may be prepared by any convenient method to combine the desired amounts of the individual components. A preferred method is to weigh the desired component amounts and thereafter combine the components in an appropriate vessel. Agitation may be used, if desired.

An alternative means for making compositions of the present invention comprises (i) reclaiming a volume of one or more components of a refrigerant composition from at least one refrigerant container, (ii) removing impurities sufficiently to enable reuse of said one or more of the reclaimed components, (iii) and optionally, combining all or part of said reclaimed volume of components with at least one additional refrigerant composition or component.

A refrigerant container may be any container in which is stored a refrigerant blend composition that has been used in a refrigeration apparatus, air-conditioning apparatus or heat pump apparatus. Said refrigerant container may be the refrigeration apparatus, air-conditioning apparatus or heat pump apparatus in which the refrigerant blend was used. Additionally, the refrigerant container may be a storage container for collecting reclaimed refrigerant blend components, including but not limited to pressurized gas cylinders.

Residual refrigerant means any amount of refrigerant blend or refrigerant blend component that may be moved out of the refrigerant container by any method known for transferring refrigerant blends or refrigerant blend components.

Impurities may be any component that is in the refrigerant blend or refrigerant blend component due to its use in a refrigeration apparatus, air-conditioning apparatus or heat pump apparatus. Such impurities include but are not limited to refrigeration lubricants, being those described earlier herein, particulates such as metal or elastomer that may have come out of the refrigeration apparatus, air-conditioning apparatus or heat pump apparatus, and any other contaminants that may adversely effect the performance of the refrigerant blend composition.

Such impurities may be removed sufficiently to allow reuse of the refrigerant blend or refrigerant blend component without adversely effecting the performance or equipment within which the refrigerant blend or refrigerant blend component will be used.

It may be necessary to provide additional refrigerant blend or refrigerant blend component to the residual refrigerant blend or refrigerant blend component in order to produce a composition that meets the specifications required for a given product. For instance, if a refrigerant blend has 3 components in a particular weight percentage range, it may be necessary to add one or more of the components in a given amount in order to restore the composition to within the specification limits.

The compositions of the present invention that are useful as refrigerants or heat transfer fluids comprise at least one fluoroolefin selected from the group consisting of:

(i) fluoroolefins of the formula E- or Z—$R^1CH=CHR^2$, wherein $R^1$ and $R^2$ are, independently, $C_1$ to $C_6$ perfluoroalkyl groups, and wherein the total number of carbons in the compound is at least 5;

(ii) cyclic fluoroolefins of the formula cyclo-[CX=CY (CZW)$_n$—], wherein X, Y, Z, and W, independently, are H or F, and n is an integer from 2 to 5; and (iii) fluoroolefins selected from the group consisting of: 1,2,3,3,3-pentafluoro-1-propene ($CF_3CF=CHF$); 1,1,3,3,3-pentafluoro-1-propene ($CF_3CH=CF_2$); 1,1,2,3,3-pentafluoro-1-propene ($CHF_2CF=CF_2$); 1,2,3,3-tetrafluoro-1-propene ($CHF_2CF=CHF$); 2,3,3,3-tetrafluoro-1-propene ($CF_3CF=CH_2$); 1,1,2,3-tetrafluoro-1-propene ($CH_2FCF=CF_2$); 1,1,3,3-tetrafluoro-1-propene ($CHF_2CH=CF_2$); 2,3,3-trifluoro-1-propene ($CHF_2CF=CH_2$); 3,3,3-trifluoro-1-propene ($CF_3CH=CH_2$); 1,1,2-trifluoro-1-propene ($CH_3CF=CF_2$); 1,2,3-trifluoro-1-propene (CH₂FCF=CF₂); 1,1,3-trifluoro-1-propene (CH₂FCH=CF₂); 1,3,3-trifluoro-1-propene (CHF₂CH=CHF); 1,1,1,2,3,4,4,4-octafluoro-2-butene (CF₃CF=CFCF₃); 1,1,2,3,3,4,4,4-octafluoro-1-butene (CF₃CF₂CF=CF₂); 1,1,1,2,4,4,4-heptafluoro-2-butene (CF₃CF=CHCF₃); 1,2,3,3,4,4,4-heptafluoro-1-butene (CHF=CFCF₂CF₃); 1,1,1,2,3,4,4-heptafluoro-2-butene (CHF₂CF=CFCF₃); 1,3,3,3-tetrafluoro-2-(trifluoromethyl)-1-propene ((CF₃)₂C=CHF); 1,1,3,3,4,4-heptafluoro-1-butene (CF₂=CHCF₂CF₃); 1,1,2,3,4,4,4-heptafluoro-1-butene (CF₂=CFCHFCF₃); 1,1,2,3,3,4,4-heptafluoro-1-butene (CF₂=CFCF₂CHF₂); 2,3,3,4,4,4-hexafluoro-1-butene (CF₃CF₂CF=CH₂); 1,3,3,4,4,4-hexafluoro-1-butene (CHF=CHCF₂CF₃); 1,2,3,4,4,4-hexafluoro-1-butene (CHF=CFCHFCF₃); 1,2,3,3,4,4-hexafluoro-1-butene (CHF=CFCF₂CHF₂); 1,1,2,3,4,4-hexafluoro-2-butene (CHF₂CF=CFCHF₂); 1,1,1,2,3,4-hexafluoro-2-butene (CH₂FCF=CFCF₃); 1,1,1,2,4,4-hexafluoro-2-butene (CH₂FCH=CFCF₃); 1,1,1,3,4,4-hexafluoro-2-butene (CF₃CH=CFCHF₂); 1,1,2,3,3,4-hexafluoro-1-butene (CF₂=CFCF₂CH₂F); 1,1,2,3,4,4-hexafluoro-1-butene (CF₂=CFCHFCHF₂); 3,3,3-trifluoro-2-(trifluoromethyl)-1-propene (CH₂=C(CF₃)₂); 1,1,1,2,4-pentafluoro-2-butene (CH₂FCH=CFCF₃); 1,1,1,3,4-pentafluoro-2-butene (CF₃CH=CFCH₂F); 3,3,4,4,4-pentafluoro-1-butene (CF₃CF₂CH=CH₂); 1,1,1,4-pentafluoro-2-butene (CHF₂CH=CHCF₃); 1,1,1,2,3-pentafluoro-2-butene (CH₃CF=CFCF₃); 2,3,3,4,4-pentafluoro-1-butene (CH₂=CFCF₂CHF₂); 1,1,2,4-pentafluoro-2-butene (CHF₂CF=CHCHF₂); 1,1,2,3,3-pentafluoro-1-butene (CH₃CF₂CF=CF₂); 1,1,2,3,4-pentafluoro-2-butene (CH₂FCF=CFCHF₂); 1,1,3,3,3-pentafluoro-2-methyl-1-propene (CF₂=C(CF₃)(CH₃)); 2-(difluoromethyl)-3,3,3-trifluoro-1-propene (CH₂=C(CHF₂)(CF₃)); 2,3,4,4,4-pentafluoro-1-butene (CH₂=CFCHFCF₃); 1,2,4,4,4-pentafluoro-1-butene (CHF=CFCH₂CF₃); 1,3,4,4,4-pentafluoro-1-butene (CHF=CHCHFCF₃); 1,3,3,4,4-pentafluoro-1-butene (CHF=CHCF₂CHF₂); 1,2,3,4,4-pentafluoro-1-butene (CHF=CFCHFCHF₂); 3,3,4,4-tetrafluoro-1-butene (CH₂=CHCF₂CHF₂); 1,1-difluoro-2-(difluoromethyl)-1-propene (CF₂=C(CHF₂)(CH₃)); 1,3,3,3-tetrafluoro-2-methyl-1-propene (CHF=C(CF₃)(CH₃)); 3,3-difluoro-2-(difluoromethyl)-1-propene (CH₂=C(CHF₂)₂); 1,1,1,2-tetrafluoro-2-butene (CF₃CF=CHCH₃); 1,1,1,3-tetrafluoro-2-butene (CH₃CF=CHCF₃); 1,1,1,2,3,4,4,5,5-decafluoro-2-pentene (CF₃CF=CFCF₂CF₃); 1,1,2,3,3,4,4,5,5,5-decafluoro-1-pentene (CF₂=CFCF₂CF₂CF₃); 1,1,1,4,4,4-hexafluoro-2-(trifluoromethyl)-2-butene ((CF₃)₂C=CHCF₃); 1,1,1,2,4,4,5,5,5-nonafluoro-2-pentene (CF₃CF=CHCF₂CF₃); 1,1,1,3,4,4,5,5,5-nonafluoro-2-pentene (CF₃CH=CFCF₂CF₃); 1,2,3,3,4,4,5,5,5-nonafluoro-1-pentene (CHF=CFCF₂CF₂CF₃); 1,1,3,3,4,4,5,5,5-nonafluoro-1-pentene (CF₂=CHCF₂CF₂CF₃); 1,1,2,3,3,4,4,5,5-nonafluoro-1-pentene (CF₂=CFCF₂CF₂CHF₂); 1,1,2,3,4,4,5,5,5-nonafluoro-2-pentene (CHF₂CF=CFCF₂CF₃); 1,1,1,2,3,4,4,5,5-nonafluoro-2-pentene (CF₃CF=CFCF₂CHF₂); 1,1,1,2,3,4,5,5,5-nonafluoro-2-pentene (CF₃CF=CFCHFCF₃); 1,2,3,4,4,4-hexafluoro-3-(trifluoromethyl)-1-butene (CHF=CFCF(CF₃)₂); 1,1,2,4,4,4-hexafluoro-3-(trifluoromethyl)-1-butene (CF₂=CFCH(CF₃)₂); 1,1,1,4,4,4-hexafluoro-2-(trifluoromethyl)-2-butene (CF₃CH=C(CF₃)₂); 1,1,3,4,4,4-hexafluoro-3-(trifluoromethyl)-1-butene (CF₂=CHCF(CF₃)₂); 2,3,3,4,4,5,5,5-octafluoro-1-pentene (CH₂=CFCF₂CF₂CF₃); 1,2,3,3,4,4,5,5-octafluoro-1-pentene (CHF=CFCF₂CF₂CHF₂); 3,3,4,4,4-pentafluoro-2-(trifluoromethyl)-1-butene (CH₂=C(CF₃)CF₂CF₃); 1,1,4,4,4-pentafluoro-3-(trifluoromethyl)-1-butene (CF₂=CHCH(CF₃)₂); 1,3,4,4,4-pentafluoro-3-(trifluoromethyl)-1-butene (CHF=CHCF(CF₃)₂); 1,1,4,4,4-pentafluoro-2-(trifluoromethyl)-1-butene (CF₂=C(CF₃)CH₂CF₃); 3,4,4,4-tetrafluoro-3-(trifluoromethyl)-1-butene ((CF₃)₂CFCH=CH₂); 3,3,4,4,5,5,5-heptafluoro-1-pentene (CF₃CF₂CF₂CH=CH₂); 2,3,3,4,4,5,5-heptafluoro-1-pentene (CH₂=CFCF₂CF₂CHF₂); 1,1,3,3,5,5,5-heptafluoro-1-butene (CF₂=CHCF₂CH₂CF₃); 1,1,1,2,4,4,4-heptafluoro-3-methyl-2-butene (CF₃CF=C(CF₃)(CH₃)); 2,4,4,4-tetrafluoro-3-(trifluoromethyl)-1-butene (CH₂=CFCH(CF₃)₂); 1,4,4,4-tetrafluoro-3-(trifluoromethyl)-1-butene (CHF=CHCH(CF₃)₂); 1,1,1,4-tetrafluoro-2-(trifluoromethyl)-2-butene (CH₂FCH=C(CF₃)₂); 1,1,1,3-tetrafluoro-2-(trifluoromethyl)-2-butene (CH₃CF=C(CF₃)₂); 1,1,1-trifluoro-2-(trifluoromethyl)-2-butene ((CF₃)₂C=CHCH₃); 3,4,4,5,5,5-hexafluoro-2-pentene (CF₃CF₂CF=CHCH₃); 1,1,1,4,4,4-hexafluoro-2-methyl-2-butene (CF₃C(CH₃)=CHCF₃); 3,3,4,5,5,5-hexafluoro-1-pentene (CH₂=CHCF₂CHFCF₃); 4,4,4-trifluoro-3-(trifluoromethyl)-1-butene (CH₂=C(CF₃)CH₂CF₃); 1,1,2,3,3,4,4,5,5,6,6,6-dodecafluoro-1-hexene (CF₃(CF₂)₃CF=CF₂); 1,1,1,2,2,3,4,5,5,6,6,6-dodecafluoro-3-hexene (CF₃CF₂CF=CFCF₂CF₃); 1,1,1,4,4,4-hexafluoro-2,3-bis(trifluoromethyl)-2-butene ((CF₃)₂C=C(CF₃)₂); 1,1,1,2,3,4,5,5,5-nonafluoro-4-(trifluoromethyl)-2-pentene ((CF₃)₂CFCF=CFCF₃); 1,1,1,4,4,5,5,5-octafluoro-2-(trifluoromethyl)-2-pentene ((CF₃)₂C=CHC₂F₅); 1,1,1,3,4,5,5,5-octafluoro-4-(trifluoromethyl)-2-pentene ((CF₃)₂CFCF=CHCF₃); 3,3,4,4,5,5,6,6,6-nonafluoro-1-hexene (CF₃CF₂CF₂CF₂CH=CH₂); 4,4,4-trifluoro-3,3-bis(trifluoromethyl)-1-butene (CH₂=CHC(CF₃)₃); 1,1,1,4,4,4-hexafluoro-2-(trifluoromethyl)-3-methyl-2-butene ((CF₃)₂C=C(CH₃)(CF₃)); 2,3,3,5,5,5-hexafluoro-4-(trifluoromethyl)-1-pentene (CH₂=CFCF₂CH(CF₃)₂); 1,1,1,2,4,4,5,5,5-nonafluoro-3-methyl-2-pentene (CF₃CF=C(CH₃)CF₂CF₃); 1,1,1,5,5,5-hexafluoro-4-(trifluoromethyl)-2-pentene (CF₃CH=CHCH(CF₃)₂); 3,4,4,5,5,6,6,6-octafluoro-2-hexene (CF₃CF₂CF₂CF=CHCH₃); 3,3,4,4,5,5,6,6-octafluoro-1-hexene (CH₂=CHCF₂CF₂CF₂CHF₂); 1,1,1,4,4-pentafluoro-2-(trifluoromethyl)-2-pentene ((CF₃)₂C=CHCF₂CH₃); 4,4,5,5,5-pentafluoro-2-(trifluoromethyl)-1-pentene (CH₂=C(CF₃)CH₂C₂F₅); 3,3,4,4,5,5,5-heptafluoro-2-methyl-1-pentene (CF₃CF₂CF₂C(CH₃)=CH₂); 4,4,5,5,6,6,6-heptafluoro-2-hexene (CF₃CF₂CF₂CH=CHCH₃); 4,4,5,5,6,6,6-heptafluoro-1-hexene (CH₂=CHCH₂CF₂C₂F₅); 1,1,1,2,2,3,4-heptafluoro-3-hexene (CF₃CF₂CF=CFC₂H₅); 4,5,5,5-tetrafluoro-4-(trifluoromethyl)-1-pentene (CH₂=CHCH₂CF(CF₃)₂); 1,1,1,2,5,5,5-heptafluoro-4-methyl-2-pentene (CF₃CF=CHCH(CF₃)(CH₃)); 1,1,1,3-tetrafluoro-2-(trifluoromethyl)-2-pentene ((CF₃)₂C=CFC₂H₅); 1,1,1,2,3,4,4,5,5,6,6,7,7,7-tetradecafluoro-2-heptene (CF₃CF=CFCF₂CF₂C₂F₅); 1,1,1,2,2,3,4,5,5,6,6,7,7,7-tetradecafluoro-3-heptene (CF₃CF₂CF=CFCF₂C₂F₅); 1,1,1,3,4,4,5,5,6,6,7,7,7-tridecafluoro-2-heptene (CF₃CH=CFCF₂CF₂C₂F₅); 1,1,1,2,4,4,5,5,6,6,7,7,7-tridecafluoro-2-heptene ($CF_3CF$=$CHCF_2CF_2C_2F_5$); 1,1,1,2,2,4,5,5,6,6,7,7,7-tridecafluoro-3-heptene ($CF_3CF_2CH$=$CFCF_2C_2F_5$); 1,1,1,2,2,3,5,5,6,6,7,7,7-tridecafluoro-3-heptene ($CF_3CF_2CF$=$CHCF_2C_2F_5$); $CF_2$=$CFOCF_2CF_3$ (PEVE) and $CF_2$=$CFOCF_3$ (PMVE).

The present invention further relates to compositions comprising at least one fluoroolefin and at least one flammable refrigerant or heat transfer fluid, wherein the fluoroolefin is selected from the group consisting of:

(i) fluoroolefins of the formula E- or Z—$R^1CH$=$CHR^2$, wherein $R^1$ and $R^2$ are, independently, $C_1$ to $C_6$ perfluoroalkyl groups, and wherein the total number of carbons in the compound is at least 5;

(ii) cyclic fluoroolefins of the formula cyclo-[$CX$=$CY$($CZW$)$_n$—], wherein X, Y, Z, and W, independently, are H or F, and n is an integer from 2 to 5; and (iii) fluoroolefins selected from the group consisting of: 1,2,3,3,3-pentafluoro-1-propene ($CF_3CF$=$CHF$); 1,1,3,3,3-pentafluoro-1-propene ($CF_3CH$=$CF_2$); 1,1,2,3,3-pentafluoro-1-propene ($CHF_2CF$=$CF_2$); 1,2,3,3-tetrafluoro-1-propene ($CHF_2CF$=$CHF$); 2,3,3,3-tetrafluoro-1-propene ($CF_3CF$=$CH_2$); 1,1,2,3-tetrafluoro-1-propene ($CH_2FCF$=$CF_2$); 1,1,3,3-tetrafluoro-1-propene ($CHF_2CH$=$CF_2$); 2,3,3-trifluoro-1-propene ($CHF_2CF$=$CH_2$); 3,3,3-trifluoro-1-propene ($CF_3CH$=$CH_2$); 1,1,2-trifluoro-1-propene ($CH_3CF$=$CF_2$); 1,2,3-trifluoro-1-propene ($CH_2FCF$=$CF_2$); 1,1,3-trifluoro-1-propene ($CH_2FCH$=$CF_2$); 1,3,3-trifluoro-1-propene ($CHF_2CH$=$CHF$); 1,1,1,2,3,4,4,4-octafluoro-2-butene ($CF_3CF$=$CFCF_3$); 1,1,2,3,3,4,4,4-octafluoro-1-butene ($CF_3CF_2CF$=$CF_2$); 1,1,1,2,4,4,4-heptafluoro-2-butene ($CF_3CF$=$CHCF_3$); 1,2,3,3,4,4,4-heptafluoro-1-butene ($CHF$=$CFCF_2CF_3$); 1,1,1,2,3,4,4-heptafluoro-2-butene ($CHF_2CF$=$CFCF_3$); 1,3,3,3-tetrafluoro-2-(trifluoromethyl)-1-propene (($CF_3$)$_2C$=$CHF$); 1,1,3,3,4,4,4-heptafluoro-1-butene ($CF_2$=$CHCF_2CF_3$); 1,1,2,3,4,4,4-heptafluoro-1-butene ($CF_2$=$CFCHFCF_3$); 1,1,2,3,3,4,4-heptafluoro-1-butene ($CF_2$=$CFCF_2CHF_2$); 2,3,3,4,4,4-hexafluoro-1-butene ($CF_3CF_2CF$=$CH_2$); 1,3,3,4,4,4-hexafluoro-1-butene ($CHF$=$CHCF_2CF_3$); 1,2,3,4,4,4-hexafluoro-1-butene ($CHF$=$CFCHFCF_3$); 1,2,3,3,4,4-hexafluoro-1-butene ($CHF$=$CFCF_2CHF_2$); 1,1,2,3,4,4-hexafluoro-2-butene ($CHF_2CF$=$CFCHF_2$); 1,1,1,2,3,4-hexafluoro-2-butene ($CH_2FCF$=$CFCF_3$); 1,1,1,2,4,4-hexafluoro-2-butene ($CHF_2CH$=$CFCF_3$); 1,1,1,3,4,4-hexafluoro-2-butene ($CF_3CH$=$CFCHF_2$); 1,1,2,3,3,4-hexafluoro-1-butene ($CF_2$=$CFCF_2CH_2F$); 1,1,2,3,4,4-hexafluoro-1-butene ($CF_2$=$CFCHFCHF_2$); 3,3,3-trifluoro-2-(trifluoromethyl)-1-propene ($CH_2$=$C(CF_3)_2$); 1,1,1,2,4-pentafluoro-2-butene ($CH_2FCH$=$CFCF_3$); 1,1,1,3,4-pentafluoro-2-butene ($CF_3CH$=$CFCH_2F$); 3,3,4,4,4-pentafluoro-1-butene ($CF_3CF_2CH$=$CH_2$); 1,1,1,4,4-pentafluoro-2-butene ($CHF_2CH$=$CHCF_3$); 1,1,1,2,3-pentafluoro-2-butene ($CH_3CF$=$CFCF_3$); 2,3,3,4,4-pentafluoro-1-butene ($CH_2$=$CFCF_2CHF_2$); 1,1,2,4,4-pentafluoro-2-butene ($CHF_2CF$=$CHCHF_2$); 1,1,2,3,3-pentafluoro-1-butene ($CH_3CF_2CF$=$CF_2$); 1,1,2,3,4-pentafluoro-2-butene ($CH_2FCF$=$CFCHF_2$); 1,1,3,3,3-pentafluoro-2-methyl-1-propene ($CF_2$=$C(CF_3)(CH_3)$); 2-(difluoromethyl)-3,3,3-trifluoro-1-propene ($CH_2$=$C(CHF_2)(CF_3)$); 2,3,4,4,4-pentafluoro-1-butene ($CH_2$=$CFCHFCF_3$); 1,2,4,4,4-pentafluoro-1-butene ($CHF$=$CFCH_2CF_3$); 1,3,4,4,4-pentafluoro-1-butene ($CHF$=$CHCHFCF_3$); 1,3,3,4,4-pentafluoro-1-butene ($CHF$=$CHCF_2CHF_2$); 1,2,3,4,4-pentafluoro-1-butene ($CHF$=$CFCHFCHF_2$); 3,3,4,4-tetrafluoro-1-butene ($CH_2$=$CHCF_2CHF_2$); 1,1-difluoro-2-(difluoromethyl)-1-propene ($CF_2$=$C(CHF_2)(CH_3)$); 1,3,3,3-tetrafluoro-2-methyl-1-propene ($CHF$=$C(CF_3)(CH_3)$); 3,3-difluoro-2-(difluoromethyl)-1-propene ($CH_2$=$C(CHF_2)_2$); 1,1,1,2-tetrafluoro-2-butene ($CF_3CF$=$CHCH_3$); 1,1,1,3-tetrafluoro-2-butene ($CH_3CF$=$CHCF_3$); 1,1,1,2,3,4,4,5,5-decafluoro-2-pentene ($CF_3CF$=$CFCF_2CF_3$); 1,1,2,3,3,4,4,5,5,5-decafluoro-1-pentene ($CF_2$=$CFCF_2CF_2CF_3$); 1,1,1,4,4,4-hexafluoro-2-(trifluoromethyl)-2-butene (($CF_3$)$_2C$=$CHCF_3$); 1,1,1,2,4,4,5,5,5-nonafluoro-2-pentene ($CF_3CF$=$CHCF_2CF_3$); 1,1,1,3,4,4,5,5,5-nonafluoro-2-pentene ($CF_3CH$=$CFCF_2CF_3$); 1,2,3,3,4,4,5,5,5-nonafluoro-1-pentene ($CHF$=$CFCF_2CF_2CF_3$); 1,1,3,3,4,4,5,5,5-nonafluoro-1-pentene ($CF_2$=$CHCF_2CF_2CF_3$); 1,1,2,3,3,4,4,5,5-nonafluoro-1-pentene ($CF_2$=$CFCF_2CF_2CHF_2$); 1,1,2,3,4,4,5,5,5-nonafluoro-2-pentene ($CHF_2CF$=$CFCF_2CF_3$); 1,1,1,2,3,4,4,5,5-nonafluoro-2-pentene ($CF_3CF$=$CFCF_2CHF_2$); 1,1,1,2,3,4,5,5,5-nonafluoro-2-pentene ($CF_3CF$=$CFCHFCF_3$); 1,2,3,4,4,4-hexafluoro-3-(trifluoromethyl)-1-butene ($CHF$=$CFCF(CF_3)_2$); 1,1,2,4,4,4-hexafluoro-3-(trifluoromethyl)-1-butene ($CF_2$=$CFCH(CF_3)_2$); 1,1,1,4,4,4-hexafluoro-2-(trifluoromethyl)-2-butene ($CF_3CH$=$C(CF_3)_2$); 1,1,3,4,4,4-hexafluoro-3-(trifluoromethyl)-1-butene ($CF_2$=$CHCF(CF_3)_2$); 2,3,3,4,4,5,5,5-octafluoro-1-pentene ($CH_2$=$CFCF_2CF_2CF_3$); 1,2,3,3,4,4,5,5-octafluoro-1-pentene ($CHF$=$CFCF_2CF_2CHF_2$); 3,3,4,4,4-pentafluoro-2-(trifluoromethyl)-1-butene ($CH_2$=$C(CF_3)CF_2CF_3$); 1,1,4,4,4-pentafluoro-3-(trifluoromethyl)-1-butene ($CF_2$=$CHCH(CF_3)_2$); 1,3,4,4,4-pentafluoro-3-(trifluoromethyl)-1-butene ($CHF$=$CHCF(CF_3)_2$); 1,1,4,4,4-pentafluoro-2-(trifluoromethyl)-1-butene ($CF_2$=$C(CF_3)CH_2CF_3$); 3,4,4,4-tetrafluoro-3-(trifluoromethyl)-1-butene (($CF_3$)$_2CFCH$=$CH_2$); 3,3,4,4,5,5,5-heptafluoro-1-pentene ($CF_3CF_2CF_2CH$=$CH_2$); 2,3,3,4,4,5,5-heptafluoro-1-pentene ($CH_2$=$CFCF_2CF_2CHF_2$); 1,1,3,3,5,5,5-heptafluoro-1-butene ($CF_2$=$CHCF_2CH_2CF_3$); 1,1,1,2,4,4,4-heptafluoro-3-methyl-2-butene ($CF_3CF$=$C(CF_3)(CH_3)$); 2,4,4,4-tetrafluoro-3-(trifluoromethyl)-1-butene ($CH_2$=$CFCH(CF_3)_2$); 1,4,4,4-tetrafluoro-3-(trifluoromethyl)-1-butene ($CHF$=$CHCH(CF_3)_2$); 1,1,1,4-tetrafluoro-2-(trifluoromethyl)-2-butene ($CH_2FCH$=$C(CF_3)_2$); 1,1,1,3-tetrafluoro-2-(trifluoromethyl)-2-butene ($CH_3CF$=$C(CF_3)_2$); 1,1,1-trifluoro-2-(trifluoromethyl)-2-butene (($CF_3$)$_2C$=$CHCH_3$); 3,4,4,5,5,5-hexafluoro-2-pentene ($CF_3CF_2CF$=$CHCH_3$); 1,1,1,4,4,4-hexafluoro-2-methyl-2-butene ($CF_3C(CH_3)$=$CHCF_3$); 3,3,4,5,5,5-hexafluoro-1-pentene ($CH_2$=$CHCF_2CHFCF_3$); 4,4,4-trifluoro-3-(trifluoromethyl)-1-butene ($CH_2$=$C(CF_3)CH_2CF_3$); 1,1,2,3,3,4,4,5,5,6,6,6-dodecafluoro-1-hexene ($CF_3(CF_2)_3CF$=$CF_2$); 1,1,1,2,2,3,4,5,5,6,6,6-dodecafluoro-3-hexene ($CF_3CF_2CF$=$CFCF_2CF_3$); 1,1,1,4,4,4-hexafluoro-2,3-bis(trifluoromethyl)-2-butene (($CF_3$)$_2C$=$C(CF_3)_2$); 1,1,1,2,3,4,5,5,5-nonafluoro-4-(trifluoromethyl)-2-pentene (($CF_3$)$_2CFCF$=$CFCF_3$); 1,1,1,4,4,5,5,5-octafluoro-2-(trifluoromethyl)-2-pentene (($CF_3$)$_2C$=$CHC_2F_5$); 1,1,1,3,4,5,5,5-octafluoro-4-(trifluoromethyl)-2-pentene (($CF_3$)$_2CFCF$=$CHCF_3$); 3,3,4,4,5,5,6,6,6-nonafluoro-1-hexene ($CF_3(CF_2)_3CF_2CH$=$CH_2$); 4,4,4-trifluoro-3,3-bis(trifluoromethyl)-1-butene ($CH_2$=$CHC(CF_3)_3$); 1,1,1,4,4,4-hexafluoro-2-(trifluoromethyl)-3-methyl-2- butene ((CF$_3$)$_2$C=C(CH$_3$)(CF$_3$)); 2,3,3,5,5,5-hexafluoro-4-(trifluoromethyl)-1-pentene (CH$_2$=CFCF$_2$CH(CF$_3$)$_2$); 1,1,1,2,4,4,5,5,5-nonafluoro-3-methyl-2-pentene (CF$_3$CF=C(CH$_3$)CF$_2$CF$_3$); 1,1,1,5,5,5-hexafluoro-4-(trifluoromethyl)-2-pentene (CF$_3$CH=CHCH(CF$_3$)$_2$); 3,4,4,5,5,6,6,6-octafluoro-2-hexene (CF$_3$CF$_2$CF$_2$CF=CHCH$_3$); 3,3,4,4,5,5,6,6-octafluoro1-hexene (CH$_2$=CHCF$_2$CF$_2$CF$_2$CHF$_2$); 1,1,1,4,4-pentafluoro-2-(trifluoromethyl)-2-pentene ((CF$_3$)$_2$C=CHCF$_2$CH$_3$); 4,4,5,5,5-pentafluoro-2-(trifluoromethyl)-1-pentene (CH$_2$=C(CF$_3$)CH$_2$C$_2$F$_5$); 3,3,4,4,5,5,5-heptafluoro-2-methyl-1-pentene (CF$_3$CF$_2$CF$_2$C(CH$_3$)=CH$_2$); 4,4,5,5,6,6,6-heptafluoro-2-hexene (CF$_3$CF$_2$CF$_2$CH=CHCH$_3$); 4,4,5,5,6,6,6-heptafluoro-1-hexene (CH$_2$=CHCH$_2$CF$_2$C$_2$F$_5$); 1,1,1,2,2,3,4-heptafluoro-3-hexene (CF$_3$CF$_2$CF=CFC$_2$H$_5$); 4,5,5,5-tetrafluoro-4-(trifluoromethyl)-1-pentene (CH$_2$=CHCH$_2$CF(CF$_3$)$_2$); 1,1,1,2,5,5,5-heptafluoro-4-methyl-2-pentene (CF$_3$CF=CHCH(CF$_3$)(CH$_3$)); 1,1,1,3-tetrafluoro-2-(trifluoromethyl)-2-pentene ((CF$_3$)$_2$C=CFC$_2$H$_5$); 1,1,1,2,3,4,4,5,5,6,6,7,7,7-tetradecafluoro-2-heptene (CF$_3$CF=CFCF$_2$CF$_2$C$_2$F$_5$); 1,1,1,2,2,3,4,5,5,6,6,7,7,7-tetradecafluoro-3-heptene (CF$_3$CF$_2$CF=CFCF$_2$C$_2$F$_5$); 1,1,1,3,4,4,5,5,6,6,7,7,7-tridecafluoro-2-heptene (CF$_3$CH=CFCF$_2$CF$_2$C$_2$F$_5$); 1,1,1,2,4,4,5,5,6,6,7,7,7-tridecafluoro-2-heptene (CF$_3$CF=CHCF$_2$CF$_2$C$_2$F$_5$); 1,1,1,2,2,4,5,5,6,6,7,7,7-tridecafluoro-3-heptene (CF$_3$CF$_2$CH=CFCF$_2$C$_2$F$_5$); 1,1,1,2,2,3,5,5,6,6,7,7,7-tridecafluoro-3-heptene (CF$_3$CF$_2$CF=CHCF$_2$C$_2$F$_5$); CF$_2$=CFOCF$_2$CF$_3$ (PEVE) and CF$_2$=CFOCF$_3$ (PMVE).

Of particular utility in compositions comprising at least one flammable refrigerant and at least one fluoroolefin are those fluoroolefins that themselves are non-flammable. Flammability of a fluoroolefin appears to be related to the numbers of fluorine atoms and the numbers of hydrogen atoms in the molecule. The equation below provides a flammability factor that may be calculated as an indication of predicted flammability:

$$\text{flammability factor} = \frac{F}{(F+H)}$$

wherein:
F = the number of fluorine atoms; and
H = the number of hydrogen atoms in a molecule.

As certain compounds have been experimentally determined to be flammable, the cut-off for non-flammable fluoroolefin flammability factors has been determined. Fluoroolefins may be determined to be flammable or non-flammable by testing under conditions specified by ASHRAE (American Society of Heating, Refrigerating and Air-Conditioning Engineers, Inc.) Standard 34-2001, under ASTM (American Society of Testing and Materials) E681-01, with an electronic ignition source. Such tests of flammability are conducted with the compound of interest at 101 kPa (14.7 psia) and a specified temperature (often 100° C. (212° F.)) at various concentrations in air in order to determine the lower flammability limit (LFL) and/or upper flammability limit (UFL) of the test compound in air.

The flammability factors for several fluoroolefins are listed in Table 4 along with the experimental determination of flammable or non-flammable. Therefore, it can be predicted for the other fluoroolefins of the present disclosure, which will be most useful in combination with the flammable refrigerants of the present disclosure as being in fact non-flammable fluoroolefins.

TABLE 4

| Compound | Formula | #F | #H | F/(F + H) | Experimental Flammability (LFL, vol % in air) | Prediction from flammability factor |
|---|---|---|---|---|---|---|
| HFC-1225ye | C$_3$HF$_5$ | 5 | 1 | 0.83 | non-flammable | non-flammable |
| HFC-1234yf | C$_3$H$_2$F$_4$ | 4 | 2 | 0.67 | 6.0 | flammable |
| E-HFC-1234ze | C$_3$H$_2$F$_4$ | 4 | 2 | 0.67 | 5.0 | flammable |
| HFC-1429myz/mzy (mixture of isomers) | C$_5$HF$_9$ | 9 | 1 | 0.90 | non-flammable | non-flammable |
| F12E | C$_6$H$_2$F$_8$ | 8 | 2 | 0.75 | non-flammable | non-flammable |
| Other fluoroolefins | | | | | | |
| HFC-1243 | C$_3$H$_3$F$_3$ | 3 | 3 | 0.15 | na | Flammable |
| FC-1318 | C$_4$F$_8$ | 8 | 0 | 1.0 | na | non-flammable |
| HFC-1327 | C$_4$HF$_7$ | 7 | 1 | 0.88 | na | non-flammable |
| HFC-1336 | C$_4$H$_2$F$_6$ | 6 | 2 | 0.75 | na | non-flammable |
| HFC-1345 | C$_4$H$_3$F$_5$ | 5 | 3 | 0.63 | na | flammable |
| HFC-1354 | C$_4$H$_4$F$_4$ | 4 | 4 | 0.50 | na | flammable |
| FC-141-10 | C$_5$F$_{10}$ | 10 | 0 | 1.0 | na | non-flammable |
| HFC-1429 | C$_5$HF$_9$ | 9 | 1 | 0.90 | na | non-flammable |
| HFC-1438 | C$_5$H$_2$F$_8$ | 8 | 2 | 0.80 | na | non-flammable |
| HFC-1447 | C$_5$H$_3$F$_7$ | 7 | 3 | 0.70 | na | non-flammable |
| HFC-1456 | C$_5$H$_4$F$_6$ | 6 | 4 | 0.6 | na | flammable |
| FC-151-12 | C$_6$F$_{12}$ | 12 | 0 | 1.0 | na | non-flammable |
| HFC-152-11 | C$_6$HF$_{11}$ | 11 | 1 | 0.92 | na | non-flammable |
| HFC-153-10 | C$_6$H$_2$F$_{10}$ | 10 | 2 | 0.83 | na | non-flammable |
| HFC-1549 | C$_6$H$_3$F$_9$ | 9 | 3 | 0.75 | na | non-flammable |
| HFC-1558 | C$_6$H$_4$F$_8$ | 8 | 4 | 0.67 | na | flammable |
| HFC-1567 | C$_6$H$_5$F$_7$ | 7 | 5 | 0.58 | na | flammable |
| FC-161-14 | C$_7$F$_{14}$ | 14 | 0 | 1.0 | na | non-flammable |
| HFC-162-13 | C$_7$HF$_{13}$ | 13 | 1 | 0.93 | na | non-flammable |

TABLE 4-continued

| | Formula | #F | #H | F/(F + H) | Experimental Flammability (LFL, vol % in air) | Prediction from flammability factor |
|---|---|---|---|---|---|---|
| HFC-163-12 | $C_7H_2F_{12}$ | 12 | 2 | 0.86 | na | non-flammable |
| HFC-164-11 | $C_7H_3F_{11}$ | 11 | 3 | 0.79 | na | non-flammable |
| HFC-165-10 | $C_7H_4F_{10}$ | 10 | 4 | 0.71 | na | non-flammable |
| HFC-1669 | $C_7H_5F_9$ | 9 | 5 | 0.64 | na | flammable |
| HFC-C1316 | $C_4F_6$ | 6 | 0 | 1.0 | na | non-flammable |
| HFC-C1418 | $C_5F_8$ | 8 | 0 | 1.0 | na | non-flammable |
| HFC-C151-10 | $C_6F_{10}$ | 10 | 0 | 1.0 | na | non-flammable |
| HFC-C1334 | $C_4H_2F_4$ | 4 | 2 | 0.67 | na | flammable |
| HFC-C1436 | $C_5H_2F_6$ | 6 | 2 | 0.75 | na | non-flammable |

The fluoroolefins as listed in Table 4 may be determined to be flammable or non-flammable based upon the value of the flammability factor. If the flammability factor is found to be equal to or greater than 0.70, then the fluoroolefin may be expected to be non-flammable. If the flammability factor is less than 0.70, then the fluoroolefin may be expected to be flammable.

In another embodiment of the present invention, the fluoroolefins for use in compositions with flammable refrigerants are those fluoroolefins selected from the group consisting of:
(a) fluoroolefins of the formula E- or Z—$R^1$CH=CHR$^2$, wherein $R^1$ and $R^2$ are, independently, $C_1$ to $C_6$ perfluoroalkyl groups;
(b) cyclic fluoroolefins of the formula cyclo-[CX=CY(CZW)$_n$—], wherein X, Y, Z, and W, independently, are H or F, and n is an integer from 2 to 5, and wherein the flammability factor is greater than or equal to 0.70; and
(c) fluoroolefins selected from the group consisting of: 1,2,3,3,3-pentafluoro-1-propene ($CF_3CF$=CHF); 1,1,3,3,3-pentafluoro-1-propene ($CF_3CH$=$CF_2$); 1,1,2,3,3-pentafluoro-1-propene ($CHF_2CF$=$CF_2$); 1,1,1,2,3,4,4,4-octafluoro-2-butene ($CF_3CF$=$CFCF_3$); 1,2,3,3,4,4,4-octafluoro-1-butene ($CF_3CF_2CF$=$CF_2$); 1,1,1,2,4,4,4-heptafluoro-2-butene ($CF_3CF$=$CHCF_3$); 1,2,3,3,4,4,4-heptafluoro-1-butene (CHF=$CFCF_2CF_3$); 1,1,1,2,3,4,4-heptafluoro-2-butene ($CHF_2CF$=$CFCF_3$); 1,3,3,3-tetrafluoro-2-(trifluoromethyl)-1-propene (($CF_3)_2$C=CHF); 1,1,3,3,4,4,4-heptafluoro-1-butene ($CF_2$=$CHCF_2CF_3$); 1,1,2,3,4,4,4-heptafluoro-1-butene ($CF_2$=$CFCHFCF_3$); 1,1,2,3,3,4,4-heptafluoro-1-butene ($CF_2$=$CFCF_2CHF_2$); 2,3,3,4,4,4-hexafluoro-1-butene ($CF_3CF_2CF$=$CH_2$); 1,3,3,4,4,4-hexafluoro-1-butene (CHF=$CHCF_2CF_3$); 1,2,3,4,4,4-hexafluoro-1-butene (CHF=$CFCHFCF_3$); 1,2,3,3,4,4-hexafluoro-1-butene (CHF=$CFCF_2CHF_2$); 1,1,2,3,4,4-hexafluoro-2-butene ($CHF_2CF$=$CFCHF_2$); 1,1,1,2,3,4-hexafluoro-2-butene ($CH_2FCF$=$CFCF_3$); 1,1,1,2,4,4-hexafluoro-2-butene ($CHF_2CH$=$CFCF_3$); 1,1,1,3,4,4-hexafluoro-2-butene ($CF_3CH$=$CFCHF_2$); 1,1,2,3,3,4-hexafluoro-1-butene ($CF_2$=$CFCF_2CH_2F$); 1,1,2,3,4,4-hexafluoro-1-butene ($CF_2$=$CFCHFCHF_2$); 3,3,3-trifluoro-2-(trifluoromethyl)-1-propene ($CH_2$=C($CF_3)_2$); 1,1,1,2,3,4,4,5,5,5-decafluoro-2-pentene ($CF_3CF$=$CFCF_2CF_3$); 1,2,3,3,4,4,5,5,5-decafluoro-1-pentene ($CF_2$=$CFCF_2CF_2CF_3$); 1,1,1,4,4,4-hexafluoro-2-(trifluoromethyl)-2-butene (($CF_3)_2$C=$CHCF_3$); 1,1,1,2,4,4,5,5,5-nonafluoro-2-pentene ($CF_3CF$=$CHCF_2CF_3$); 1,1,1,3,4,4,5,5,5-nonafluoro-2-pentene ($CF_3CH$=$CFCF_2CF_3$); 1,2,3,3,4,4,5,5,5-nonafluoro-1-pentene (CHF=$CFCF_2CF_2CF_3$); 1,1,3,3,4,4,5,5,5-nonafluoro-1-pentene ($CF_2$=$CHCF_2CF_2CF_3$); 1,1,2,3,3,4,4,5,5-nonafluoro-1-pentene ($CF_2$=$CFCF_2CF_2CHF_2$); 1,1,2,3,4,4,5,5,5-nonafluoro-2-pentene ($CHF_2CF$=$CFCF_2CF_3$); 1,1,1,2,3,4,4,5,5-nonafluoro-2-pentene ($CF_3CF$=$CFCF_2CHF_2$); 1,1,1,2,3,4,5,5,5-nonafluoro-2-pentene ($CF_3CF$=$CFCHFCF_3$); 1,2,3,4,4,4-hexafluoro-3-(trifluoromethyl)-1-butene (CHF=$CFCF(CF_3)_2$); 1,1,2,4,4,4-hexafluoro-3-(trifluoromethyl)-1-butene ($CF_2$=$CFCH(CF_3)_2$); 1,1,1,4,4,4-hexafluoro-2-(trifluoromethyl)-2-butene ($CF_3CH$=C($CF_3)_2$); 1,1,3,4,4,4-hexafluoro-3-(trifluoromethyl)-1-butene ($CF_2$=$CHCF(CF_3)_2$); 2,3,3,4,4,5,5,5-octafluoro-1-pentene ($CH_2$=$CFCF_2CF_2CF_3$); 1,2,3,3,4,4,5,5-octafluoro-1-pentene (CHF=$CFCF_2CF_2CHF_2$); 3,3,4,4,4-pentafluoro-2-(trifluoromethyl)-1-butene ($CH_2$=C($CF_3)$CF_2CF_3$); 1,1,4,4,4-pentafluoro-3-(trifluoromethyl)-1-butene ($CF_2$=$CHCH(CF_3)_2$); 1,3,4,4,4-pentafluoro-3-(trifluoromethyl)-1-butene (CHF=$CHCF(CF_3)_2$); 1,1,4,4,4-pentafluoro-2-(trifluoromethyl)-1-butene ($CF_2$=C($CF_3$)$CH_2CF_3$); 3,4,4,4-tetrafluoro-3-(trifluoromethyl)-1-butene (($CF_3)_2$CFCH=$CH_2$); 3,3,4,4,5,5,5-heptafluoro-1-pentene ($CF_3CF_2CF_2CH$=$CH_2$); 2,3,3,4,4,5,5-heptafluoro-1-pentene ($CH_2$=$CFCF_2CF_2CHF_2$); 1,1,3,3,5,5,5-heptafluoro-1-butene ($CF_2$=$CHCF_2CH_2CF_3$); 1,1,1,2,4,4,4-heptafluoro-3-methyl-2-butene ($CF_3CF$=C($CF_3$)($CH_3$)); 2,4,4,4-tetrafluoro-3-(trifluoromethyl)-1-butene ($CH_2$=$CFCH(CF_3)_2$); 1,4,4,4-tetrafluoro-3-(trifluoromethyl)-1-butene (CHF=$CHCH(CF_3)_2$); 1,1,1,4-tetrafluoro-2-(trifluoromethyl)-2-butene ($CH_2FCH$=C($CF_3)_2$); 1,1,1,3-tetrafluoro-2-(trifluoromethyl)-2-butene ($CH_3CF$=C($CF_3)_2$); 1,1,2,3,3,4,4,5,6,6,6-dodecafluoro-1-hexene ($CF_3(CF_2)_3CF$=$CF_2$); 1,1,1,2,2,3,4,5,5,6,6,6-dodecafluoro-3-hexene ($CF_3CF_2CF$=$CFCF_2CF_3$); 1,1,1,4,4,4-hexafluoro-2,3-bis(trifluoromethyl)-2-butene (($CF_3)_2$C=C($CF_3)_2$); 1,1,1,2,3,4,5,5,5-nonafluoro-4-(trifluoromethyl)-2-pentene (($CF_3)_2CFCF$=$CFCF_3$); 1,1,1,4,4,5,5,5-octafluoro-2-(trifluoromethyl)-2-pentene (($CF_3)_2$C=$CHC_2F_5$); 1,1,1,3,4,5,5,5-octafluoro-4-(trifluoromethyl)-2-pentene (($CF_3)_2CFCF$=$CHCF_3$); 3,3,4,4,5,5,6,6,6-nonafluoro-1-hexene ($CF_3CF_2CF_2CF_2CH$=$CH_2$); 4,4,4-trifluoro-3,3-bis(trifluoromethyl)-1-butene ($CH_2$=$CHC(CF_3)_3$); 1,1,1,4,4,4-hexafluoro-2-(trifluoromethyl)-3-methyl-2-butene (($CF_3)_2$C=C($CH_3$)($CF_3$)); 2,3,3,5,5,5-hexafluoro-4-(trifluoromethyl)-1-pentene ($CH_2$=$CFCF_2CH(CF_3)_2$); 1,1,1,2,4,4,5,5,5-nonafluoro-3-methyl-2-pentene ($CF_3CF$=C($CH_3$)$CF_2CF_3$); 1,1,1,5,5,5-hexafluoro-4-(trifluoromethyl)-2-pentene ($CF_3CH$=$CHCH(CF_3)_2$); 1,1,1,2,3,4,4,5,5,6,6,7,7,7-tetradecafluoro-2-heptene ($CF_3CF$=$CFCF_2CF_2C_2F_5$); 1,1,1,2,2,3,4,5,5,6,6,7,7,7- tetradecafluoro-3-heptene (CF$_3$CF$_2$CF=CFCF$_2$C$_2$F$_5$); 1,1,1,3,4,4,5,5,6,6,7,7,7-tridecafluoro-2-heptene (CF$_3$CH=CFCF$_2$CF$_2$C$_2$F$_5$); 1,1,1,2,4,4,5,5,6,6,7,7,7-tridecafluoro-2-heptene (CF$_3$CF=CHCF$_2$CF$_2$C$_2$F$_5$); 1,1,1,2,2,4,5,5,6,6,7,7,7-tridecafluoro-3-heptene (CF$_3$CF$_2$CH=CFCF$_2$C$_2$F$_5$); and 1,1,1,2,2,3,5,5,6,6,7,7,7-tridecafluoro-3-heptene (CF$_3$CF$_2$CF=CHCF$_2$C$_2$F$_5$).

In yet another embodiment, the fluoroolefins of the present disclosure that may be particularly useful in combination with flammable refrigerants, may be at least one fluoroolefin selected from the group consisting of:
(a) fluoroolefins of the formula E- or Z—R$^1$CH=CHR$^2$, wherein R$^1$ and R$^2$ are, independently, C$_1$ to C$_6$ perfluoroalkyl groups, and wherein the flammability factor is greater than or equal to 0.70; and
(b) cyclic fluoroolefins of the formula cyclo-[CX=CY (CZW)$_n$—], wherein X, Y, Z, and W, independently, are H or F, and n is an integer from 2 to 5, and wherein the flammability factor is greater than or equal to 0.70.

While the flammability factor provides a basis for predicting flammability of certain fluoroolefin compounds, there may be certain variables, such as position of the hydrogen atoms on the molecule that would account for certain isomers with a given molecular formula being flammable while other isomers are non-flammable. Therefore, the flammability factor may only be used as a tool for predicting flammability characteristics.

Flammable refrigerants of the present invention comprise any compound, which may be demonstrated to propagate a flame under specified conditions of temperature, pressure and composition when mixed with air. Flammable refrigerants may be identified by testing under conditions specified by ASHRAE (American Society of Heating, Refrigerating and Air-Conditioning Engineers, Inc.) Standard 34-2001, under ASTM (American Society of Testing and Materials) E681-01, with an electronic ignition source. Such tests of flammability are conducted with the refrigerant at 101 kPa (14.7 psia) and a specified temperature (typically 100° C. (212° F.), or room temperature, that being about 23° C. (73° F.) at various concentrations in air in order to determine the lower flammability limit (LFL) and upper flammability limit (UFL) of the test compound in air.

In practical terms, a refrigerant may be classified as flammable if upon leaking from a refrigeration apparatus or air-conditioning apparatus, and contacting an ignition source a fire may result. The compositions of the present invention, during such a leak, have a low probability of causing a fire.

Flammable refrigerants of the present invention include hydrofluorocarbons (HFCs), fluoroolefins, fluoroethers, hydrocarbon ethers, hydrocarbons, ammonia (NH$_3$), and combinations thereof.

Flammable HFC refrigerants include but are not limited to: difluoromethane (HFC-32), fluoromethane (HFC-41), 1,1,1-trifluoroethane (HFC-143a), 1,1,2-trifluoroethane (HFC-143), 1,1-difluoroethane (HFC-152a), fluoroethane (HFC-161), 1,1,1-trifluoropropane (HFC-263fb), 1,1,1,3,3-pentafluoropropane (HFC-365mfc), and combinations thereof. These flammable HFC refrigerants are commercial products available from a number of sources such as chemical synthesis companies or may be prepared by synthetic processes disclosed in the art.

Flammable refrigerants of the present invention further comprise fluoroolefins including but not limited to: 1,2,3,3-tetrafluoro-1-propene (HFC-1234ye); 1,3,3,3-tetrafluoro-1-propene (HFC-1234ze); 2,3,3,3-tetrafluoro-1-propene (HFC-1234yf); 1,1,2,3-tetrafluoro-1-propene (HFC-1234yc); 1,1,3,3-tetrafluoro-1-propene (HFC-1234zc); 2,3,3-trifluoro-1-propene (HFC-1243yf); 3,3,3-trifluoro-1-propene (HFC-1243zf); 1,1,2-trifluoro-1-propene (HFC-1243yc); 1,1,3-trifluoro-1-propene (HFC-1243zc); 1,2,3-trifluoro-1-propene (HFC-1243ye); and 1,3,3-trifluoro-1-propene (HFC-1243ze).

Flammable refrigerants of the present invention further comprise fluoroethers, compounds similar to hydrofluorocarbons, which also contain at least one ether group oxygen atom. Representative fluoroether refrigerants include but are not limited to C$_4$F$_9$OC$_2$H$_5$, available commercially.

Flammable refrigerants of the present invention further comprise hydrocarbon refrigerants. Representative hydrocarbon refrigerants include but are not limited to propane, propylene, cyclopropane, n-butane, isobutane, n-pentane, 2-methylbutane (isopentane), cyclobutane, cyclopentane, 2,2-dimethylpropane, 2,2-dimethylbutane, 2,3-dimethylbutane, 2,3-dimethylpentane, 2-methylhexane, 3-methylhexane, 2-methylpentane, 3-ethylpentane, 3-methylpentane, cyclohexane, n-heptane, methylcyclopentane, and n-hexane. Flammable hydrocarbon refrigerants are readily available from multiple commercial sources.

Flammable refrigerants of the present invention further comprise hydrocarbon ethers, such as dimethyl ether (DME, CH$_3$OCH$_3$) and methyl t-butyl ether (MTBE, (CH$_3$)$_3$COCH$_3$), both available from multiple commercial sources.

Flammable refrigerants of the present invention further comprise ammonia (NH$_3$), a commercially available compound.

Flammable refrigerants of the present invention may further comprise mixtures of more than one refrigerant such as a mixture of two or more flammable refrigerants (eg. two HFCs or an HFC and a hydrocarbon) or a mixture comprising a flammable refrigerant and a non-flammable refrigerant, such that the overall mixture is still considered to be a flammable refrigerant, identified under the ASTM conditions described herein, or in practical terms.

Examples of non-flammable refrigerants that may be combined with other refrigerants of the present invention include R-134a, R-134, R-23, R125, R-236fa, R-245fa, and mixtures of HCFC-22/HFC-152a/HCFC-124 (known by the ASHRAE designations, R401 or R-401A, R-401B, and R-401C), HFC-125/HFC-143a/HFC-134a (known by the ASHRAE designation, R-404 or R-404A), HFC-32/HFC-125/HFC-134a (known by ASHRAE designations, R407 or R-407A, R-407B, and R-407C), HCFC-22/HFC-143a/HFC-125 (known by the ASHRAE designation, R408 or R-408A), HCFC-22/HCFC-124/HCFC-142b (known by the ASHRAE designation: R-409 or R-409A), HFC-32/HFC-125 (known by the ASHRAE designation R-410A), and HFC-125/HFC-143a (known by the ASHRAE designation: R-507 or R507A) and carbon dioxide.

Examples of mixtures of more than one flammable refrigerant include propane/isobutane; HFC-152a/isobutane, R32/propane; R32/isobutane; and HFC/carbon dioxide mixtures such as HFC-152a/CO$_2$.

One aspect of the present invention is to provide a non-flammable refrigerant with a global warming potential of less than 150, preferably less than 50. Another aspect of the present invention is to reduce the flammability of flammable refrigeration mixtures by adding non-flammable fluoroolefins to said mixtures.

It may be demonstrated that while certain refrigerants are flammable, it is possible to produce a non-flammable refrigerant composition by adding to the flammable refrigerant another compound that is not flammable. Examples of such nonflammable refrigerant blends include R-410A (HFC-32 is a flammable refrigerant, while HFC-125 is non-flammable), and R-407C (HFC-32 is a flammable refrigerant, while HFC-125 and HFC-134a are not flammable).

The compositions of the present invention that are useful as refrigerants or heat transfer fluids comprising at least one fluoroolefin and at least one flammable refrigerant may contain an effective amount of fluoroolefin to produce a composition that is non-flammable based upon results of ASTM E681-01.

The present inventive compositions comprising at least one flammable refrigerant and at least one fluoroolefin may contain about 1 weight percent to about 99 weight percent fluoroolefin and about 99 weight percent to about 1 weight percent flammable refrigerant.

In another embodiment, the compositions of the present invention may contain about 10 weight percent to about 80 weight percent fluoroolefin and about 90 weight percent to about 20 weight percent flammable refrigerant. In yet another embodiment, the compositions of the present invention may contain about 20 weight percent to about 70 weight percent fluoroolefin and about 80 weight percent to about 30 weight percent flammable refrigerant.

Of particular interest is an embodiment of the present disclosure wherein the fluoroolefin comprises HFC-1225ye and the flammable refrigerant comprises HFC-32 (difluoromethane). It has been determined that compositions comprising up to 37 weight percent HFC-32 are non-flammable, while compositions comprising 38 weight percent HFC-32 or greater are flammable as determined by ASTM 681-01. The present disclosure provides non-flammable compositions comprising about 1.0 weight percent to about 37.0 weight percent HFC-32 and about 99.0 weight percent to about 63 weight percent HFC-1225ye.

Also, of particular interest is an embodiment of the present disclosure wherein the composition comprises HFC-1225ye, HFC-32 and HFC-125. This composition of the present invention comprises about 20 weight percent to about 95 weight percent HFC-1225ye, about 1.0 weight percent to about 65 weight percent HFC-32, and about 1.0 weight percent to about 40 weight percent HFC-125. In another embodiment, the composition comprises about 30 weight percent to about 90 weight percent HFC-1225ye, about 5.0 weight percent to about 55 weight percent HFC-32, and about 1.0 weight percent to about 35 weight percent HFC-125. In yet another embodiment, the composition comprises about 40 weight percent to about 85 weight percent HFC-1225ye, about 10 weight percent to about 45 weight percent HFC-32 and about 1.0 weight percent to about 28 weight percent HFC-125. Those compositions containing less than about 40 weight percent HFC-32 are expected to be non-flammable compositions. This flammability limit will vary from less than about 45 weight percent HFC-32 to less than about 37 weight percent HFC-32 depending on the relative ratios of HFC-1225ye and HFC-125 present in the composition.

In another embodiment of particular interest, the flammable refrigerant comprises HFC-1243zf and a non-flammable fluoroolefin intended to reduce the flammability of the overall composition. The composition may comprise about 1.0 weight percent to about 99 weight percent HFC-1243zf and about 99 weight percent to about 1.0 weight percent HFC-1225ye. Alternatively, the composition may comprise about 40 weight percent to about 70 weight percent HFC-1243zf and about 60 weight percent to about 30 weight percent HFC-1225ye.

In another embodiment of particular interest, the composition comprises about 1.0 weight percent to about 98 weight percent HFC-1243zf; about 1.0 weight percent to about 98 weight percent HFC-1225ye; and about 1.0 weight percent to about 50 weight percent HFC-125. Alternatively, the composition comprises about 40 weight percent to about 70 weight percent HFC-1243zf; about 20 weight percent to about 60 weight percent HFC-1225ye; and about 1.0 weight percent to about 10 weight percent HFC-125.

In another embodiment of particular interest the composition comprises about 1.0 weight percent to about 98 weight percent HFC-1243zf; about 1.0 weight percent to about 98 weight percent HFC-1225ye; and about 1.0 weight percent to about 50 weight percent HFC-32. Alternatively, the composition comprises about 40 weight percent to about 70 weight percent HFC-1243zf; about 20 weight percent to about 60 weight percent HFC-1225ye; and about 1.0 weight percent to about 10 weight percent HFC-32.

In yet another embodiment of particular interest, the composition comprises about 1.0 weight percent to about 97 weight percent HFC-1243zf; about 1.0 weight percent to about 97 weight percent HFC-1225ye; about 1.0 weight percent to about 50 weight percent HFC-125; and about 1.0 weight percent to about 50 weight percent HFC-32. Alternatively, the composition comprises about 40 weight percent to about 70 weight percent HFC-1243zf; about 20 weight percent to about 60 weight percent HFC-1225ye; and about 1.0 weight percent to about 10 weight percent HFC-125; and about 1.0 weight percent to about 10 weight percent HFC-32.

The present invention further relates to a method for reducing the flammability of a flammable refrigerant said method comprising combining the flammable refrigerant with at least one fluoroolefin. The amount of fluoroolefin added must be an effective amount to produce a non-flammable compositions as determined by ASTM 681-01.

Compositions of the present invention may be used in combination with a desiccant in a refrigeration, air-conditioning, or heat pump system to aid in removal of moisture. Desiccants may be composed of activated alumina, silica gel, or zeolite based molecular sieves. Representative molecular sieves include MOLSIV XH-7, XH-6, XH-9 and XH-11 (UOP LLC, Des Plaines, Ill.). For refrigerants with small molecular size such as HFC-32, XH-11 desiccant is preferred.

The compositions of the present invention may further comprise at least one lubricant. Lubricants of the present invention comprise those suitable for use with refrigeration or air-conditioning apparatus. Among these lubricants are those conventionally used in compression refrigeration apparatus utilizing chlorofluorocarbon refrigerants. Such lubricants and their properties are discussed in the 1990 ASHRAE Handbook, Refrigeration Systems and Applications, chapter 8, titled "Lubricants in Refrigeration Systems", pages 8.1 through 8.21, herein incorporated by reference. Lubricants of the present invention may comprise those commonly known as "mineral oils" in the field of compression refrigeration lubrication. Mineral oils comprise paraffins (i.e. straight-chain and branched-carbon-chain, saturated hydrocarbons), naphthenes (i.e. cyclic paraffins) and aromatics (i.e. unsaturated, cyclic hydrocarbons containing one or more rings characterized by alternating double bonds). Lubricants of the present invention further comprise those commonly known as "synthetic oils" in the field of compression refrigeration lubrication. Synthetic oils comprise alkylaryls (i.e. linear and branched alkyl alkylbenzenes), synthetic paraffins and naphthenes, and poly(alphaolefins). Representative conventional lubricants of the present invention are the commercially available BVM 100 N (paraffinic mineral oil sold by BVA Oils), Suniso® 3GS and Suniso® 5GS (naphthenic mineral oil sold by Crompton Co.), Sontex® 372LT (naphthenic mineral oil sold by Pennzoil), Calumet® RO-30 (naphthenic mineral oil sold by Calumet Lubricants), Zerol® 75, Zerol® 150 and Zerol® 500 (linear alkylbenzenes sold by Shrieve Chemicals) and HAB 22 (branched alkylbenzene sold by Nippon Oil).

Lubricants of the present invention further comprise those, which have been designed for use with hydrofluorocarbon refrigerants and are miscible with refrigerants of the present invention under compression refrigeration and air-conditioning apparatus' operating conditions. Such lubricants and their properties are discussed in "Synthetic Lubricants and High-Performance Fluids", R. L. Shubkin, editor, Marcel Dekker, 1993. Such lubricants include, but are not limited to, polyol esters (POEs) such as Castrol® 100 (Castrol, United Kingdom), polyalkylene glycols (PAGs) such as RL-488A from Dow (Dow Chemical, Midland, Mich.), and polyvinyl ethers (PVEs).

Lubricants of the present invention are selected by considering a given compressor's requirements and the environment to which the lubricant will be exposed.

Commonly used refrigeration system additives may optionally be added, as desired, to compositions of the present invention in order to enhance lubricity and system stability. These additives are generally known within the field of refrigeration compressor lubrication, and include anti wear agents, extreme pressure lubricants, corrosion and oxidation inhibitors, metal surface deactivators, foaming and antifoam control agents, leak detectants and the like. In general, these additives are present only in small amounts relative to the overall lubricant composition. They are typically used at concentrations of from less than about 0.1% to as much as about 3% of each additive. These additives are selected on the basis of the individual system requirements. Some typical examples of such additives may include, but are not limited to, lubrication enhancing additives, such as alkyl or aryl esters of phosphoric acid and of thiophosphates. Additionally, the metal dialkyl dithiophosphates (e.g. zinc dialkyl dithiophosphate or ZDDP, Lubrizol 1375) and other members of this family of chemicals may be used in compositions of the present invention. Other antiwear additives include natural product oils and assymetrical polyhydroxyl lubrication additives such as Synergol TMS (International Lubricants). Similarly, stabilizers such as antioxidants, free radical scavengers, and water scavengers (drying compounds) may be employed. Such additives include but are not limited to, nitromethane, hindered phenols (such as butylated hydroxy toluene, or BHT), hydroxylamines, thiols, phosphites, epoxides or lactones. Water scavengers include but are not limited to ortho esters such as trimethyl-, triethyl-, or tripropylortho formate. Single additives or combinations may be used.

In one embodiment, the present invention provides compositions comprising at least one fluoroolefin and at least one stabilizer selected from the group consisting of thiophosphates, butylated triphenylphosphorothionates, organo phosphates, dialkylthiophosphate esters, terpenes, terpenoids, fullerenes, functionalized perfluoropolyethers, polyoxyalkylated aromatics, epoxides, fluorinated epoxides, oxetanes, ascorbic acid, thiols, lactones, thioethers, nitromethanes, alkylsilanes, benzophenone derivatives, arylsulfide, divinyl terephthalate, diphenyl terephthalate, alkylamines, hindered amine antioxidants, and phenols, The alkylamines can include triethylamine, tributylamine, diisopropylamine, triisopropylamine, triisobutylamine, and other members of this family of alkylamine compounds.

In another embodiment, the stabilizers of the present invention may comprise specific combinations of stabilizers. One combination of stabilizers of particular interest comprises at least one terpene or terpenoid. These terpenes or terpenoids may be combined with at least one compound selected from epoxides, fluorinated epoxides, and oxetanes.

Terpenes are hydrocarbon compounds characterized by structures containing more than one repeating isoprene (2-methyl-1,3-butadiene) unit. Terpenes may be acyclic or cyclic. Representative terpenes include but are not limited to myrcene (2-methyl-6-methyl-eneocta-1,7-diene), allocimene, beta-ocimene, terebene, limonene (or d-limonene), retinal, pinene (or alpha-pinene), menthol, geraniol, farnesol, phytol, Vitamin A, terpinene, delta-3-carene, terpinolene, phellandrene, fenchene and mixtures thereof. Terpene stabilizers are commercially available or may be prepared by methods known in the art or isolated from natural sources.

Terpenoids are natural products and related compounds characterized by structures containing more than one repeating isoprene unit and optionally contain oxygen. Representative terpenoids include carotenoids, such as lycopene (CAS reg. no. [502-65-8]), betacarotene (CAS reg. no. [7235-40-7]), and xanthophylls, i.e. zeaxanthin (CAS reg. no. [144-68-3]); retinoids, such as hepaxanthin (CAS reg. no. [512-39-0]), and isotretinoin (CAS reg. no. [4759-48-2]); abietane (CAS reg. no. [640-43-7]); ambrosane (CAS reg. no. [24749-18-6]); aristolane (CAS reg. no. [29788-49-6]); atisane (CAS reg. no. [24379-83-7]); beyerane (CAS reg. no. [2359-83-3]), bisabolane (CAS reg. no. [29799-19-7]); bornane (CAS reg. no. [464-15-3]); caryophyllane (CAS reg. no. [20479-00-9]); cedrane (CAS reg. no. [13567-54-9]); dammarane (CAS reg. no. [545-22-2]); drimane (CAS reg. no. [5951-58-6]); eremophilane (CAS reg. no. [3242-05-5]); eudesmane (CAS reg. no. [473-11-0]); fenchane (CAS reg. no. [6248-88-0]); gammacerane (CAS reg. no. [559-65-9]); germacrane (CAS reg. no. [645-10-3]); gibbane (CAS reg. no. [6902-95-0]); grayanotoxane (CAS reg. no. [39907-73-8]); guaiane (CAS reg. no. [489-80-5]); himachalane (CAS reg. no. [20479-45-2]); hopane (CAS reg. no. [471-62-5]); humulane (CAS reg. no. [430-19-3]); kaurane (CAS reg. no. [1573-40-6]); labdane (CAS reg. no. [561-90-0]); lanostane (CAS reg. no. [474-20-4]); lupane (CAS reg. no. [464-99-3]); p-menthane (CAS reg. no. [99-82-1]); oleanane (CAS reg. no. [471-67-0]); ophiobolane (CAS reg. no. [20098-65-1]); picrasane (CAS reg. no. [35732-97-9]); pimarane (CAS reg. no. [30257-03-5]); pinane (CAS reg. no. [473-55-2]); podocarpane (CAS reg. no. [471-78-3]); protostane (CAS reg. no. [70050-78-1]); rosane (CAS reg. no. [6812-82-4]); taxane (CAS reg. no. [1605-68-1]); thujane (CAS reg. no. [471-12-5]); trichothecane (CAS reg. no. [24706-08-9]); and ursane (CAS reg. no. [464-93-7]). The terpenoids of the present invention are commercially available or may be prepared by methods known in the art or may be isolated from the naturally occurring source.

In one embodiment, the terpene or terpenoid stabilizers may be combined with at least one epoxide. Representative epoxides include 1,2-propylene oxide (CAS reg. no. [75-56-9]); 1,2-butylene oxide (CAS reg. no. [106-88-7]); or mixtures thereof.

In another embodiment, the terpene or terpenoid stabilizers of the present invention may be combined with at least one fluorinated epoxide. The fluorinated epoxides of the present invention may be depicted by Formula 3, wherein each of $R^2$ through $R^5$ is H, alkyl of 1-6 carbon atoms or fluoroalkyl of 1-6 carbon atoms with the proviso that at least one of $R^2$ through $R^5$ is a fluoroalkyl group.

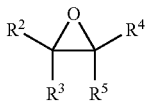

Formula 3

Representative fluorinated epoxide stabilizers include but are not limited to trifluoromethyloxirane and 1,1-bis(trifluoromethyl)oxirane. Such compounds may be prepared by methods known in the art, for instance by methods described in, *Journal of Fluorine Chemistry*, volume 24, pages 93-104 (1984), *Journal of Organic Chemistry*, volume 56, pages 3187 to 3189 (1991), and *Journal of Fluorine Chemistry*, volume 125, pages 99-105 (2004).

In another embodiment, the terpene or terpenoid stabilizers of the present invention may be combined with at least one oxetane. The oxetane stabilizers of the present invention may be compounds with one or more oxetane groups and is represented by Formula 4, wherein $R_1$-$R_6$ are the same or different and can be selected from hydrogen, alkyl or substituted alkyl, aryl or substituted aryl.

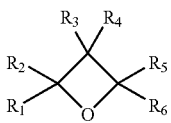

Formula 4

Representative oxetane stabilizers include but are not limited to 3-ethyl-3-hydroxymethyl-oxetane, such as OXT-101 (Toagosei Co., Ltd); 3-ethyl-3-((phenoxy)methyl)-oxetane, such as OXT-211 (Toagosei Co., Ltd); and 3-ethyl-3-((2-ethylhexyloxy)methyl)-oxetane, such as OXT-212 (Toagosei Co., Ltd).

Another embodiment of particular interest is a combination of stabilizers comprising fullerenes. The fullerene stabilizers may be combined with at least one compound selected from the group consisting of epoxides, fluorinated epoxides, and oxetanes. The epoxides, fluorinated epoxides, and oxetanes for combination with fullerenes have been previously described herein as for combination with terpenes or terpenoids.

Another embodiment of particular interest is a combination of stabilizers comprising phenols. The fullerene stabilizers may be combined with at least one compound selected from the group consisting of epoxides, fluorinated epoxides, and oxetanes. The epoxides, fluorinated epoxides, and oxetanes for combination with phenols have been previously described herein as for combination with terpenes or terpenoids.

Phenol stabilizers comprise any substituted or unsubstituted phenol compound including phenols comprising one or more substituted or unsubstituted cyclic, straight chain, or branched aliphatic substituent group, such as, alkylated monophenols including 2,6-di-tert-butyl-4-methylphenol; 2,6-di-tert-butyl-4-ethylphenol; 2,4-dimethyl-6-tertbutylphenol; tocopherol; and the like, hydroquinone and alkylated hydroquinones including t-butyl hydroquinone, other derivatives of hydroquinone; and the like, hydroxylated thiodiphenyl ethers, including 4,4'-thio-bis(2-methyl-6-tert-butylphenol); 4,4'-thiobis(3-methyl-6-tertbutylphenol); 2,2'-thiobis(4-methyl-6-tert-butylphenol); and the like, alkylidene-bisphenols including: 4,4'-methylenebis(2,6-di-tert-butylphenol); 4,4'-bis(2,6-di-tert-butylphenol); derivatives of 2,2'- or 4,4-biphenoldiols; 2,2'-methylenebis(4-ethyl-6-tertbutylphenol); 2,2'-methylenebis(4-methyl-6-tertbutylphenol); 4,4-butylidenebis(3-methyl-6-tert-butylphenol); 4,4-isopropylidenebis(2,6-di-tert-butylphenol); 2,2'-methylenebis(4-methyl-6-nonylphenol); 2,2'-isobutylidenebis(4,6-dimethylphenol); 2,2'-methylenebis(4-methyl-6-cyclohexylphenol, 2,2- or 4,4-biphenyldiols including 2,2'-methylenebis(4-ethyl-6-tert-butylphenol); butylated hydroxyl toluene (BHT), bisphenols comprising heteroatoms including 2,6-di-tert-alpha-dimethylamino-p-cresol, 4,4-thiobis(6-tert-butyl-m-cresol); and the like; acylaminophenols; 2,6-di-tert-butyl-4(N,N'-dimethylaminomethylphenol); sulfides including; bis(3-methyl-4-hydroxy-5-tert-butylbenzyl)sulfide; bis(3,5-di-tert-butyl-4-hydroxybenzyl)sulfide; and the like.

In one embodiment of the present invention, these combinations of stabilizers comprising terpenes or terpenoids, or fullerenes or phenols with at least one compound selected from the group consisting of epoxides, fluorinated epoxides, and oxetanes, may further comprise an additional stabilizer compound selected from the group consisting of:

areoxalyl bis(benzylidene)hydrazide (CAS reg. no. 6629-10-3);
N,N'-bis(3,5-di-tert-butyl-4-hydroxyhydrocinnamoylhydrazine) (CAS reg. no. 32687-78-8);
2,2'-oxamidobis-ethyl-(3,5-d-tert-butyl-4-hydroxyhydrorcinnamate) (CAS reg. no. 70331-94-1);
N,N'-(disalicyclidene)-1,2-propanediamine (CAS reg. no. 94-91-1); and ethyenediaminetetraacetic acid (CAS reg. no. 60-00-4) and salts thereof.

In another embodiment of the present invention, these combinations of stabilizers comprising terpenes or terpenoids, or fullerenes or phenols with at least one compound selected from the group consisting of epoxides, fluorinated epoxides, and oxetanes, may further comprise at least one alkylamine selected from the group consisting of triethylamine; tributylamine; triisopropylamine; diisobutylamine; triisopropylamine; triisobutylamine; and hindered amine antioxidants.

The compositions of the present invention may further comprise a compound or composition that is a tracer and is selected from the group consisting of hydrofluorocarbon (HFCs), deuterated hydrocarbon, deuterated hydrofluorocarbon, perfluorocarbons, fluoroether, brominated compound, iodated compound, alcohol, aldehyde, ketones, nitrous oxide ($N_2O$) and combinations thereof. The tracer used in the present invention are different compositions from those used as refrigerant or heat transfer fluids, are added to the refrigerant and heat transfer compositions in previously determined quantities to allow detection of any dilution, contamination or other alteration of the composition, as described in U.S. patent application Ser. No. 11/062,044, filed Feb. 18, 2005.

Typical tracer compounds for use in the present compositions are listed in Table 5.

TABLE 5

| Compound | Structure |
|---|---|
| Deuterated hydrocarbons and hydrofluorocarbons | |
| Ethane-d6 | $CD_3CD_3$ |
| Propane-d8 | $CD_3CD_2CD_3$ |
| HFC-32-d2 | $CD_2F_2$ |
| HFC-134a-d2 | $CD_2FCF_3$ |
| HFC-143a-d3 | $CD_3CF_3$ |
| HFC-125-d | $CDF_2CF_3$ |

TABLE 5-continued

| Compound | Structure |
|---|---|
| HFC-227ea-d | $CF_3CDFCF_3$ |
| HFC-227ca-d | $CF_3CF_2CDF_2$ |
| HFC-134-d2 | $CDF_2CDF_2$ |
| HFC-236fa-d2 | $CF_3CD_2CF_3$ |
| HFC-245cb-d3 | $CF_3CF_2CD_3$ |
| HFC-263fb-d2* | $CF_3CD_2CH_3$ |
| HFC-263fb-d3 | $CF_2CH_2CD_3$ |
| Fluoroethers | |
| HFOC-125E | $CHF_2OCF_3$ |
| HFOC-134aE | $CH_2FOCF_3$ |
| HFOC-143aE | $CH_3OCF_3$ |
| HFOC-227eaE | $CF_3OCHF-F_3$ |
| HFOC-236faE | $CF_3OCH_2CF_3$ |
| HFOC-245faEβγ or | $CHF_2OCH_2CF_3$ |
| HFOC-245faEαβ | (or $CHF_2CH_2OCF_3$) |
| HFOC-245cbEβγ or | $CH_3OCF_2CF_3$ |
| HFOC-245cbαβ | (or $CH_3CF_2OCF_3$) |
| HFE-42-11mcc (or Freon® E1) | $CF_3CF_2CF_2OCHFCF_3$ |
| Freon® E2 | $CF_3CF_2CF_2OCF(CF_3)CF_2OCHFCF_3$ |
| Hydrofluorocarbons | |
| HFC-23 | $CHF_3$ |
| HFC-161 | $CH_3CH_2F$ |
| HFC-152a | $CH_3CHF_2$ |
| HFC-134 | $CHF_2CHF_2$ |
| HFC-227ea | $CF_3CHFCF_3$ |
| HFC-227ca | $CHF_2CF_2CF_3$ |
| HFC-236cb | $CH_2FCF_2CF_3$ |
| HFC-236ea | $CF_3CHFCHF_2$ |
| HFC-236fa | $CF_3CH_2CF_3$ |
| HFC-245cb | $CF_3CF_2CH_3$ |
| HFC-245fa | $CHF_2CH_2CF_3$ |
| HFC-254cb | $CHF_2CF_2CH_3$ |
| HFC-254eb | $CF_3CHFCH_3$ |
| HFC-263fb | $CF_3CH_2CH_3$ |
| HFC-272ca | $CH_3CF_2CH_3$ |
| HFC-281ea | $CH_3CHFCH_3$ |
| HFC-281fa | $CH_2FCH_2CH_3$ |
| HFC-329p | $CHF_2CF_2CF_2CF_3$ |
| HFC-329mmz | $(CH_3)_2CHCF_3$ |
| HFC-338mf | $CF_3CH_2CF_2CF_3$ |
| HFC-338pcc | $CHF_2CF_2CF_2CHF_2$ |
| HFC-347s | $CH_3CF_2CF_2CF_3$ |
| HFC-43-10mee | $CF_3CHFCHFCF_2CF_3$ |
| Perfluorocarbons | |
| PFC-116 | $CF_3CF_3$ |
| PFC-C216 | Cyclo(—$CF_2CF_2CF_2$—) |
| PFC-218 | $CF_3CF_2CF_3$ |
| PFC-C318 | Cyclo(—$CF_2CF_2CF_2CF_2$—) |
| PFC-31-10mc | $CF_3CF_2CF_2CF_3$ |
| PFC-31-10my | $(CF_3)_2CFCF_3$ |
| PFC-C51-12mycm | Cyclo(—$CF(CF_3)CF_2CF(CF_3)CF_2$—) |
| PFC-C51-12mym, trans | Cyclo(—$CF_2CF(CF_3)CF(CF_3)CF_2$—) |
| PFC-C51-12mym, cis | Cyclo(—$CF_2CF(CF_3)CF(CF_3)CF_2$—) |
| Perfluoromethylcyclopentane | Cyclo(—$CF_2CF_2(CF_3)CF_2CF_2CF_2$—) |
| Perfluoromethylcyclohexane | Cyclo-(—$CF_2CF_2(CF_3)CF_2CF_2CF_2CF_2$—) |
| Perfluorodimethylcyclohexane (ortho, meta, or para) | Cyclo(—$CF_2CF_2(CF_3)CF_2CF_2(CF_3)CF_2$—) |
| Perfluoroethylcyclohexane | Cyclo(—$CF_2CF_2(CF_2CF_3)CF_2CF_2CF_2CF_2$—) |
| Perfluoroindan | $C_9F_{10}$ (see structure below) |

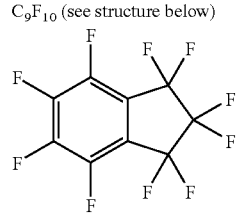

TABLE 5-continued

| Compound | Structure |
|---|---|
| Perfluorotrimethylcyclohexane (all possible isomers) | Cyclo(—$CF_2(CF_3)CF_2(CF_3)CF_2CF_2(CF_3)CF_2$—) |
| Perfluoroisopropylcyclohexane | Cyclo(—$CF_2CF_2(CF_2(CF_3)_2)CF_2CF_2CF_2CF_2$—) |
| Perfluorodecalin (cis or trans, trans shown) | $C_{10}F_{18}$ (see structure below) |
| Perfluoromethyldecalin (cis or trans and all additional possible isomers) | $C_{11}F_{20}$ (see structure below) |
| Brominated compounds | |
| Bromomethane | $CH_3Br$ |
| Bromofluoromethane | $CH_2FBr$ |
| Bromodifluoromethane | $CHF_2Br$ |
| Dibromofluoromethane | $CHFBr_2$ |
| Tribromomethane | $CHBr_3$ |
| Bromoethane | $CH_3CH_2Br$ |
| Bromoethene | $CH_2=CHBr$ |
| 1,2-dibromoethane | $CH_2BrCH_2Br$ |
| 1-bromo-1,2-difluoroethene | $CFBr=CHF$ |
| Iodated compounds | |
| Iodotrifluoromethane | $CF_3I$ |
| Difluoroiodomethane | $CHF_2I$ |
| Fluoroiodomethane | $CH_2FI$ |
| 1,1,2-trifluoro-1-iodoethane | $CF_2ICH_2F$ |
| 1,1,2,2-tetrafluoro-1-iodoethane | $CF_2ICHF_2$ |
| 1,1,2,2-tetrafluoro-1,2-diiodoethane | $CF_2ICF_2I$ |
| Iodopentafluorobenzene | $C_6F_5I$ |
| Alcohols | |
| Ethanol | $CH_3CH_2OH$ |
| n-propanol | $CH_3CH_2CH_2OH$ |
| Isopropanol | $CH_3CH(OH)CH_3$ |
| Aldehydes and Ketones | |
| Acetone (2-propanone) | $CH_3C(O)CH_3$ |
| n-propanal | $CH_3CH_2CHO$ |
| n-butanal | $CH_3CH_2CH_2CHO$ |
| Methyl ethyl ketone (2-butanone) | $CH_3C(O)CH_2CH_3$ |
| Other | |
| Nitrous oxide | $N_2O$ |

The compounds listed in Table 5 are available commercially (from chemical supply houses) or may be prepared by processes known in the art.

Single tracer compounds may be used in combination with a refrigeration/heating fluid in the compositions of the present invention or multiple tracer compounds may be combined in any proportion to serve as a tracer blend. The tracer blend may contain multiple tracer compounds from the same class of compounds or multiple tracer compounds from different classes of compounds. For example, a tracer blend may contain 2 or more deuterated hydrofluorocarbons, or one deuterated hydrofluorocarbon in combination with one or more perfluorocarbons.

Additionally, some of the compounds in Table 4 exist as multiple isomers, structural or optical. Single isomers or multiple isomers of the same compound may be used in any proportion to prepare the tracer compound. Further, single or multiple isomers of a given compound may be combined in any proportion with any number of other compounds to serve as a tracer blend.

The tracer compound or tracer blend may be present in the compositions at a total concentration of about 50 parts per million by weight (ppm) to about 1000 ppm. Preferably, the tracer compound or tracer blend is present at a total concentration of about 50 ppm to about 500 ppm and most preferably, the tracer compound or tracer blend is present at a total concentration of about 100 ppm to about 300 ppm.

The compositions of the present invention may further comprise an ultra-violet (UV) dye and optionally a solubilizing agent. The UV dye is a useful component for detecting leaks of the refrigerant composition or heat transfer fluids by permitting one to observe the fluorescence of the dye in the refrigerant or heat transfer fluid composition at or in the vicinity of a leak point in said apparatus in the refrigeration, air-conditioning, heat pump apparatus. One may observe the fluorescence of the dye under an ultra-violet light. Solubilizing agents may be needed due to poor solubility of such UV dyes in some refrigerants and heat transfer fluids.

By "ultra-violet" dye is meant a UV fluorescent composition that absorbs light in the ultra-violet or "near" ultra-violet region of the electromagnetic spectrum. The fluorescence produced by the UV fluorescent dye under illumination by a UV light that emits radiation with wavelength anywhere from 10 nanometer to 750 nanometer may be detected. Therefore, if refrigerant or heat transfer fluid containing such a UV fluorescent dye is leaking from a given point in a refrigeration, air-conditioning, or heat pump apparatus, the fluorescence can be detected at the leak point, or in the vicinity of the leak point. Such UV fluorescent dyes include but are not limited to naphthalimides, perylenes, coumarins, anthracenes, phenanthracenes, xanthenes, thioxanthenes, naphthoxanthenes, fluoresceins, and derivatives of said dye or combinations thereof. Solubilizing agents of the present invention comprise at least one compound selected from the group consisting of hydrocarbons, hydrocarbon ethers, polyoxyalkylene glycol ethers, amides, nitriles, ketones, chlorocarbons, esters, lactones, aryl ethers, fluoroethers and 1,1,1-trifluoroalkanes.

Hydrocarbon solubilizing agents of the present invention comprise hydrocarbons including straight chained, branched chain or cyclic alkanes or alkenes containing 16 or fewer carbon atoms and only hydrogen with no other functional groups. Representative hydrocarbon solubilizing agents comprise propane, propylene, cyclopropane, n-butane, isobutane, n-pentane, octane, decane, and hexadecane. It should be noted that if the refrigerant is a hydrocarbon, then the solubilizing agent may not be the same hydrocarbon.

Hydrocarbon ether solubilizing agents of the present invention comprise ethers containing only carbon, hydrogen and oxygen, such as dimethyl ether (DME).

Polyoxyalkylene glycol ether solubilizing agents of the present invention are represented by the formula $R^1[(OR^2)_xOR^3]_y$, wherein: x is an integer from 1-3; y is an integer from 1-4; $R^1$ is selected from hydrogen and aliphatic hydrocarbon radicals having 1 to 6 carbon atoms and y bonding sites; $R^2$ is selected from aliphatic hydrocarbylene radicals having from 2 to 4 carbon atoms; $R^3$ is selected from hydrogen and aliphatic and alicyclic hydrocarbon radicals having from 1 to 6 carbon atoms; at least one of $R^1$ and $R^3$ is said hydrocarbon radical; and wherein said polyoxyalkylene glycol ethers have a molecular weight of from about 100 to about 300 atomic mass units. As used herein, bonding sites mean radical sites available to form covalent bonds with other radicals. Hydrocarbylene radicals mean divalent hydrocarbon radicals. In the present invention, preferred polyoxyalkylene glycol ether solubilizing agents are represented by $R^1[(OR^2)_xOR^3]_y$: x is preferably 1-2; y is preferably 1; $R^1$ and $R^3$ are preferably independently selected from hydrogen and aliphatic hydrocarbon radicals having 1 to 4 carbon atoms; $R^2$ is preferably selected from aliphatic hydrocarbylene radicals having from 2 or 3 carbon atoms, most preferably 3 carbon atoms; the polyoxyalkylene glycol ether molecular weight is preferably from about 100 to about 250 atomic mass units, most preferably from about 125 to about 250 atomic mass units. The $R^1$ and $R^3$ hydrocarbon radicals having 1 to 6 carbon atoms may be linear, branched or cyclic. Representative $R^1$ and $R^3$ hydrocarbon radicals include methyl, ethyl, propyl, isopropyl, butyl, isobutyl, sec-butyl, tert-butyl, pentyl, isopentyl, neopentyl, tert-pentyl, cyclopentyl, and cyclohexyl. Where free hydroxyl radicals on the present polyoxyalkylene glycol ether solubilizing agents may be incompatible with certain compression refrigeration apparatus materials of construction (e.g. Mylar®), $R^1$ and $R^3$ are preferably aliphatic hydrocarbon radicals having 1 to 4 carbon atoms, most preferably 1 carbon atom. The $R^2$ aliphatic hydrocarbylene radicals having from 2 to 4 carbon atoms form repeating oxyalkylene radicals $—(OR^2)_x—$ that include oxyethylene radicals, oxypropylene radicals, and oxybutylene radicals. The oxyalkylene radical comprising $R^2$ in one polyoxyalkylene glycol ether solubilizing agent molecule may be the same, or one molecule may contain different $R^2$ oxyalkylene groups. The present polyoxyalkylene glycol ether solubilizing agents preferably comprise at least one oxypropylene radical. Where $R^1$ is an aliphatic or alicyclic hydrocarbon radical having 1 to 6 carbon atoms and y bonding sites, the radical may be linear, branched or cyclic. Representative $R^1$ aliphatic hydrocarbon radicals having two bonding sites include, for example, an ethylene radical, a propylene radical, a butylene radical, a pentylene radical, a hexylene radical, a cyclopentylene radical and a cyclohexylene radical. Representative $R^1$ aliphatic hydrocarbon radicals having three or four bonding sites include residues derived from polyalcohols, such as trimethylolpropane, glycerin, pentaerythritol, 1,2,3-trihydroxycyclohexane and 1,3,5-trihydroxycyclohexane, by removing their hydroxyl radicals.

Representative polyoxyalkylene glycol ether solubilizing agents include but are not limited to: $CH_3OCH_2CH(CH_3)$ $O(H$ or $CH_3)$ (propylene glycol methyl (or dimethyl)ether), $CH_3O[CH_2CH(CH_3)O]_2(H$ or $CH_3)$ (dipropylene glycol methyl (or dimethyl)ether), $CH_3O[CH_2CH(CH_3)O]_3(H$ or $CH_3)$ (tripropylene glycol methyl (or dimethyl)ether), $C_2H_5OCH_2CH(CH_3)O(H$ or $C_2H_5)$ (propylene glycol ethyl (or diethyl)ether), $C_2H_5O[CH_2CH(CH_3)O]_2(H$ or $C_2H_5)$ (dipropylene glycol ethyl (or diethyl)ether), $C_2H_5O[CH_2CH(CH_3)O]_3(H$ or $C_2H_5)$ (tripropylene glycol ethyl (or diethyl)ether), $C_3H_7OCH_2CH(CH_3)O(H$ or $C_3H_7)$ (propylene glycol n-propyl (or di-n-propyl)ether), $C_3H_7O[CH_2CH(CH_3)O]_2(H$ or $C_3H_7)$ (dipropylene glycol n-propyl (or di-n-propyl)ether), $C_3H_7O[CH_2CH(CH_3)O]_3(H$ or $C_3H_7)$ (tripropylene glycol n-propyl (or di-n-propyl)ether), $C_4H_9OCH_2CH(CH_3)OH$ (propylene glycol n-butyl ether), $C_4H_9O[CH_2CH(CH_3)O]_2$ (H or $C_4H_9$) (dipropylene glycol n-butyl (or di-n-butyl)ether), $C_4H_9O[CH_2CH(CH_3)O]_3(H$ or $C_4H_9)$ (tripropylene glycol n-butyl (or di-n-butyl)ether), $(CH_3)_3COCH_2CH(CH_3)OH$ (propylene glycol t-butyl ether), $(CH_3)_3CO[CH_2CH(CH_3)O]_2$(H or $(CH_3)_3$) (dipropylene glycol t-butyl (or di-t-butyl) ether), $(CH_3)_3CO[CH_2CH(CH_3)O]_3$(H or $(CH_3)_3$) (tripropylene glycol t-butyl (or di-t-butyl)ether), $C_5H_{11}OCH_2CH(CH_3)OH$ (propylene glycol n-pentyl ether), $C_4H_9OCH_2CH(C_2H_5)OH$ (butylene glycol n-butyl ether), $C_4H_9O[CH_2CH(C_2H_5)O]_2H$ (dibutylene glycol n-butyl ether), trimethylolpropane tri-n-butyl ether $(C_2H_5C(CH_2O(CH_2)_3CH_3)_3)$ and trimethylolpropane di-n-butyl ether $(C_2H_5C(CH_2OC(CH_2)_3CH_3)_2CH_2OH)$.

Amide solubilizing agents of the present invention comprise those represented by the formulae $R^1C(O)NR^2R^3$ and cyclo-$[R^4C(O)N(R^5)]$, wherein $R^1$, $R^2$, $R^3$ and $R^5$ are independently selected from aliphatic and alicyclic hydrocarbon radicals having from 1 to 12 carbon atoms; $R^4$ is selected from aliphatic hydrocarbylene radicals having from 3 to 12 carbon atoms; and wherein said amides have a molecular weight of from about 100 to about 300 atomic mass units. The molecular weight of said amides is preferably from about 160 to about 250 atomic mass units. $R^1$, $R^2$, $R^3$ and $R^5$ may optionally include substituted hydrocarbon radicals, that is, radicals containing non-hydrocarbon substituents selected from halogens (e.g., fluorine, chlorine) and alkoxides (e.g. methoxy). $R^1$, $R^2$, $R^3$ and $R^5$ may optionally include heteroatom-substituted hydrocarbon radicals, that is, radicals, which contain the atoms nitrogen (aza-), oxygen (oxa-) or sulfur (thia-) in a radical chain otherwise composed of carbon atoms. In general, no more than three non-hydrocarbon substituents and heteroatoms, and preferably no more than one, will be present for each 10 carbon atoms in $R^{1-3}$, and the presence of any such non-hydrocarbon substituents and heteroatoms must be considered in applying the aforementioned molecular weight limitations. Preferred amide solubilizing agents consist of carbon, hydrogen, nitrogen and oxygen. Representative $R^1$, $R^2$, $R^3$ and $R^5$ aliphatic and alicyclic hydrocarbon radicals include methyl, ethyl, propyl, isopropyl, butyl, isobutyl, sec-butyl, tert-butyl, pentyl, isopentyl, neopentyl, tert-pentyl, cyclopentyl, cyclohexyl, heptyl, octyl, nonyl, decyl, undecyl, dodecyl and their configurational isomers. A preferred embodiment of amide solubilizing agents are those wherein $R^4$ in the aforementioned formula cyclo-$[R^4C(O)N(R^5)$—] may be represented by the hydrocarbylene radical $(CR^6R^7)_n$, in other words, the formula: cyclo-$[(CR^6R^7)_nC(O)N(R^5)$—] wherein: the previously-stated values for molecular weight apply; n is an integer from 3 to 5; $R^5$ is a saturated hydrocarbon radical containing 1 to 12 carbon atoms; $R^6$ and $R^7$ are independently selected (for each n) by the rules previously offered defining $R^{1-3}$. In the lactams represented by the formula: cyclo-$[(CR^6R^7)_nC(O)N(R^5)$—], all $R^6$ and $R^7$ are preferably hydrogen, or contain a single saturated hydrocarbon radical among the n methylene units, and $R^5$ is a saturated hydrocarbon radical containing 3 to 12 carbon atoms. For example, 1-(saturated hydrocarbon radical)-5-methylpyrrolidin-2-ones.

Representative amide solubilizing agents include but are not limited to: 1-octylpyrrolidin-2-one, 1-decylpyrrolidin-2-one, 1-octyl-5-methylpyrrolidin-2-one, 1-butylcaprolactam, 1-cyclohexylpyrrolidin-2-one, 1-butyl-5-methylpiperid-2-one, 1-pentyl-5-methylpiperid-2-one, 1-hexylcaprolactam, 1-hexyl-5-methylpyrrolidin-2-one, 5-methyl-1-pentylpiperid-2-one, 1,3-dimethylpiperid-2-one, 1-methylcaprolactam, 1-butyl-pyrrolidin-2-one, 1,5-dimethylpiperid-2-one, 1-decyl-5-methylpyrrolidin-2-one, 1-dodecylpyrrolid-2-one, N,N-dibutylformamide and N,N-diisopropylacetamide.

Ketone solubilizing agents of the present invention comprise ketones represented by the formula $R^1C(O)R^2$, wherein $R^1$ and $R^2$ are independently selected from aliphatic, alicyclic and aryl hydrocarbon radicals having from 1 to 12 carbon atoms, and wherein said ketones have a molecular weight of from about 70 to about 300 atomic mass units. $R^1$ and $R^2$ in said ketones are preferably independently selected from aliphatic and alicyclic hydrocarbon radicals having 1 to 9 carbon atoms. The molecular weight of said ketones is preferably from about 100 to 200 atomic mass units. $R^1$ and $R^2$ may together form a hydrocarbylene radical connected and forming a five, six, or seven-membered ring cyclic ketone, for example, cyclopentanone, cyclohexanone, and cycloheptanone. $R^1$ and $R^2$ may optionally include substituted hydrocarbon radicals, that is, radicals containing non-hydrocarbon substituents selected from halogens (e.g., fluorine, chlorine) and alkoxides (e.g. methoxy). $R^1$ and $R^2$ may optionally include heteroatom-substituted hydrocarbon radicals, that is, radicals, which contain the atoms nitrogen (aza-), oxygen (keto-, oxa-) or sulfur (thia-) in a radical chain otherwise composed of carbon atoms. In general, no more than three non-hydrocarbon substituents and heteroatoms, and preferably no more than one, will be present for each 10 carbon atoms in $R^1$ and $R^2$, and the presence of any such non-hydrocarbon substituents and heteroatoms must be considered in applying the aforementioned molecular weight limitations. Representative $R^1$ and $R^2$ aliphatic, alicyclic and aryl hydrocarbon radicals in the general formula $R^1C(O)R^2$ include methyl, ethyl, propyl, isopropyl, butyl, isobutyl, sec-butyl, tert-butyl, pentyl, isopentyl, neopentyl, tert-pentyl, cyclopentyl, cyclohexyl, heptyl, octyl, nonyl, decyl, undecyl, dodecyl and their configurational isomers, as well as phenyl, benzyl, cumenyl, mesityl, tolyl, xylyl and phenethyl.

Representative ketone solubilizing agents include but are not limited to: 2-butanone, 2-pentanone, acetophenone, butyrophenone, hexanophenone, cyclohexanone, cycloheptanone, 2-heptanone, 3-heptanone, 5-methyl-2-hexanone, 2-octanone, 3-octanone, diisobutyl ketone, 4-ethylcyclohexanone, 2-nonanone, 5-nonanone, 2-decanone, 4-decanone, 2-decalone, 2-tridecanone, dihexyl ketone and dicyclohexyl ketone.

Nitrile solubilizing agents of the present invention comprise nitriles represented by the formula $R^1CN$, wherein $R^1$ is selected from aliphatic, alicyclic or aryl hydrocarbon radicals having from 5 to 12 carbon atoms, and wherein said nitriles have a molecular weight of from about 90 to about 200 atomic mass units. $R^1$ in said nitrile solubilizing agents is preferably selected from aliphatic and alicyclic hydrocarbon radicals having 8 to 10 carbon atoms. The molecular weight of said nitrile solubilizing agents is preferably from about 120 to about 140 atomic mass units. $R^1$ may optionally include substituted hydrocarbon radicals, that is, radicals containing non-hydrocarbon substituents selected from halogens (e.g., fluorine, chlorine) and alkoxides (e.g. methoxy). $R^1$ may optionally include heteroatom-substituted hydrocarbon radicals, that is, radicals, which contain the atoms nitrogen (aza-), oxygen (keto-, oxa-) or sulfur (thia-) in a radical chain otherwise composed of carbon atoms. In general, no more than three non-hydrocarbon substituents and heteroatoms, and preferably no more than one, will be present for each 10 carbon atoms in $R^1$, and the presence of any such non-hydrocarbon substituents and heteroatoms must be considered in applying the aforementioned molecular weight limitations. Representative $R^1$ aliphatic, alicyclic and aryl hydrocarbon radicals in the general formula $R^1CN$ include pentyl, isopentyl, neopentyl, tert-pentyl, cyclopentyl, cyclohexyl, heptyl, octyl, nonyl, decyl, undecyl, dodecyl and their configurational isomers, as well as phenyl, benzyl, cumenyl, mesityl, tolyl, xylyl and phenethyl. Representative nitrile solubilizing agents include but are not limited to: 1-cyanopentane, 2,2- dimethyl-4-cyanopentane, 1-cyanohexane, 1-cyanoheptane, 1-cyanooctane, 2-cyanooctane, 1-cyanononane, 1-cyanodecane, 2-cyanodecane, 1-cyanoundecane and 1-cyanododecane.

Chlorocarbon solubilizing agents of the present invention comprise chlorocarbons represented by the formula $RCl_x$, wherein; x is selected from the integers 1 or 2; R is selected from aliphatic and alicyclic hydrocarbon radicals having 1 to 12 carbon atoms; and wherein said chlorocarbons have a molecular weight of from about 100 to about 200 atomic mass units. The molecular weight of said chlorocarbon solubilizing agents is preferably from about 120 to 150 atomic mass units. Representative R aliphatic and alicyclic hydrocarbon radicals in the general formula $RCl_x$ include methyl, ethyl, propyl, isopropyl, butyl, isobutyl, sec-butyl, tert-butyl, pentyl, isopentyl, neopentyl, tert-pentyl, cyclopentyl, cyclohexyl, heptyl, octyl, nonyl, decyl, undecyl, dodecyl and their configurational isomers.

Representative chlorocarbon solubilizing agents include but are not limited to: 3-(chloromethyl)pentane, 3-chloro-3-methylpentane, 1-chlorohexane, 1,6-dichlorohexane, 1-chloroheptane, 1-chlorooctane, 1-chlorononane, 1-chlorodecane, and 1,1,1-trichlorodecane.

Ester solubilizing agents of the present invention comprise esters represented by the general formula $R^1CO_2R^2$, wherein $R^1$ and $R^2$ are independently selected from linear and cyclic, saturated and unsaturated, alkyl and aryl radicals. Preferred esters consist essentially of the elements C, H and O, have a molecular weight of from about 80 to about 550 atomic mass units.

Representative esters include but are not limited to: $(CH_3)_2CHCH_2OOC(CH_2)_{2-4}OCOCH_2CH(CH_3)_2$ (diisobutyl dibasic ester), ethyl hexanoate, ethyl heptanoate, n-butyl propionate, n-propyl propionate, ethyl benzoate, di-n-propyl phthalate, benzoic acid ethoxyethyl ester, dipropyl carbonate, "Exxate 700" (a commercial $C_7$ alkyl acetate), "Exxate 800" (a commercial $C_8$ alkyl acetate), dibutyl phthalate, and tert-butyl acetate.

Lactone solubilizing agents of the present invention comprise lactones represented by structures [A], [B], and [C]:

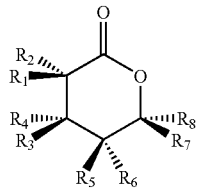
[A]

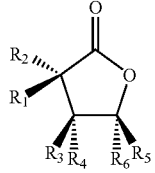
[B]

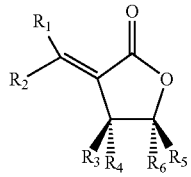
[C]

These lactones contain the functional group $—CO_2—$ in a ring of six (A), or preferably five atoms (B), wherein for structures [A] and [B], $R_1$ through $R_8$ are independently selected from hydrogen or linear, branched, cyclic, bicyclic, saturated and unsaturated hydrocarbyl radicals. Each $R_1$ through $R_8$ may be connected forming a ring with another $R_1$ through $R_8$. The lactone may have an exocyclic alkylidene group as in structure [C], wherein $R_1$ through $R_6$ are independently selected from hydrogen or linear, branched, cyclic, bicyclic, saturated and unsaturated hydrocarbyl radicals. Each $R_1$ though $R_6$ may be connected forming a ring with another $R_1$ through $R_6$. The lactone solubilizing agents have a molecular weight range of from about 80 to about 300 atomic mass units, preferred from about 80 to about 200 atomic mass units.

Representative lactone solubilizing agents include but are not limited to the compounds listed in Table 6.

TABLE 6

| Additive | Molecular Structure | Molecular Formula | Molecular Weight (amu) |
|---|---|---|---|
| (E,Z)-3-ethylidene-5-methyl-dihydro-furan-2-one | 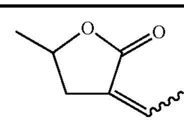 | $C_7H_{10}O_2$ | 126 |
| (E,Z)-3-propylidene-5-methyl-dihydro-furan-2-one | 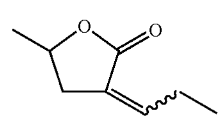 | $C_8H_{12}O_2$ | 140 |
| (E,Z)-3-butylidene-5-methyl-dihydro-furan-2-one | 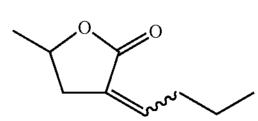 | $C_9H_{14}O_2$ | 154 |
| (E,Z)-3-pentylidene-5-methyl-dihydro-furan-2-one | 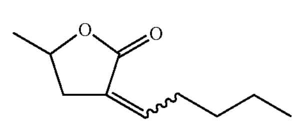 | $C_{10}H_{16}O_2$ | 168 |

TABLE 6-continued

| Additive | Molecular Structure | Molecular Formula | Molecular Weight (amu) |
|---|---|---|---|
| (E,Z)-3-Hexylidene-5-methyl-dihydro-furan-2-one | 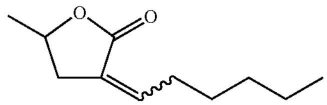 | $C_{11}H_{18}O_2$ | 182 |
| (E,Z)-3-Heptylidene-5-methyl-dihydro-furan-2-one | 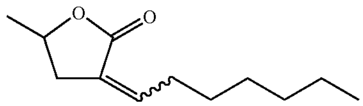 | $C_{12}H_{20}O_2$ | 196 |
| (E,Z)-3-octylidene-5-methyl-dihydro-furan-2-one | 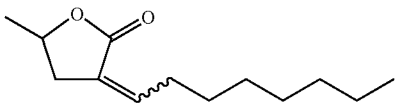 | $C_{13}H_{22}O_2$ | 210 |
| (E,Z)-3-nonylidene-5-methyl-dihydro-furan-2-one | 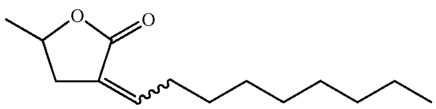 | $C_{14}H_{24}O_2$ | 224 |
| (E,Z)-3-decylidene-5-methyl-dihydro-furan-2-one | 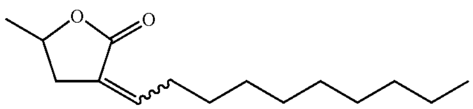 | $C_{15}H_{26}O_2$ | 238 |
| (E,Z)-3-(3,5,5-trimethylhexylidene)-5-methyl-dihydrofuran-2-one | 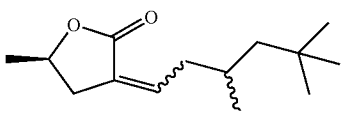 | $C_{14}H_{24}O_2$ | 224 |
| (E,Z)-3-cyclohexylmethylidene-5-methyl-dihydrofuran-2-one | 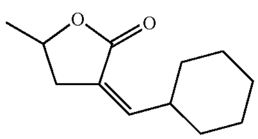 | $C_{12}H_{18}O_2$ | 194 |
| gamma-octalactone | 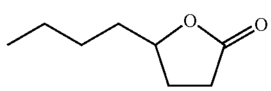 | $C_8H_{14}O_2$ | 142 |
| gamma-nonalactone | 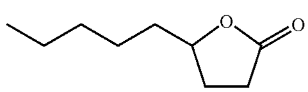 | $C_9H_{16}O_2$ | 156 |
| gamma-decalactone | 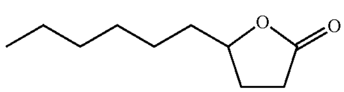 | $C_{10}H_{18}O_2$ | 170 |
| gamma-undecalactone | 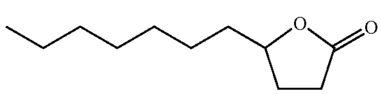 | $C_{11}H_{20}O_2$ | 184 |
| gamma-dodecalactone | 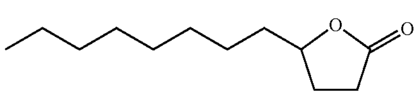 | $C_{12}H_{22}O_2$ | 198 |
| 3-hexyldihydro-furan-2-one | 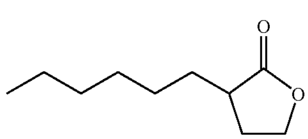 | $C_{10}H_{18}O_2$ | 170 |

TABLE 6-continued

| Additive | Molecular Structure | Molecular Formula | Molecular Weight (amu) |
|---|---|---|---|
| 3-heptyldihydro-furan-2-one | 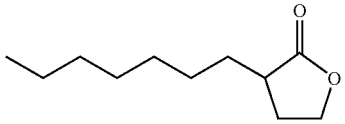 | $C_{11}H_{20}O_2$ | 184 |
| cis-3-ethyl-5-methyl-dihydro-furan-2-one | 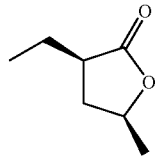 | $C_7H_{12}O_2$ | 128 |
| cis-(3-propyl-5-methyl)-dihydro-furan-2-one | 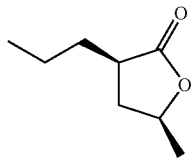 | $C_8H_{14}O_2$ | 142 |
| cis-(3-butyl-5-methyl)-dihydro-furan-2-one | 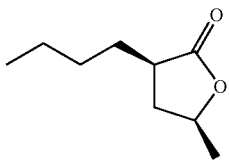 | $C_9H_{16}O_2$ | 156 |
| cis-(3-pentyl-5-methyl)-dihydro-furan-2-one | 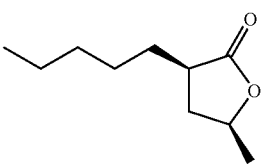 | $C_{10}H_{18}O_2$ | 170 |
| cis-3-hexyl-5-methyl-dihydro-furan-2-one | 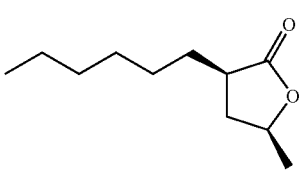 | $C_{11}H_{20}O_2$ | 184 |
| cis-3-heptyl-5-methyl-dihydro-furan-2-one | 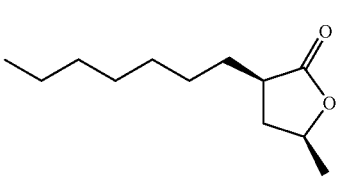 | $C_{12}H_{22}O_2$ | 198 |
| cis-3-octyl-5-methyl-dihydro-furan-2-one | 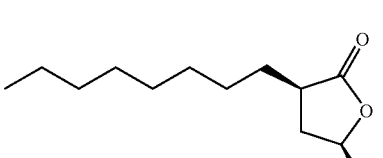 | $C_{13}H_{24}O_2$ | 212 |
| cis-3-(3,5,5-trimethylhexyl)-5-methyl-dihydro-furan-2-one | 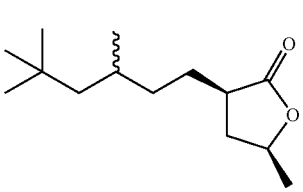 | $C_{14}H_{26}O_2$ | 226 |

TABLE 6-continued

| Additive | Molecular Structure | Molecular Formula | Molecular Weight (amu) |
| --- | --- | --- | --- |
| cis-3-cyclohexylmethyl-5-methyl-dihydro-furan-2-one | 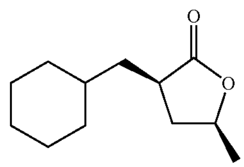 | $C_{12}H_{20}O_2$ | 196 |
| 5-methyl-5-hexyl-dihydro-furan-2-one | 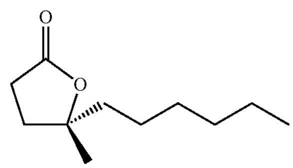 | $C_{11}H_{20}O_2$ | 184 |
| 5-methyl-5-octyl-dihydro-furan-2-one | 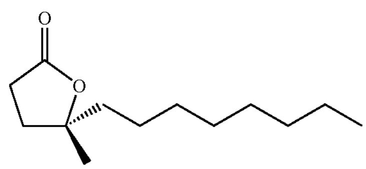 | $C_{13}H_{24}O_2$ | 212 |
| Hexahydro-isobenzofuran-1-one | 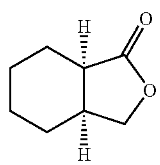 | $C_8H_{12}O_2$ | 140 |
| delta-decalactone | 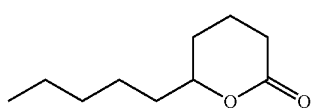 | $C_{10}H_{18}O_2$ | 170 |
| delta-undecalactone | 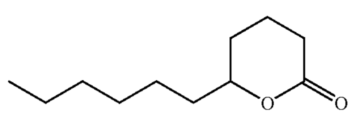 | $C_{11}H_{20}O_2$ | 184 |
| delta-dodecalactone | 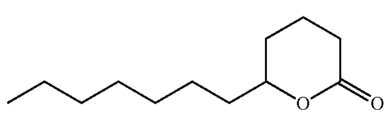 | $C_{12}H_{22}O_2$ | 198 |
| mixture of 4-hexyl-dihydrofuran-2-one and 3-hexyl-dihydro-furan-2-one | 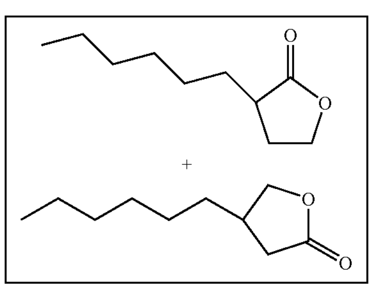 | $C_{10}H_{18}O_2$ | 170 |

Lactone solubilizing agents generally have a kinematic viscosity of less than about 7 centistokes at 40° C. For instance, gamma-undecalactone has kinematic viscosity of 5.4 centistokes and cis-(3-hexyl-5-methyl)dihydrofuran-2-one has viscosity of 4.5 centistokes both at 40° C. Lactone solubilizing agents may be available commercially or prepared by methods as described in U.S. patent application Ser. No. 10/910,495, filed Aug. 3, 2004, incorporated herein by reference.

Aryl ether solubilizing agents of the present invention further comprise aryl ethers represented by the formula $R^1OR^2$, wherein: $R^1$ is selected from aryl hydrocarbon radicals having from 6 to 12 carbon atoms; $R^2$ is selected from aliphatic hydrocarbon radicals having from 1 to 4 carbon atoms; and wherein said aryl ethers have a molecular weight of from about 100 to about 150 atomic mass units. Representative $R^1$ aryl radicals in the general formula $R^1OR^2$ include phenyl, biphenyl, cumenyl, mesityl, tolyl, xylyl, naphthyl and pyridyl. Representative $R^2$ aliphatic hydrocarbon radicals in the general formula $R^1OR^2$ include methyl, ethyl, propyl, isopropyl, butyl, isobutyl, sec-butyl and tert-butyl. Representative aromatic ether solubilizing agents include but are not limited to: methyl phenyl ether (anisole), 1,3-dimethyoxybenzene, ethyl phenyl ether and butyl phenyl ether.

Fluoroether solubilizing agents of the present invention comprise those represented by the general formula $R^1OCF_2CF_2H$, wherein $R^1$ is selected from aliphatic, alicyclic, and aromatic hydrocarbon radicals having from about 5 to about 15 carbon atoms, preferably primary, linear, saturated, alkyl radicals. Representative fluoroether solubilizing agents include but are not limited to: $C_8H_{17}OCF_2CF_2H$ and $C_6H_{13}OCF_2CF_2H$. It should be noted that if the refrigerant is a fluoroether, then the solubilizing agent may not be the same fluoroether.

Fluoroether solubilizing agents may further comprise ethers derived from fluoroolefins and polyols. The fluoroolefins may be of the type $CF_2=CXY$, wherein X is hydrogen, chlorine or fluorine, and Y is chlorine, fluorine, $CF_3$ or $OR_f$, wherein $R_f$ is $CF_3$, $C_2F_5$, or $C_3F_7$. Representative fluoroolefins are tetrafluoroethylene, chlorotrifluoroethylene, hexafluoropropylene, and perfluoromethylvinyl ether. The polyols may be linear or branched. Linear polyols may be of the type $HOCH_2(CHOH)_x(CRR')_yCH_2OH$, wherein R and R' are hydrogen, or $CH_3$, or $C_2H_5$ and wherein x is an integer from 0-4, and y is an integer from 0-4. Branched polyols may be of the type $C(OH)_t(R)_u(CH_2OH)_v[(CH_2)_mCH_2OH]_w$, wherein R may be hydrogen, $CH_3$ or $C_2H_5$, m may be an integer from 0 to 3, t and u may be 0 or 1, v and w are integers from 0 to 4, and also wherein t+u+v+w=4. Representative polyols are trimethylol propane, pentaerythritol, butanediol, and ethylene glycol.

1,1,1-Trifluoroalkane solubilizing agents of the present invention comprise 1,1,1-trifluoroalkanes represented by the general formula $CF_3R^1$, wherein $R^1$ is selected from aliphatic and alicyclic hydrocarbon radicals having from about 5 to about 15 carbon atoms, preferably primary, linear, saturated, alkyl radicals. Representative 1,1,1-trifluoroalkane solubilizing agents include but are not limited to: 1,1,1-trifluorohexane and 1,1,1-trifluorododecane.

Solubilizing agents of the present invention may be present as a single compound, or may be present as a mixture of more than one solubilizing agent. Mixtures of solubilizing agents may contain two solubilizing agents from the same class of compounds, say two lactones, or two solubilizing agents from two different classes, such as a lactone and a polyoxyalkylene glycol ether.

In the present compositions comprising refrigerant and UV fluorescent dye, or comprising heat transfer fluid and UV fluorescent dye, from about 0.001 weight percent to about 1.0 weight percent of the composition is UV dye, preferably from about 0.005 weight percent to about 0.5 weight percent, and most preferably from 0.01 weight percent to about 0.25 weight percent.

Solubility of these UV fluorescent dyes in refrigerant and heat transfer compositions may be poor. Therefore, methods for introducing these dyes into the refrigeration, air-conditioning, or heat pump apparatus have been awkward, costly and time consuming. U.S. Pat. No. RE 36,951, incorporated herein by reference, describes a method, which utilizes a dye powder, solid pellet or slurry of dye that may be inserted into a component of the refrigeration or air-conditioning apparatus. As refrigerant and lubricant are circulated through the apparatus, the dye is dissolved or dispersed and carried throughout the apparatus. Numerous other methods for introducing dye into a refrigeration or air-conditioning apparatus are described in the literature.

Ideally, the UV fluorescent dye could be dissolved in the refrigerant thereby not requiring any specialized method for introduction to the refrigeration, air-conditioning, or heat pump apparatus. The present invention relates to compositions including UV fluorescent dye, which may be introduced into the system dissolved in the refrigerant in combination with a solubilizing agent. The inventive compositions will allow the storage and transport of dye-containing refrigerant and heat transfer fluid even at low temperatures while maintaining the dye in solution.

In the present compositions comprising refrigerant, UV fluorescent dye and solubilizing agent, or comprising heat transfer fluid and UV fluorescent dye and solubilizing agent, from about 1 to about 50 weight percent, preferably from about 2 to about 25 weight percent, and most preferably from about 5 to about 15 weight percent of the combined composition is solubilizing agent in the refrigerant or heat transfer fluid. In the compositions of the present invention the UV fluorescent dye is present in a concentration from about 0.001 weight percent to about 1.0 weight percent in the refrigerant or heat transfer fluid, preferably from 0.005 weight percent to about 0.5 weight percent, and most preferably from 0.01 weight percent to about 0.25 weight percent.

Solubilizing agents such as ketones may have an objectionable odor, which can be masked by addition of an odor masking agent or fragrance. Typical examples of odor masking agents or fragrances may include Evergreen, Fresh Lemon, Cherry, Cinnamon, Peppermint, Floral or Orange Peel, all of which are commercially available, as well as d-limonene and pinene. Such odor masking agents may be used at concentrations of from about 0.001% to as much as about 15% by weight based on the combined weight of odor masking agent and solubilizing agent.

The present invention further relates to a method of using the refrigerant or heat transfer fluid compositions comprising ultraviolet fluorescent dye to detect leaks in refrigeration apparatus, air-conditioning apparatus, or heat pump apparatus. The presence of the dye in the compositions allows for detection of leaking refrigerant in the refrigeration, air-conditioning, or heat pump apparatus. Leak detection helps to one to address, resolve and/or prevent inefficient operation of the apparatus or system or equipment failure. Leak detection also helps one contain chemicals used in the operation of the apparatus.

The method comprises providing the composition comprising refrigerant, ultra-violet fluorescent dye or comprising heat transfer fluid and UV fluorescent dye, as described herein, and optionally, a solubilizing agent as described herein, to refrigeration, air-conditioning, or heat pump apparatus and employing a suitable means for detecting the UV fluorescent dye-containing refrigerant. Suitable means for detecting the dye include, but are not limited to, ultra-violet lamps, often referred to as a "black light" or "blue light". Such ultra-violet lamps are commercially available from numerous sources specifically designed for detecting UV fluorescent dye. Once the ultra-violet fluorescent dye containing composition has been introduced to the refrigeration, air-conditioning, or heat pump apparatus and has been allowed to circulate throughout the system, a leak point or the vicinity of the leak point can be located by shining said ultra-violet lamp on the apparatus and observing the fluorescence of the dye in the vicinity of any leak point.

Mechanical refrigeration is primarily an application of thermodynamics wherein a cooling medium, such as a refrigerant, goes through a cycle so that it can be recovered for reuse. Commonly used cycles include vapor-compression, absorption, steam-jet or steam-ejector, and air.

Vapor-compression refrigeration systems include an evaporator, a compressor, a condenser, and an expansion device. A vapor-compression cycle re-uses refrigerant in multiple steps producing a cooling effect in one step and a heating effect in a different step. The cycle can be described simply as follows. Liquid refrigerant enters an evaporator through an expansion device, and the liquid refrigerant boils in the evaporator at a low temperature to form a gas and produce cooling. The low-pressure gas enters a compressor where the gas is compressed to raise its pressure and temperature. The higher-pressure (compressed) gaseous refrigerant then enters the condenser in which the refrigerant condenses and discharges its heat to the environment. The refrigerant returns to the expansion device through which the liquid expands from the higher-pressure level in the condenser to the low-pressure level in the evaporator, thus repeating the cycle.

There are various types of compressors that may be used in refrigeration applications. Compressors can be generally classified as reciprocating, rotary, jet, centrifugal, scroll, screw or axial-flow, depending on the mechanical means to compress the fluid, or as positive-displacement (e.g., reciprocating, scroll or screw) or dynamic (e.g., centrifugal or jet), depending on how the mechanical elements act on the fluid to be compressed.

The compositions of the present invention comprising fluoroolefins may be useful in any of the compressor types mentioned above. The choice of refrigerant for any given compressor will depend on many factors including for instance, boiling point and vapor pressure requirements.

Either positive displacement or dynamic compressors may be used in the present inventive processes. A centrifugal type compressor is one preferred type of equipment for certain of the refrigerant compositions comprising at least one fluoroolefin.

A centrifugal compressor uses rotating elements to accelerate the refrigerant radially, and typically includes an impeller and diffuser housed in a casing. Centrifugal compressors usually take fluid in at an impeller eye, or central inlet of a circulating impeller, and accelerate it radially outward. Some static pressure rise occurs in the impeller, but most of the pressure rise occurs in the diffuser section of the casing, where velocity is converted to static pressure. Each impeller-diffuser set is a stage of the compressor. Centrifugal compressors are built with from 1 to 12 or more stages, depending on the final pressure desired and the volume of refrigerant to be handled.

The pressure ratio, or compression ratio, of a compressor is the ratio of absolute discharge pressure to the absolute inlet pressure. Pressure delivered by a centrifugal compressor is practically constant over a relatively wide range of capacities.

Positive displacement compressors draw vapor into a chamber, and the chamber decreases in volume to compress the vapor. After being compressed, the vapor is forced from the chamber by further decreasing the volume of the chamber to zero or nearly zero. A positive displacement compressor can build up a pressure, which is limited only by the volumetric efficiency and the strength of the parts to withstand the pressure.

Unlike a positive displacement compressor, a centrifugal compressor depends entirely on the centrifugal force of the high-speed impeller to compress the vapor passing through the impeller. There is no positive displacement, but rather what is called dynamic-compression.

The pressure a centrifugal compressor can develop depends on the tip speed of the impeller. Tip speed is the speed of the impeller measured at its tip and is related to the diameter of the impeller and its revolutions per minute. The capacity of the centrifugal compressor is determined by the size of the passages through the impeller. This makes the size of the compressor more dependent on the pressure required than the capacity.

Because of its high-speed operation, a centrifugal compressor is fundamentally a high volume, low-pressure machine. A centrifugal compressor works best with a low-pressure refrigerant, such as trichlorofluoromethane (CFC-11) or 1,2,2-trichlorotrifluoroethane (CFC-113). Some of the low pressure refrigerant fluids of the present invention may be suitable as drop-in replacements for CFC-113 in existing centrifugal equipment.

Large centrifugal compressors typically operate at 3000 to 7000 revolutions per minute (rpm). Small turbine centrifugal compressors (mini-centrifugal compressors) are designed for high speeds, from about 40,000 to about 70,000 (rpm), and have small impeller sizes, typically less than 0.15 meters (about 6 inches).

A multi-stage impeller may be used in a centrifugal compressor to improve compressor efficiency thus requiring less power in use. For a two-stage system, in operation, the discharge of the first stage impeller goes to the suction intake of a second impeller. Both impellers may operate by use of a single shaft (or axle). Each stage can build up a compression ratio of about 4 to 1; that is, the absolute discharge pressure can be four times the absolute suction pressure. Several examples of two-stage centrifugal compressor systems, particularly for automotive applications, are described in U.S. Pat. No. 5,065,990 and U.S. Pat. No. 5,363,674, both incorporated herein by reference.

The present disclosure further relates to a method for producing heating or cooling in a refrigeration, air-conditioning, or heat pump apparatus, said method comprising introducing a refrigerant or heat transfer fluid composition into said apparatus having (a) a centrifugal compressor; (b) a multi-stage centrifugal compressor, or (c) a single slab/single pass heat exchanger; wherein said refrigerant or heat transfer fluid composition comprises at least one fluoroolefin selected from the group consisting of:

(i) fluoroolefins of the formula E- or Z—$R^1CH=CHR^2$, wherein $R^1$ and $R^2$ are, independently, $C_1$ to $C_6$ perfluoroalkyl groups;

(ii) cyclic fluoroolefins of the formula cyclo-[CX=CY(CZW)$_n$—], wherein X, Y, Z, and W, independently, are H or F, and n is an integer from 2 to 5; or (iii) fluoroolefins selected from the group consisting of: 1,2,3,3,3-pentafluoro-1-propene ($CF_3CF=CHF$); 1,1,3,3,3-pentafluoro-1-propene ($CF_3CH=CF_2$); 1,1,2,3,3-pentafluoro-1-propene ($CHF_2CF=CF_2$); 1,2,3,3,3-tetrafluoro-1-propene ($CF_3CF=CHF$); 2,3,3,3-tetrafluoro-1-propene ($CF_3CF=CH_2$); 1,3,3,3-tetrafluoro-1-propene ($CF_3CH=CHF$); 1,1,2,3-tetrafluoro-1-propene ($CH_2FCF=CF_2$); 1,1,3,3-tetrafluoro-1-propene ($CHF_2CH=CF_2$); 2,3,3-trifluoro-1-propene ($CHF_2CF=CH_2$); 3,3,3-trifluoro-1-propene ($CF_3CH=CH_2$); 1,1,2-trifluoro-1-propene ($CH_3CF=CF_2$); 1,1,3-trifluoro-1-propene ($CH_2FCH=CF_2$); 1,2,3-trifluoro-1-propene ($CH_2FCF=CHF$); 1,3,3-trifluoro-1-propene ($CHF_2CH=CHF$); 1,1,1,2,3,4,4,4-octafluoro-2-butene ($CF_3CF=CFCF_3$); 1,1,2,3,3,4,4,4-octafluoro-1-butene ($CF_3CF_2CF=CF_2$); 1,1,1,2,4,4,4-heptafluoro-2-butene ($CF_3CF=CHCF_3$); 1,2,3,3,4,4,4-heptafluoro-1-butene ($CHF=CFCF_2CF_3$); 1,1,1,2,3,4,4-heptafluoro-2-butene ($CHF_2CF=CFCF_3$); 1,3,3,3-tetrafluoro-2-(trifluoromethyl)-1-propene (($CF_3)_2C=CHF$); 1,1,3,3,4,4,4-heptafluoro-1-butene ($CF_2=CHCF_2CF_3$); 1,1,2,3,4,4,4-heptafluoro-1-butene ($CF_2=CFCHFCF_3$); 1,1,2,3,3,4,4-heptafluoro-1-butene ($CF_2=CFCF_2CHF_2$); 2,3,3,4,4,4-hexafluoro-1-butene ($CF_3CF_2CF=CH_2$); 1,3,3,4,4,4-hexafluoro-1-butene ($CHF=CHCF_2CF_3$); 1,2,3,4,4,4-hexafluoro-1-butene ($CHF=CFCHFCF_3$); 1,2,3,3,4,4-hexafluoro-1-butene ($CHF=CFCF_2CHF_2$); 1,1,2,3,4,4-hexafluoro-2-butene ($CHF_2CF=CFCHF_2$); 1,1,1,2,3,4-hexafluoro-2-butene ($CH_2FCF=CFCF_3$); 1,1,1,2,4,4-hexafluoro-2-butene ($CHF_2CH=CFCF_3$); 1,1,1,3,4,4-hexafluoro-2-butene ($CF_3CH=CFCHF_2$); 1,1,2,3,3,4-hexafluoro-1-butene ($CF_2=CFCF_2CH_2F$); 1,1,2,3,4,4-hexafluoro-1-butene ($CF_2=CFCHFCHF_2$); 3,3,3-trifluoro-2-(trifluoromethyl)-1-propene ($CH_2=C(CF_3)_2$); 1,1,1,2,4-pentafluoro-2-butene ($CH_2FCH=CFCF_3$); 1,1,1,3,4-pentafluoro-2-butene ($CF_3CH=CFCH_2F$); 3,3,4,4,4-pentafluoro-1-butene ($CF_3CF_2CH=CH_2$); 1,1,1,4,4-pentafluoro-2-butene ($CHF_2CH=CHCF_3$); 1,1,1,2,3-pentafluoro-2-butene ($CH_3CF=CFCF_3$); 2,3,3,4,4-pentafluoro-1-butene ($CH_2=CFCF_2CHF_2$); 1,1,2,4,4-pentafluoro-2-butene ($CHF_2CF=CHCHF_2$); 1,1,2,3,3-pentafluoro-1-butene ($CH_3CF_2CF=CF_2$); 1,1,2,3,4-pentafluoro-2-butene ($CH_2FCF=CFCHF_2$); 1,1,3,3,3-pentafluoro-2-methyl-1-propene ($CF_2=C(CF_3)(CH_3)$); 2-(difluoromethyl)-3,3,3-trifluoro-1-propene ($CH_2=C(CHF_2)(CF_3)$); 2,3,4,4,4-pentafluoro-1-butene ($CH_2=CFCHFCF_3$); 1,2,4,4,4-pentafluoro-1-butene ($CHF=CFCH_2CF_3$); 1,3,4,4,4-pentafluoro-1-butene ($CHF=CHCHFCF_3$); 1,3,3,4,4-pentafluoro-1-butene ($CHF=CHCF_2CHF_2$); 1,2,3,4,4-pentafluoro-1-butene ($CHF=CFCHFCHF_2$); 3,3,4,4-tetrafluoro-1-butene ($CH_2=CHCF_2CHF_2$); 1,1-difluoro-2-(difluoromethyl)-1-propene ($CF_2=C(CHF_2)(CH_3)$); 1,3,3,3-tetrafluoro-2-methyl-1-propene ($CHF=C(CF_3)(CH_3)$); 2-difluoromethyl-3,3-difluoro-1-propene ($CH_2=C(CHF_2)_2$); 1,1,1,2-tetrafluoro-2-butene ($CF_3CF=CHCH_3$); 1,1,1,3-tetrafluoro-2-butene ($CH_3CF=CHCF_3$); 1,1,1,2,3,4,4,5,5-decafluoro-2-pentene ($CF_3CF=CFCF_2CF_3$); 1,1,2,3,3,4,4,5,5-decafluoro-1-pentene ($CF_2=CFCF_2CF_2CF_3$); 1,1,1,4,4,4-hexafluoro-2-(trifluoromethyl)-2-butene (($CF_3)_2C=CHCF_3$); 1,1,1,2,4,4,5,5,5-nonafluoro-2-pentene ($CF_3CF=CHCF_2CF_3$); 1,1,1,3,4,4,5,5,5-nonafluoro-2-pentene ($CF_3CH=CFCF_2CF_3$); 1,2,3,3,4,4,5,5,5-nonafluoro-1-pentene ($CHF=CFCF_2CF_2CF_3$); 1,1,3,3,4,4,5,5-nonafluoro-1-pentene ($CF_2=CHCF_2CF_2CF_3$); 1,1,2,3,3,4,4,5,5-nonafluoro-1-pentene ($CF_2=CFCF_2CF_2CHF_2$); 1,1,2,3,4,4,5,5,5-nonafluoro-2-pentene ($CHF_2CF=CFCF_2CF_3$); 1,1,1,2,3,4,4,5,5-nonafluoro-2-pentene ($CF_3CF=CFCF_2CHF_2$); 1,1,1,2,3,4,5,5,5-nonafluoro-2-pentene ($CF_3CF=CFCHFCF_3$); 1,2,3,4,4,4-hexafluoro-3-(trifluoromethyl)-1-butene ($CHF=CFCF(CF_3)_2$); 1,1,2,4,4,4-hexafluoro-3-(trifluoromethyl)-1-butene ($CF_2=CFCH(CF_3)_2$); 1,1,1,4,4,4-hexafluoro-2-(trifluoromethyl)-2-butene ($CF_3CH=C(CF_3)_2$); 1,1,3,4,4,4-hexafluoro-3-(trifluoromethyl)-1-butene ($CF_2=CHCF(CF_3)_2$); 2,3,3,4,4,5,5,5-octafluoro-1-pentene ($CH_2=CFCF_2CF_2CF_3$); 1,2,3,3,4,4,5,5-octafluoro-1-pentene ($CHF=CFCF_2CF_2CHF_2$); 3,3,4,4,4-pentafluoro-2-(trifluoromethyl)-1-butene ($CH_2=C(CF_3)CF_2CF_3$); 1,1,4,4,4-pentafluoro-3-(trifluoromethyl)-1-butene ($CF_2=CHCH(CF_3)_2$); 1,3,4,4,4-pentafluoro-3-(trifluoromethyl)-1-butene ($CHF=CHCF(CF_3)_2$); 1,1,4,4,4-pentafluoro-2-(trifluoromethyl)-1-butene ($CF_2=C(CF_3)CH_2CF_3$); 3,4,4,4-tetrafluoro-3-(trifluoromethyl)-1-butene (($CF_3)_2CFCH=CH_2$); 3,3,4,4,5,5,5-heptafluoro-1-pentene ($CF_3CF_2CF_2CH=CH_2$); 2,3,3,4,4,5,5-heptafluoro-1-pentene ($CH_2=CFCF_2CF_2CHF_2$); 1,1,3,3,5,5,5-heptafluoro-1-butene ($CF_2=CHCF_2CH_2CF_3$); 1,1,1,2,4,4,4-heptafluoro-3-methyl-2-butene ($CF_3CF=C(CF_3)(CH_3)$); 2,4,4,4-tetrafluoro-3-(trifluoromethyl)-1-butene ($CH_2=CFCH(CF_3)_2$); 1,4,4,4-tetrafluoro-3-(trifluoromethyl)-1-butene ($CHF=CHCH(CF_3)_2$); 1,1,1,4-tetrafluoro-2-(trifluoromethyl)-2-butene ($CH_2FCH=C(CF_3)_2$); 1,1,1,3-tetrafluoro-2-(trifluoromethyl)-2-butene ($CH_3CF=C(CF_3)_2$); 1,1,1-trifluoro-2-(trifluoromethyl)-2-butene (($CF_3)_2C=CHCH_3$); 3,4,4,5,5,5-hexafluoro-2-pentene ($CF_3CF_2CF=CHCH_3$); 1,1,1,4,4,4-hexafluoro-2-methyl-2-butene ($CF_3C(CH_3)=CHCF_3$); 3,3,4,5,5,5-hexafluoro-1-pentene ($CH_2=CHCF_2CHFCF_3$); 3-(trifluoromethyl)-4,4,4-trifluoro-1-butene ($CH_2=C(CF_3)CH_2CF_3$); 1,1,2,3,3,4,4,5,5,6,6,6-dodecafluoro-1-hexene ($CF_3(CF_2)_3CF=CF_2$); 1,1,1,2,2,3,4,5,5,6,6,6-dodecafluoro-3-hexene ($CF_3CF_2CF=CFCF_2CF_3$); 1,1,1,4,4,4-hexafluoro-2,3-bis(trifluoromethyl)-2-butene (($CF_3)_2C=C(CF_3)_2$); 1,1,1,2,3,4,5,5,5-nonafluoro-4-(trifluoromethyl)-2-pentene (($CF_3)_2CFCF=CFCF_3$); 1,1,1,4,4,5,5,5-octafluoro-2-(trifluoromethyl)-2-pentene (($CF_3)_2C=CHC_2F_5$); 1,1,1,3,4,5,5,5-octafluoro-4-(trifluoromethyl)-2-pentene (($CF_3)_2CFCF=CHCF_3$); 3,3,4,4,5,5,6,6-nonafluoro-1-hexene ($CF_3CF_2CF_2CH=CH_2$); 4,4,4-trifluoro-3,3-bis(trifluoromethyl)-1-butene ($CH_2=CHC(CF_3)_3$); 1,1,1,4,4,4-hexafluoro-3-methyl-2-(trifluoromethyl)-2-butene (($CF_3)_2C=C(CH_3)(CF_3)$); 2,3,3,5,5,5-hexafluoro-4-(trifluoromethyl)-1-pentene ($CH_2=CFCF_2CH(CF_3)_2$); 1,1,1,2,4,4,5,5,5-nonafluoro-3-methyl-2-pentene ($CF_3CF=C(CH_3)CF_2CF_3$); 1,1,1,5,5,5-hexafluoro-4-(trifluoromethyl)-2-pentene ($CF_3CH=CHCH(CF_3)_2$); 3,4,4,5,5,6,6,6-octafluoro-2-hexene ($CF_3CF_2CF_2CF=CHCH_3$); 3,3,4,4,5,5,6,6-octafluoro-1-hexene ($CH_2=CHCF_2CF_2CF_2CHF_2$); 1,1,1,4,4-pentafluoro-2-(trifluoromethyl)-2-pentene (($CF_3)_2C=CHCF_2CH_3$); 4,4,5,5-pentafluoro-2-(trifluoromethyl)-1-pentene ($CH_2=C(CF_3)CH_2C_2F_5$); 3,3,4,4,5,5,5-heptafluoro-2-methyl-1-pentene ($CF_3CF_2CF_2C(CH_3)=CH_2$); 4,4,5,5,6,6,6-heptafluoro-2-hexene ($CF_3CF_2CF_2CH=CHCH_3$); 4,4,5,5,6,6,6-heptafluoro-1-hexene ($CH_2=CHCH_2CF_2C_2F_5$); 1,1,1,2,2,3,4-heptafluoro-3-hexene ($CF_3CF_2CF=CFC_2H_5$); 4,5,5,5-tetrafluoro-4-trifluoromethyl-1-pentene ($CH_2=CHCH_2CF(CF_3)_2$); 1,1,1,2,5,5,5-heptafluoro-4-methyl-2-pentene ($CF_3CF=CHCH(CF_3)(CH_3)$); 1,1,1,3-tetrafluoro-2-trifluoromethyl-2-pentene (($CF_3)_2C=CFC_2H_5$); 1,1,1,2,3,4,4,5,5,6,6,7,7,7-tetradecafluoro-2-heptene ($CF_3CF\!=\!CFCF_2C_2F_5$); 1,1,1,2,2,3,4,5,5,6,6,7,7,7-tetradecafluoro-3-heptene ($CF_3CF_2CF\!=\!CFCF_2C_2F_5$); 1,1,1,3,4,4,5,5,6,6,7,7,7-tridecafluoro-2-heptene ($CF_3CH\!=\!CFCF_2CF_2C_2F_5$); 1,1,1,2,4,4,5,5,6,6,7,7,7-tridecafluoro-2-heptene ($CF_3CF\!=\!CHCF_2CF_2C_2F_5$); 1,1,1,2,2,4,5,5,6,6,7,7,7-tridecafluoro-3-heptene ($CF_3CF_2CH\!=\!CFCF_2C_2F_5$); 1,1,1,2,2,3,5,5,6,6,7,7,7-tridecafluoro-3-heptene ($CF_3CF_2CF\!=\!CHCF_2C_2F_5$); $CF_2\!=\!CFOCF_2CF_3$ (PEVE); $CF_2\!=\!CFOCF_3$ (PMVE) and combinations thereof.

The method for producing heating or cooling may be used in stationary air-conditioning, heat pumps or mobile air-conditioning and refrigeration systems. Stationary air-conditioning and heat pump applications include window, ductless, ducted, packaged terminal, chillers and commercial, including packaged rooftop. Refrigeration applications include domestic or home refrigerators and freezers, ice machines, self-contained coolers and freezers, walk-in coolers and freezers and transport refrigeration systems.

The compositions of the present invention may additionally be used in air-conditioning, heating and refrigeration systems that employ fin and tube heat exchangers, microchannel heat exchangers and vertical or horizontal single pass tube or plate type heat exchangers.

Conventional microchannel heat exchangers may not be ideal for the low pressure refrigerant compositions of the present invention. The low operating pressure and density result in high flow velocities and high frictional losses in all components. In these cases, the evaporator design may be modified. Rather than several microchannel slabs connected in series (with respect to the refrigerant path) a single slab/single pass heat exchanger arrangement may be used. Therefore, a preferred heat exchanger for the refrigerant or heat transfer fluid compositions of the present invention is a single slab/single pass heat exchanger.

The present invention further relates to a process for producing cooling comprising evaporating the fluoroolefin compositions of the present invention in the vicinity of a body to be cooled, and thereafter condensing said compositions.

The present invention further relates to a process for producing heat comprising condensing the fluoroolefin compositions of the present invention in the vicinity of a body to be heated, and thereafter evaporating said compositions.

The present invention further relates to a process to produce cooling comprising compressing a composition comprising at least one fluoroolefin in a centrifugal compressor, condensing said composition, and thereafter evaporating said composition in the vicinity of a body to be cooled. Additionally, the centrifugal compressor of the inventive method may be a multi-stage centrifugal compressor and preferably a 2-stage centrifugal compressor.

The present invention further relates to a process to produce cooling in a refrigeration apparatus, air-conditioning apparatus, or heat pump apparatus, wherein said apparatus comprises at least one single slab/single pass heat exchanger, said process comprising condensing a composition of the present invention, and thereafter evaporating said composition in the vicinity of a body to be cooled.

The compositions of the present invention are particularly useful in small turbine centrifugal compressors (mini-centrifugal compressors), which can be used in auto and window air-conditioning, heat pumps, or transport refrigeration, as well as other applications. These high efficiency mini-centrifugal compressors may be driven by an electric motor and can therefore be operated independently of the engine speed. A constant compressor speed allows the system to provide a relatively constant cooling capacity at all engine speeds. This provides an opportunity for efficiency improvements especially at higher engine speeds as compared to a conventional R-134a automobile air-conditioning system. When the cycling operation of conventional systems at high driving speeds is taken into account, the advantage of these low pressure systems becomes even greater.

Alternatively, rather than use electrical power, the mini-centrifugal compressor may be powered by an engine exhaust gas driven turbine or a ratioed gear drive assembly with ratioed belt drive. The electrical power available in current automobile design is about 14 volts, but the new mini-centrifugal compressor requires electrical power of about 50 volts. Therefore, use of an alternative power source would be advantageous. A refrigeration apparatus or air-conditioning apparatus powered by an engine exhaust gas driven turbine is described in detail in U.S. patent application Ser. No. 11/367,517, filed Mar. 3, 2006. A refrigeration apparatus or air-conditioning apparatus powered by a ratioed gear drive assembly is described in detail in U.S. patent application Ser. No. 11/378,832, filed Mar. 17, 2006.

The present invention further relates to a process to produce cooling comprising compressing a composition of the present invention, in a mini-centrifugal compressor powered by an engine exhaust gas driven turbine; condensing said composition; and thereafter evaporating said composition in the vicinity of a body to be cooled.

The present invention further relates to a process to produce cooling comprising compressing a composition of the present invention, in a mini-centrifugal compressor powered by a ratioed gear drive assembly with a ratioed belt drive; condensing said composition; and thereafter evaporating said composition in the vicinity of a body to be cooled.

The present invention relates to a process to produce cooling in a refrigeration apparatus, air-conditioning apparatus, or heat pump apparatus, wherein said apparatus comprises at least one single slab/single pass heat exchanger, said process comprising compressing a composition of the present invention, in a centrifugal compressor, condensing said composition, and thereafter evaporating said composition in the vicinity of a body to be cooled.

The present invention further relates to a method for replacing or substituting for a refrigerant composition having a GWP of about 150 or more, or a high GWP refrigerant, with a composition having a lower GWP. One method comprises providing a composition comprising at least one fluoroolefin of the present invention as the replacement. In another embodiment of the present invention the refrigerant or heat transfer fluid composition of the present invention, having a lower GWP than the composition being replaced or substituted is introduced into the refrigeration, air conditioning or heat pump apparatus. In some cases, the high GWP refrigerant present in the apparatus will need to be removed from the apparatus before introduction of the lower GWP compositions. In other cases, the fluoroolefin compositions of the present invention may be introduced into the apparatus while the high GWP refrigerant is present.

Global warming potentials (GWPs) are an index for estimating relative global warming contribution due to atmospheric emission of a kilogram of a particular greenhouse gas compared to emission of a kilogram of carbon dioxide. GWP can be calculated for different time horizons showing the effect of atmospheric lifetime for a given gas. The GWP for the 100 year time horizon is commonly the value referenced.

A high GWP refrigerant would be any compound capable of functioning as a refrigerant or heat transfer fluid having a GWP at the 100 year time horizon of about 1000 or greater, alternatively 500 or greater, 150 or greater, 100 or greater, or 50 or greater. Refrigerants and heat transfer fluids that are in need of replacement, based upon GWP calculations published by the Intergovernmental Panel on Climate Change (IPCC), include but are not limited to HFC-134a (1,1,1,2-tetrafluoroethane).

The present invention will provide compositions that have zero or low ozone depletion potential and low global warming potential (GWP). The fluoroolefins of the present invention or mixtures of fluoroolefins of this invention with other refrigerants will have global warming potentials that are less than many hydrofluorocarbon refrigerants currently in use. Typically, the fluoroolefins of the present invention are expected to have GWP of less than about 25. One aspect of the present invention is to provide a refrigerant with a global warming potential of less than 1000, less than 500, less than 150, less than 100, or less than 50. Another aspect of the present invention is to reduce the net GWP of refrigerant mixtures by adding fluoroolefins to said mixtures.

The present invention further relates to a method for lowering the GWP of a refrigerant or heat transfer fluid, said method comprising combining said refrigerant or heat transfer fluid with at least one fluoroolefin of the present invention. In another embodiment, the method for lowering the global warming potential comprises combining said first composition with a composition comprising at least one fluorolefin, to produce a second composition suitable for use as a refrigerant or heat transfer fluid, and wherein said second composition has a lower global warming potential than said first composition. It may be determined that the GWP of a mixture or combination of compounds may be calculated as a weighted average of the GWP for each of the pure compounds.

The present invention further relates to a method of using the composition of the present invention comprising at least one fluoroolefin to lower global warming potential of an original refrigerant or heat transfer fluid composition, said method comprising combining said original refrigerant or heat transfer fluid composition with the composition of the present invention comprising at least one fluoroolefin, to produce a second refrigerant or heat transfer fluid composition wherein said second refrigerant or heat transfer fluid composition has a lower global warming potential than said original refrigerant or heat transfer fluid composition.

The present invention further relates to a method for reducing the GWP of an original refrigerant or heat transfer fluid composition in a refrigeration, air-conditioning or heat pump apparatus, wherein said original refrigerant or heat transfer fluid has a GWP of about 150 or higher; said method comprising introducing a second, lower GWP refrigerant or heat transfer fluid composition of the present invention into said refrigeration, air-conditioning or heat pump apparatus.

The present method for reducing the GWP of an original refrigerant may further comprise removing the original refrigerant or heat transfer fluid composition from said refrigeration, air-conditioning or heat pump apparatus before the second, lower GWP refrigerant or heat transfer fluid is introduced.

The present invention further relates to a method for replacing an original refrigerant or heat transfer fluid composition with a second refrigerant or heat transfer fluid composition comprising providing a composition of the present invention as the second refrigerant or heat transfer fluid composition. An original refrigerant may be any refrigerant being used in a refrigeration, air-conditioning or heat pump apparatus in need of replacement The original refrigerant or heat transfer fluid needing replacement may be any of hydrofluorocarbon refrigerants, chlorofluorocarbon refrigerants, hydrochlorofluorocarbon, refrigerants, fluoroether refrigerants, or blends of refrigerant compounds.

The hydrofluorocarbon refrigerants of the present invention which may need replacing include but are not limited to: $CHF_3$ (HFC-23), $CH_2F_2$ (HFC-32), $CH_3F$ (HFC-41), $CHF_2CF_3$ (HFC-125), $CHF_2CHF_2$ (HFC-134), $CH_2FCF_3$ (HFC-134a), $CHF_2CH_2F$ (HFC143), $CF_3CH_3$ (HFC-143a), $CHF_2CH_3$ (HFC-152a), $CH_2FCH_3$ (HFC-161), $CHF_2CF_2CF_3$ (HFC-227ca), $CF_3CFHCF_3$ (HFC-227ea), $CHF_2CF_2CHF_2$ (HFC-236ca), $CH_2FCF_2CF_3$ (HFC-236cb), $CHF_2CHFCF_3$ (HFC-236ea), $CF_3CH_2CF_3$ (HFC-236fa), $CH_2FCF_2CHF_2$ (HFC-245ca), $CH_3CF_2CF_3$ (HFC-245cb), $CHF_2CHFCHF_2$ (HFC-245ea), $CH_2FCHFCF_3$ (HFC-245eb), $CHF_2CH_2CF_3$ (HFC-245fa), $CH_2FCF_2CH_2F$ (HFC-254ca), $CH_3CF_2CHF_2$ (HFC-254cb), $CH_2FCHFCHF_2$ (HFC-254ea), $CH_3CHFCF_3$ (HFC-254eb), $CHF_2CH_2CHF_2$ (HFC-254fa), $CH_2FCH_2CF_3$ (HFC-254fb), $CF_3CH_2CH_3$ (HFC-263fb), $CH_3CF_2CH_2F$ (HFC-263ca), $CH_3CF_2CH_3$ (HFC-272ca), $CH_3CHFCH_2F$ (HFC-272ea), $CH_2FCH_2CH_2F$ (HFC-272fa), $CH_3CH_2CF_2H$(HFC-272fb), $CH_3CHFCH_3$ (HFC-281ea), $CH_3CH_2CH_2F$ (HFC-281fa), $CHF_2CF_2CF_2CF_2H$(HFC-338 pcc), $CF_3CH_2CF_2CH_3$ (HFC-365mfc), $CF_3CHFCHFCF_2CF_3$ (HFC-43-10mee). These hydrofluorocarbon refrigerants are available commercially or may be prepared by methods known in the art.

Hydrofluorocarbon refrigerants of the present invention may further comprise the azeotropic, azeotrope-like and non-azeotropic compositions, including HFC-125/HFC-143a/HFC-134a (known by the ASHRAE designation, R404 or R404A), HFC-32/HFC-125/HFC-134a (known by ASHRAE designations, R407 or R407A, R407B, or R407C), HFC-32/HFC-125 (R410 or R410A), and HFC-125/HFC-143a (known by the ASHRAE designation: R507 or R507A), R413A (a blend of R134a/R218/isobutane), R423A (a blend of R134a/R227ea), R507A (a blend of R125/R143a), and others.

Chlorofluorocarbon refrigerants of the present invention which may need replacing include R22 ($CHF_2Cl$), R123 ($CHCl_2CF_3$), R124 ($CHClFCF_3$), R502 (being a blend of CFC-115 ($CClF_2CF_3$) and R22), R503 (being a blend of R23/R13 ($CClF_3$)), and others.

Hydrochlorofluorocarbons of the present invention which may need replacing include R12 ($CF_2Cl_2$), R11 ($CCl_3F$), R113 ($CCl_2FCClF_2$), R114 ($CF_2ClCF_2Cl$), R401A or R401B (being blends of R22/R152a/R124), R408A (a blend of R22/R125/R143a), and others.

The fluoroether refrigerants of the present invention which may need replacing may comprise compounds similar to hydrofluorocarbons, which also contain at least one ether group oxygen atom. The fluoroether refrigerants include but are not limited to $C_4F_9OCH_3$, and $C_4F_9OC_2H_5$ (both available commercially).

The original refrigerant or heat transfer fluid compositions of the present invention which may need replacement may optionally further comprise combinations of refrigerants that contain up to 10 weight percent of dimethyl ether, or at least one $C_3$ to $C_5$ hydrocarbon, e.g., propane, propylene, cyclopropane, n-butane, isobutane, n-pentane, cyclopentane and neopentane (2,2-dimethylpropane). Examples of refrigerants containing such $C_3$ to $C_5$ hydrocarbons are azeotrope-like compositions of HCFC-22/HFC-125/propane (known by the ASHRAE designation, R402 or R402A and R402B), HCFC-22/octafluoropropane/propane (known by the ASHRAE designation, R403 or R403A and R403B), octafluoropropane/HFC-134a/isobutane (known by the ASHRAE designation, R413 or R413A), HCFC-22/HCFC-124/HCFC-142b/isobutane (known by the ASHRAE designation, R414 or R414A and R414B), HFC-134a/HCFC-124/n-butane (known by the ASHRAE designation, R416 or R416A), HFC-125/HFC-134a/n-butane (known by the ASHRAE designation, R417 or R417A), HFC-125/HFC-134a/dimethyl ether (known by the ASHRAE designation, R419 or R419A), and HFC-125/HFC-134a/isobutane (known by ASHRAE designation, R422, R422A, R422B, R422C, R422D).

The present invention further relates to a method for replacing an original refrigerant or heat transfer fluid composition, said original composition being R134a (HFC-134a, 1,1,1,2-tetrafluoroethane, $CF_3CH_2F$) in refrigeration apparatus, air-conditioning apparatus, or heat pump apparatus, wherein said method comprises substituting R134a with a second refrigerant or heat transfer fluid composition comprising at least one compound selected from the group consisting of trifluoromethyl trifluorovinyl ether (PMVE).

The present invention further relates to a method for replacing an original refrigerant or heat transfer fluid composition, said original composition being R152a (HFC-152a, 1,1-difluoroethane, $CHF_2CH_3$) in refrigeration apparatus, air-conditioning apparatus, or heat pump apparatus, wherein said method comprises substituting R152a with a second refrigerant or heat transfer fluid composition comprising at least one compound selected from the group consisting of E-1,3,3,3-tetrafluoropropene (E-HFC-1234ze), 1,2,3,3,3-pentafluoropropene (HFC-1225ye), 2,3,3,3-tetrafluoropropene (HFC-1234yf), 3,3,3-trifluoropropene (HFC-1243zf), and trifluoromethyl trifluorovinyl ether (PMVE).

The present invention further relates to a method for replacing R227ea (HFC-227ea, 1,1,1,2,3,3,3-heptafluoropropane, $CF_3CHFCF_3$) in refrigeration apparatus, air-conditioning apparatus, or heat pump apparatus, wherein said method comprises providing as a substitute a composition comprising at least one compound selected from the group consisting of E-1,3,3,3-tetrafluoropropene (E-HFC-1234ze), 1,2,3,3,3-pentafluoropropene (HFC-1225ye), 2,3,3,3-tetrafluoropropene (HFC-1234yf), 3,3,3-trifluoropropene (HFC-1243zf), and trifluoromethyl trifluorovinyl ether (PMVE).

The present invention further relates to a method for replacing an original refrigerant or heat transfer fluid composition, said original composition being R113 (CFC-113, 1,1,2-trichloro-1,2,2-trifluoroethane, $CFCl_2CF_2Cl$) in refrigeration apparatus, air-conditioning apparatus, or heat pump apparatus, wherein said method comprises substituting a second refrigerant or heat transfer fluid composition comprising at least one compound selected from the group consisting of 1,1,1,3,4,5,5,5-octafluoro-4-(trifluoromethyl)-2-butene (HFC-152-11 mmyyz); 1,1,1,4,4,5,5,5-octafluoro-2-(trifluoromethyl)-2-pentene (HFC-152-11 mmtz); 1,1,1,2,2,3,4,5,5,6,6,6-dodecafluoro-3-hexene (HFC-151-12mcy); 1,1,1,3-tetrafluoro-2-butene (HFC-1354mzy); 1,1,1,4,4,4-hexafluoro-2,3-bis(trifluoromethyl)-2-butene (HFC-151-12 mmtt); 1,2,3,3,4,4,5,5,6,6-decafluorocyclohexene (FC-C151-10y); 3,3,4,4,5,5,5-heptafluoro-2-methyl-1-pentene (HFC-1567 fts); 3,3,4,4,5,5,6,6,6-nonafluoro-1-hexene (PFBE); 4,4,5,5,6,6,6-heptafluoro-2-hexene (HFC-1567szz); 1,1,1,4,4,5,5,6,6,6-decafluoro-2-hexene (F13E); 1,1,1,2,3,4,5,5,5-nonafluoro-4-(trifluoromethyl)-2-pentene (HFC-151-12 mmzz); and 1,1,1,2,2,5,5,6,6,6-decafluoro-3-hexene (F22E).

The present invention further relates to a method for replacing an original refrigerant or heat transfer fluid composition, said original composition being R43-10mee (HFC-43-10mee), 1,1,1,2,3,4,4,5,5,5-decafluoropentane, $CF_3CHFCHFCF_2CF_3$) in refrigeration apparatus, air-conditioning apparatus, or heat pump apparatus, wherein said method comprises substituting a second refrigerant or heat transfer fluid composition comprising at least one compound selected from the group consisting of 1,1,1,3,4,5,5,5-octafluoro-4-(trifluoromethyl)-2-butene (HFC-152-11 mmyyz); 1,1,1,4,4,5,5,5-octafluoro-2-(trifluoromethyl)-2-pentene (HFC-152-11 mmtz); 1,1,1,2,2,3,4,5,5,6,6,6-dodecafluoro-3-hexene (HFC-151-12mcy); 1,1,1,3-tetrafluoro-2-butene (HFC-1354mzy); 1,1,1,4,4,4-hexafluoro-2,3-bis(trifluoromethyl)-2-butene (HFC-151-12 mmtt); 1,2,3,3,4,4,5,5,6,6-decafluorocyclohexene (FC-C151-10y); 3,3,4,4,5,5,5-heptafluoro-2-methyl-1-pentene (HFC-1567 fts); 3,3,4,4,5,5,6,6,6-nonafluoro-1-hexene (PFBE); 4,4,5,5,6,6,6-heptafluoro-2-hexene (HFC-1567szz); 1,1,1,4,4,5,5,6,6,6-decafluoro-2-hexene (F13E); 1,1,1,2,3,4,5,5,5-nonafluoro-4-(trifluoromethyl)-2-pentene (HFC-151-12 mmzz); and 1,1,1,2,2,5,5,6,6,6-decafluoro-3-hexene (F22E).

The present invention further relates to a method for replacing an original refrigerant or heat transfer fluid composition, said original composition being $C_4F_9OCH_3$ (perfluorobutyl methyl ether) in refrigeration apparatus, air-conditioning apparatus, or heat pump apparatus, wherein said method comprises substituting a second refrigerant or heat transfer fluid composition comprising at least one compound selected from the group consisting of 1,1,1,3,4,5,5,5-octafluoro-4-(trifluoromethyl)-2-butene (HFC-152-11 mmyyz); 1,1,1,4,4,5,5,5-octafluoro-2-(trifluoromethyl)-2-pentene (HFC-152-11 mmtz); 1,1,1,2,2,3,4,5,5,6,6,6-dodecafluoro-3-hexene (HFC-151-12mcy); 1,1,1,3-tetrafluoro-2-butene (HFC-1354mzy); 1,1,1,4,4,4-hexafluoro-2,3-bis(trifluoromethyl)-2-butene (HFC-151-12 mmtt); 1,2,3,3,4,4,5,5,6,6-decafluorocyclohexene (FC-C151-10y); 3,3,4,4,5,5,5-heptafluoro-2-methyl-1-pentene (HFC-1567 fts); 3,3,4,4,5,5,6,6,6-nonafluoro-1-hexene (PFBE); 4,4,5,5,6,6,6-heptafluoro-2-hexene (HFC-1567szz); 1,1,1,4,4,5,5,6,6,6-decafluoro-2-hexene (F13E); 1,1,1,2,3,4,5,5,5-nonafluoro-4-(trifluoromethyl)-2-pentene (HFC-151-12 mmzz); and 1,1,1,2,2,5,5,6,6,6-decafluoro-3-hexene (F22E).

The present invention further relates to a method for replacing an original refrigerant or heat transfer fluid composition, said original composition being R365mfc (HFC-365mfc, 1,1,1,3,3-pentafluorobutane, $CF_3CH_2CF_2CH_3$) in refrigeration apparatus, air-conditioning apparatus, or heat pump apparatus, wherein said method comprises substituting a second refrigerant or heat transfer fluid composition comprising at least one compound selected from the group consisting of 1,1,1,3,4,5,5,5-octafluoro-4-(trifluoromethyl)-2-butene (HFC-152-11 mmyyz); 1,1,1,4,4,5,5,5-octafluoro-2-(trifluoromethyl)-2-pentene (HFC-152-11 mmtz); 1,1,1,2,2,3,4,5,5,6,6,6-dodecafluoro-3-hexene (HFC-151-12mcy); 1,1,1,3-tetrafluoro-2-butene (HFC-1354mzy); 1,1,1,4,4,4-hexafluoro-2,3-bis(trifluoromethyl)-2-butene (HFC-151-12 mmtt); 1,2,3,3,4,4,5,5,6,6-decafluorocyclohexene (FC-C151-10y); 3,3,4,4,5,5,5-heptafluoro-2-methyl-1-pentene (HFC-1567 fts); 3,3,4,4,5,5,6,6,6-nonafluoro-1-hexene (PFBE); 4,4,5,5,6,6,6-heptafluoro-2-hexene (HFC-1567szz); 1,1,1,4,4,5,5,6,6,6-decafluoro-2-hexene (F13E); 1,1,1,2,3,4,5,5,5-nonafluoro-4-(trifluoromethyl)-2-pentene (HFC-151-12 mmzz); and 1,1,1,2,2,5,5,6,6,6-decafluoro-3-hexene (F22E).

The present invention further relates to a method for replacing an original refrigerant or heat transfer fluid composition, said original composition being R11 (CFC-11, trichlorofluoromethane, $CFCl_3$) in refrigeration apparatus, air-conditioning apparatus, or heat pump apparatus, wherein said method comprises substituting a second refrigerant or heat transfer fluid composition comprising at least one compound selected from the group consisting of 1,2,3,3,4,4,5,5-octafluorocyclopentene (FC-C1418y); 1,1,1,2,3,4,4,5,5,5-decafluoro-2-pentene (FC-141-10myy); 1,1,1,2,4,4,5,5,5-nonafluoro-2-pentene (HFC-1429myz); 1,1,1,3,4,4,5,5,5-nonafluoro-2-pentene (HFC-1429mzy); 3,3,4,4,5,5,5-heptafluoro-1-pentene (HFC-1447fz); 1,1,1,4,4,4-hexafluoro-2-butene (F11E); 1,1,1,4,4,4-hexafluoro-2-(trifluoromethyl)-2-butene (HFC-1429mzt); and 1,1,1,4,4,5,5,5-octafluoro-2-pentene (F12E).

The present invention further relates to a method for replacing an original refrigerant or heat transfer fluid composition, said original composition being R123 (HCFC-123, 2,2-dichloro-1,1,1-trifluoroethane, $CF_3CHCl_2$) in refrigeration apparatus, air-conditioning apparatus, or heat pump apparatus, wherein said method comprises substituting a second refrigerant or heat transfer fluid composition comprising at least one compound selected from the group consisting of 1,2,3,3,4,4,5,5-octafluorocyclopentene (FC-C1418y); 1,1,1,2,3,4,4,5,5,5-decafluoro-2-pentene (FC-141-10myy); 1,1,1,2,4,4,5,5,5-nonafluoro-2-pentene (HFC-1429myz); 1,1,1,3,4,4,5,5,5-nonafluoro-2-pentene (HFC-1429mzy); 3,3,4,4,5,5,5-heptafluoro-1-pentene (HFC-1447fz); 1,1,1,4,4,4-hexafluoro-2-butene (F11E); 1,1,1,4,4,4-hexafluoro-2-(trifluoromethyl)-2-butene (HFC-1429mzt); and 1,1,1,4,4,5,5,5-octafluoro-2-pentene (F12E).

The present invention further relates to a method for replacing an original refrigerant or heat transfer fluid composition, said original composition being R245fa (HFC-245fa, 1,1,1,3,3-pentafluoropropane, $CF_3CH_2CHF_2$) in refrigeration apparatus, air-conditioning apparatus, or heat pump apparatus, wherein said method comprises substituting a second refrigerant or heat transfer fluid composition comprising at least one compound selected from the group consisting of 2,3,3-trifluoropropene (HFC-1243yf); 1,1,1,4,4,4-hexafluoro-2-butene (F11 E); 1,3,3,3-tetrafluoropropene (HFC-1234ze); 1,1,1,2,4,4,4-heptafluoro-2-butene (HFC-1327my); 1,2,3,3-tetrafluoropropene (HFC-1234ye); and pentafluoroethyl trifluorovinyl ether (PEVE).

The present invention further relates to a method for replacing an original refrigerant or heat transfer fluid composition, said original composition being R114 (CFC-114, 1,2-dichloro-1,1,2,2-tetrafluoroethane, $CFCl_2CF_2Cl$) in refrigeration apparatus, air-conditioning apparatus, or heat pump apparatus, wherein said method comprises substituting a second refrigerant or heat transfer fluid composition comprising at least one compound selected from the group consisting of 1,1,1,2,3,4,4,4-octafluoro-2-butene (FC-1318my); 1,2,3,3,4,4-hexafluorocyclobutene (FC-C1316 cc); 2,3,3,4,4,4-hexafluoro-1-butene (HFC-1336yf); and 3,3,4,4,4-pentafluoro-1-butene (HFC-1345fz).

The present invention further relates to a method for replacing an original refrigerant or heat transfer fluid composition, said original composition being R236fa (HFC-236fa, 1,1,1,3,3,3-hexafluoropropane, $CF_3CH_2CF_3$) in refrigeration apparatus, air-conditioning apparatus, or heat pump apparatus, wherein said method comprises substituting a second refrigerant or heat transfer fluid composition comprising at least one compound selected from the group consisting of 1,1,1,2,3,4,4,4-octafluoro-2-butene (FC-1318my); 1,2,3,3,4,4-hexafluorocyclobutene (FC-C1316 cc); 2,3,3,4,4,4-hexafluoro-1-butene (HFC-1336yf); and 3,3,4,4,4-pentafluoro-1-butene (HFC-1345fz).

The present invention relates to a method for replacing an original refrigerant or heat transfer fluid composition, said original composition being R401A in refrigeration apparatus, air-conditioning apparatus, or heat pump apparatus, wherein said method comprises substituting a second refrigerant or heat transfer fluid composition comprising at least one compound selected from the group consisting of E-1,3,3,3-tetrafluoropropene (E-HFC-1234ze); 1,2,3,3,3-pentafluoropropene (HFC-1225ye); 2,3,3,3-tetrafluoropropene (HFC-1234yf); 3,3,3-trifluoropropene (HFC-1243zf); and trifluoromethyl trifluorovinyl ether (PMVE). R401A is the ASHRAE designation for a refrigerant blend containing about 53 weight percent HCFC-22 (chlorodifluoromethane, $CHF_2Cl$), about 13 weight percent HFC-152a (1,1-difluoroethane, $CHF_2CH_3$), and about 34 weight percent HCFC-124 (2-chloro-1,1,1,2-tetrafluoroethane, $CF_3CHClF$).

The present invention further relates to a method for replacing an original refrigerant or heat transfer fluid composition, said original composition being R401B in refrigeration apparatus, air-conditioning apparatus, or heat pump apparatus, wherein said method comprises substituting a second refrigerant or heat transfer fluid composition comprising at least one compound selected from the group consisting of E-1,3,3,3-tetrafluoropropene (E-HFC-1234ze); 1,2,3,3,3-pentafluoropropene (HFC-1225ye); 2,3,3,3-tetrafluoropropene (HFC-1234yf); 3,3,3-trifluoropropene (HFC-1243zf); and trifluoromethyl trifluorovinyl ether (PMVE). R401B is the ASHRAE designation for a refrigerant blend containing about 61 weight percent HCFC-22 (chlorodifluoromethane, $CHF_2Cl$), about 11 weight percent HFC-152a (1,1-difluoroethane, $CHF_2CH_3$), and about 28 weight percent HCFC-124 (2-chloro-1,1,1,2-tetrafluoroethane, $CF_3CHClF$).

The present invention further relates to a method for replacing an original refrigerant or heat transfer fluid composition, said original composition being R409A in refrigeration apparatus, air-conditioning apparatus, or heat pump apparatus, wherein said method comprises substituting a second refrigerant or heat transfer fluid composition comprising at least one compound selected from the group consisting of E-1,3,3,3-tetrafluoropropene (E-HFC-1234ze); 1,2,3,3,3-pentafluoropropene (HFC-1225ye); 2,3,3,3-tetrafluoropropene (HFC-1234yf); 3,3,3-trifluoropropene (HFC-1243zf); and trifluoromethyl trifluorovinyl ether (PMVE). R409A is the ASHRAE designation for a refrigerant blend containing about 60 weight percent HCFC-22 (chlorodifluoromethane, $CHF_2Cl$), about 25 weight percent HCFC-124 (2-chloro-1,1,1,2-tetrafluoroethane, $CF_3CHClF$), and about 15 weight percent HCFC-142b (1-chloro-1,1-difluoroethane, $CF_2ClCH_3$).

The present invention further relates to a method for replacing an original refrigerant or heat transfer fluid composition, said original composition being R409B in refrigeration apparatus, air-conditioning apparatus, or heat pump apparatus, wherein said method comprises substituting a second refrigerant or heat transfer fluid composition comprising at least one compound selected from the group consisting of E-1,3,3,3-tetrafluoropropene (E-HFC-1234ze); 1,2,3,3,3-pentafluoropropene (HFC-1225ye); 2,3,3,3-tetrafluoropropene (HFC-1234yf); 3,3,3-trifluoropropene (HFC-1243zf); and trifluoromethyl trifluorovinyl ether (PMVE). R409B is the ASHRAE designation for a refrigerant blend containing about 65 weight percent HCFC-22 (chlorodifluoromethane, $CHF_2Cl$), about 25 weight percent HCFC-124 (2-chloro-1,1,1,2-tetrafluoroethane, $CF_3CHClF$), and about 10 weight percent HCFC-142b (1-chloro-1,1-difluoroethane, $CF_2ClCH_3$).

The present invention further relates to a method for replacing an original refrigerant or heat transfer fluid composition, said original composition being R414B in refrigeration apparatus, air-conditioning apparatus, or heat pump apparatus, wherein said method comprises substituting a second refrigerant or heat transfer fluid composition comprising at least one compound selected from the group consisting of E-1,3,3,3-tetrafluoropropene (E-HFC-1234ze), 1,2,3,3,3-pentafluoropropene (HFC-1225ye), 2,3,3,3-tetrafluoropropene (HFC-1234yf), 3,3,3-trifluoropropene (HFC-1243zf), and trifluoromethyl trifluorovinyl ether (PMVE). R414B is the ASHRAE designation for a refrigerant blend containing about 50 weight percent HCFC-22 (chlorodifluoromethane, $CHF_2Cl$), about 39 weight percent HCFC-124 (2-chloro-1,1,1,2-tetrafluoroethane, $CF_3CHClF$), about 1.5 weight percent isobutane (R600a, $CH_3CH(CH_3)CH_3$) and about 9.5 weight percent HCFC-142b (1-chloro-1,1-difluoroethane, $CF_2ClCH_3$).

The present invention further relates to a method for replacing an original refrigerant or heat transfer fluid composition, said original composition being R416A in refrigeration apparatus, air-conditioning apparatus, or heat pump apparatus, wherein said method comprises substituting a second refrigerant or heat transfer fluid composition comprising at least one compound selected from the group consisting of E-1,3,3,3-tetrafluoropropene (E-HFC-1234ze); 1,2,3,3,3-pentafluoropropene (HFC-1225ye); 2,3,3,3-tetrafluoropropene (HFC-1234yf); 3,3,3-trifluoropropene (HFC-1243zf); and trifluoromethyl trifluorovinyl ether (PMVE). R416A is the ASHRAE designation for a refrigerant blend containing about 59 weight percent HFC-134a (1,1,1,2-tetrafluoroethane, $CF_3CH_2F$)), about 39.5 weight percent HCFC-124 (2-chloro-1,1,1,2-tetrafluoroethane, $CF_3CHClF$), and about 1.5 weight percent n-butane ($CH_3CH_2CH_2CH_3$).

The present invention further relates to a method for replacing an original refrigerant or heat transfer fluid composition, said original composition being R12 (CFC-12, dichlorodifluoromethane, $CF_2Cl_2$) in refrigeration apparatus, air-conditioning apparatus, or heat pump apparatus, wherein said method comprises substituting a second refrigerant or heat transfer fluid composition comprising at least one compound selected from the group consisting of 1,2,3,3,3-pentafluoropropene (HFC-1225ye); 2,3,3,3-tetrafluoropropene (HFC-1234yf); 3,3,3-trifluoropropene (HFC-1243zf); and trifluoromethyl trifluorovinyl ether (PMVE).

The present invention further relates to a method for replacing an original refrigerant or heat transfer fluid composition, said original composition being R500 in refrigeration apparatus, air-conditioning apparatus, or heat pump apparatus, wherein said method comprises substituting a second refrigerant or heat transfer fluid composition comprising at least one compound selected from the group consisting of 1,2,3,3,3-pentafluoropropene (HFC-1225ye); 2,3,3,3-tetrafluoropropene (HFC-1234yf); 3,3,3-trifluoropropene (HFC-1243zf); and trifluoromethyl trifluorovinyl ether (PMVE). R500 is the ASHRAE designation for an azeotropic refrigerant blend containing about 73.8 weight percent R12 ((CFC-12, dichlorodifluoromethane, $CF_2Cl_2$) and about 26.2 weight percent R152a (HFC-152a, 1,1-difluoroethane, $CHF_2CH_3$).

The present invention relates to a method for replacing an original refrigerant or heat transfer fluid composition wherein the original refrigerant or heat transfer fluid composition is R134a or R12 and wherein said R134a or R12 is substituted by a second refrigerant or heat transfer fluid composition comprising about 1.0 weight percent to about 37 weight percent HFC-32 and about 99 weight percent to about 63 weight percent HFC-1225ye. In another embodiment, the second refrigerant or heat transfer fluid composition may comprise about 1.0 weight percent to about 10 weight percent HFC-32 and about 99 weight percent to about 90 weight percent HFC-1225ye.

The present invention relates to a method for replacing an original refrigerant or heat transfer fluid composition wherein the original refrigerant or heat transfer fluid composition R22, R404A, or R410A and wherein said R22, R404A or R410A is substituted by a second refrigerant or heat transfer fluid composition comprising about 1.0 weight percent to about 37 weight percent HFC-32 and about 99 weight percent to about 63 weight percent HFC-1225ye. In another embodiment, the second refrigerant or heat transfer fluid composition may comprise about 20 weight percent to about 37 weight percent HFC-32 and about 80 weight percent to about 63 weight percent HFC-1225ye.

The present invention further relates to a method for replacing an original refrigerant or heat transfer fluid composition wherein the original refrigerant or heat transfer fluid composition is R22, R404A, or R410A and wherein said R22, R404A or R410A is substituted by a second refrigerant or heat transfer fluid composition comprising about 20 weight percent to about 95 weight percent HFC-1225ye, about 1.0 weight percent to about 65 weight percent HFC-32, and about 1.0 weight percent to about 40 weight percent HFC-125. In another embodiment, the second refrigerant or heat transfer fluid composition comprises about 30 weight percent to about 90 weight percent HFC-1225ye, about 5.0 weight percent to about 55 weight percent HFC-32, and about 1.0 weight percent to about 35 weight percent HFC-125. In yet another embodiment, the second refrigerant or heat transfer fluid composition comprises about 40 weight percent to about 85 weight percent HFC-1225ye, about 10 weight percent to about 45 weight percent HFC-32 and about 1.0 weight percent to about 28 weight percent HFC-125.

The present invention relates to a method for replacing an original refrigerant or heat transfer fluid composition wherein the original refrigerant or heat transfer fluid composition is R134a or R12 and wherein said R134a or R12 is substituted by a second refrigerant or heat transfer fluid composition comprising:

HFC-1243zf and HFC-1225ye;
HFC-1243zf, HFC-1225ye, and HFC-125;
HFC-1243zf, HFC-1225ye, and HFC-32; or
HFC-1243zf, HFC-1225ye, HFC-125, and HFC-32.

In all the previously described methods for replacing refrigerants, the fluoroolefins may be used to replace refrigerant in existing equipment. Additionally, the fluoroolefins may be used to replace refrigerant in existing equipment designed for use of said refrigerant. Additionally, the fluoroolefins may be used to replace refrigerant in existing equipment without the need to change or replace the lubricant.

The present invention relates to a method for reducing the fire hazard in refrigeration apparatus, air-conditioning apparatus, or heat pump apparatus, said method comprising introducing a composition of the present invention into said refrigerant apparatus or air-conditioning apparatus.

Refrigerant that may leak from a refrigeration apparatus, air-conditioning apparatus, or heat pump apparatus, is a major concern when considering flammability. Should a leak occur in a refrigeration apparatus or air-conditioning apparatus, refrigerant and potentially a small amount of lubricant may be released from the system. If this leaking material comes in contact with an ignition source, a fire may result. By fire hazard is meant the probability that a fire may occur either within or in the vicinity of a refrigeration apparatus, air-conditioning apparatus, or heat pump apparatus. Reducing the fire hazard in a refrigeration apparatus, air-conditioning apparatus, or heat pump apparatus may be accomplished by using a refrigerant or heat transfer fluid that is not considered flammable as determined and defined by the methods and standards described previously herein. Additionally, the non-flammable fluoroolefins of the present invention may be added to a flammable refrigerant or heat transfer fluid, either in the apparatus already or prior to adding to the apparatus.

The non-flammable fluoroolefins of the present invention reduce the probability of a fire in the event of a leak and/or reduce the degree of fire hazard by reducing the temperature or size of any flame produced.

The present invention further relates to a method for reducing fire hazard in or in the vicinity of a refrigeration apparatus, air-conditioning apparatus, or heat pump apparatus, said method comprising combining at least one non-flammable fluoroolefin with a flammable refrigerant and introducing the combination into a refrigeration apparatus, air-conditioning apparatus, or heat pump apparatus.

The present invention further relates to a method for reducing fire hazard in or in the vicinity of a refrigeration apparatus, air-conditioning apparatus, or heat pump apparatus, said method comprising combining at least one non-flammable fluoroolefin with a lubricant and introducing the combination into the refrigeration apparatus, air-conditioning apparatus, or heat pump apparatus comprising flammable refrigerant.

The present invention further relates to a method for reducing fire hazard in or in the vicinity of a refrigeration apparatus, air-conditioning apparatus, or heat pump apparatus, said method comprising introducing at least one fluoroolefin into said apparatus.

The present invention further relates to a method of using a flammable refrigerant in refrigeration apparatus, air-conditioning apparatus, or heat pump apparatus, said method comprising combining said flammable refrigerant with at least one fluoroolefin.

The present invention further relates to a method for reducing flammability of a flammable refrigerant or heat transfer fluid, said method comprising combining the flammable refrigerant with at least one fluoroolefin.

The present invention further relates to a process for transfer of heat from a heat source to a heat sink wherein the compositions of the present invention serve as heat transfer fluids. Said process for heat transfer comprises transporting the compositions of the present invention from a heat source to a heat sink.

Heat transfer fluids are utilized to transfer, move or remove heat from one space, location, object or body to a different space, location, object or body by radiation, conduction, or convection. A heat transfer fluid may function as a secondary coolant by providing means of transfer for cooling (or heating) from a remote refrigeration (or heating) system. In some systems, the heat transfer fluid may remain in a constant state throughout the transfer process (i.e., not evaporate or condense). Alternatively, evaporative cooling processes may utilize heat transfer fluids as well.

A heat source may be defined as any space, location, object or body from which it is desirable to transfer, move or remove heat. Examples of heat sources may be spaces (open or enclosed) requiring refrigeration or cooling, such as refrigerator or freezer cases in a supermarket, building spaces requiring air-conditioning, or the passenger compartment of an automobile requiring air-conditioning. A heat sink may be defined as any space, location, object or body capable of absorbing heat. A vapor compression refrigeration system is one example of such a heat sink.

EXAMPLES

Example 1

Performance Data

Table 7 shows refrigeration performance, as pressure in the evaporator (Evap) and condenser (Cond), discharge temperature (Disch T), energy efficiency (COP), and capacity (Cap), for compounds of the present invention as compared to CFC-113, HFC-43-10mee, $C_4F_9OCH_3$, and HFC-365mfc. The data are based on the following conditions.

| | |
|---|---|
| Evaporator temperature | 40.0° F. (4.4° C.) |
| Condenser temperature | 110.0° F. (43.3° C.) |
| Subcool temperature | 10.0° F. (5.5° C.) |
| Return gas temperature | 75.0° F. (23.8° C.) |
| Compressor efficiency is | 70% |

TABLE 7

| Compound | Evap Pres (Psia) | Evap Pres (kPa) | Cond Pres (Psia) | Cond Pres (kPa) | Comp Disch T (F.) | Comp Disch T (C.) | COP | Cap (Btu/min) | Cap (kW) |
|---|---|---|---|---|---|---|---|---|---|
| CFC-113 | 2.7 | 18.6 | 12.8 | 88.3 | 156.3 | 69.1 | 4.18 | 14.8 | 0.26 |
| HFC-43-10mee | 2.0 | 13.4 | 10.4 | 71.9 | 132.8 | 56.0 | 3.94 | 12.2 | 0.21 |
| $C_4F_9OCH_3$ | 1.5 | 10.1 | 8.3 | 57.0 | 131.3 | 55.2 | 3.93 | 9.5 | 0.17 |
| HFC-365mfc | 3.6 | 25.1 | 16.3 | 112.1 | 146.3 | 63.5 | 4.11 | 21.4 | 0.38 |
| 1,1,1,3,4,5,5,5-octafluoro-4-(trifluoromethyl)-2-butene ((HFC-152-11mmyyz) | 2.1 | 14.4 | 10.7 | 71.9 | 127.1 | 52.8 | 3.83 | 12.3 | 0.24 |
| 1,1,1,4,4,5,5,5-octafluoro-2-(trifluoromethyl)-2-pentene (HFC-152-11mmtz) | 2.0 | 13.4 | 10.4 | 71.9 | 127.3 | 52.9 | 3.83 | 11.8 | 0.23 |
| 1,1,1,2,2,3,4,5,5,6,6,6-dodecafluoro-3-hexene (FC-151-12mcy) | 2.5 | 17.3 | 12.3 | 85.1 | 121.8 | 49.9 | 3.69 | 13.8 | 0.24 |
| 1,1,1,3-tetrafluoro-2-butene (HFC-1354mzy) | 2.5 | 17.4 | 11.6 | 80.1 | 162.0 | 72.2 | 4.25 | 15.9 | 0.28 |
| 1,1,1,4,4,4-hexafluoro-2,3-bis(trifluoromethyl)-2-butene (FC-151-12mmtt) | 2.0 | 13.5 | 10.0 | 69.2 | 122.7 | 50.4 | 3.73 | 11.2 | 0.20 |
| 1,2,3,3,4,4,5,5,6,6-decafluorocyclohexene (FC-C151-10y) | 2.1 | 14.4 | 10.6 | 72.9 | 126.7 | 52.6 | 3.84 | 12.3 | 0.22 |
| 3,3,4,4,5,5,5-heptafluoro-2-methyl-1-pentene (HFC-1567fts) | 2.0 | 14.1 | 9.9 | 68.5 | 130.0 | 54.4 | 3.92 | 12.0 | 0.21 |

TABLE 7-continued

| Compound | Evap Pres (Psia) | Evap Pres (kPa) | Cond Pres (Psia) | Cond Pres (kPa) | Comp Disch T (F.) | Comp Disch T (C.) | COP | Cap (Btu/min) | Cap (kW) |
|---|---|---|---|---|---|---|---|---|---|
| 3,3,4,4,5,5,6,6,6-nonafluoro-1-hexene (PFBE) | 1.6 | 11.0 | 8.6 | 59.4 | 130.7 | 54.8 | 3.92 | 10.0 | 0.18 |
| 4,4,5,5,6,6,6-heptafluoro-2-hexene (HFC-1567szz) | 1.3 | 9.2 | 7.4 | 51.3 | 137.8 | 58.8 | 4.04 | 8.9 | 0.16 |
| 1,1,1,4,4,5,5,6,6,6-decafluoro-2-hexene (F13E) | 2.0 | 13.7 | 10.7 | 73.8 | 131.1 | 55.1 | 3.90 | 12.4 | 0.22 |
| 1,1,1,2,3,4,5,5-nonafluoro-4-(trifluoromethyl)-2-pentene (FC-151-12mmzz) | 2.5 | 17.3 | 12.3 | 85.1 | 121.8 | 49.9 | 3.69 | 13.8 | 0.24 |
| 1,1,1,2,2,5,5,6,6,6-decafluoro-3-hexene (F22E) | 2.4 | 16.6 | 12.6 | 86.7 | 128.0 | 53.3 | 3.83 | 14.4 | 0.25 |

Example 2

Performance Data

Table 8 shows refrigeration performance, as pressure in the evaporator (Evap) and condenser (Cond), discharge temperature (Disch T), energy efficiency (COP), and capacity (Cap), for compounds of the present invention as compared to CFC-11 and HCFC-123. The data are based on the following conditions.

| Evaporator temperature | 40.0° F. (4.4° C.) |
|---|---|
| Condenser temperature | 110.0° F. (43.3° C.) |
| Subcool temperature | 10.0° F. (5.5° C.) |
| Return gas temperature | 75.0° F. (23.8° C.) |
| Compressor efficiency is | 70% |

TABLE 8

| Compound | Evap Pres (Psia) | Evap Pres (kPa) | Cond Pres (Psia) | Cond Pres (kPa) | Comp Disch T (F.) | Comp Disch T (C.) | COP | Cap (Btu/min) | Cap (kW) |
|---|---|---|---|---|---|---|---|---|---|
| CFC-11 | 7.1 | 49.0 | 28.0 | 192.8 | 190.5 | 88.1 | 4.29 | 41.1 | 0.72 |
| HCFC-123 | 5.8 | 40.3 | 25.0 | 172.4 | 174.2 | 79.0 | 4.25 | 35.2 | 0.62 |
| 1,2,3,3,4,4,5,5-octafluorocyclopentene (FC-C1418y) | 6.0 | 41.6 | 25.3 | 174.6 | 131.7 | 55.4 | 3.87 | 31.6 | 0.55 |
| 1,1,1,2,3,4,4,5,5-decafluoro-2-pentene (FC-141-10myy) | 7.5 | 51.8 | 30.0 | 206.6 | 124.9 | 51.6 | 3.66 | 35.3 | 0.62 |
| 1,1,1,2,4,4,5,5,5-nonafluoro-2-pentene (HFC-1429myz) | 5.5 | 37.9 | 23.7 | 163.1 | 132.0 | 55.6 | 3.85 | 29.0 | 0.51 |
| 1,1,1,3,4,4,5,5,5-nonafluoro-2-pentene (HFC-1429mzy) | 5.5 | 37.9 | 23.7 | 163.1 | 132.0 | 55.6 | 3.85 | 29.0 | 0.51 |
| 3,3,4,4,5,5,5-heptafluoro-1-pentene (HFC-1447fz) | 5.4 | 37.0 | 23.1 | 159.3 | 135.3 | 57.4 | 3.92 | 29.0 | 0.51 |
| 1,1,1,4,4,4-hexafluoro-2-butene (F11E) | 4.7 | 32.3 | 20.8 | 143.4 | 150.1 | 65.6 | 4.11 | 27.5 | 0.48 |
| 1,1,1,4,4,4-hexafluoro-2-(trifluoromethyl)-2-butene (HFC-1429mzt) | 4.8 | 33.0 | 21.0 | 144.9 | 132.6 | 55.9 | 3.88 | 25.9 | 0.45 |
| 1,1,1,4,4,5,5,5-octafluoro-2-pentene (F12E) | 5.5 | 37.9 | 24.4 | 168.0 | 137.0 | 58.3 | 3.93 | 30.6 | 0.54 |

Example 3

Performance Data

Table 9 shows refrigeration performance, as pressure in the evaporator (Evap) and condenser (Cond), discharge temperature (Disch T), energy efficiency (COP), and capacity (Cap), for compounds of the present invention as compared to HFC-245fa. The data are based on the following conditions.

| Evaporator temperature | 40.0° F. (4.4° C.) |
| --- | --- |
| Condenser temperature | 110.0° F. (43.3° C.) |
| Subcool temperature | 10.0° F. (5.5° C.) |
| Return gas temperature | 75.0° F. (23.8° C.) |
| Compressor efficiency is | 70% |

TABLE 9

| Compound | Evap Pres (Psia) | Evap Pres (kPa) | Cond Pres (Psia) | Cond Pres (kPa) | Comp Disch T (F.) | Comp Disch T (C.) | COP | Cap (Btu/min) | Cap (kW) |
| --- | --- | --- | --- | --- | --- | --- | --- | --- | --- |
| HFC-245fa | 10.0 | 68.8 | 38.9 | 268.5 | 156.7 | 69.3 | 4.10 | 53.3 | 0.93 |
| 2,3,3-trifluoropropene (HFC-1243yf) | 12.6 | 87.1 | 45.4 | 313.0 | 172.8 | 78.2 | 4.19 | 65.6 | 1.15 |
| 1,1,1,4,4,4-hexafluoro-2-butene (F11E) | 12.5 | 85.9 | 47.5 | 327.4 | 148.8 | 64.9 | 3.99 | 62.8 | 1.10 |
| 1,3,3,3-tetrafluoropropene (HFC-1234ze) | 12.1 | 83.4 | 45.8 | 315.6 | 178.8 | 81.6 | 4.19 | 65.6 | 1.15 |
| 1,1,1,2,4,4,4-heptafluoro-2-butene (HFC-1327my) | 10.5 | 72.5 | 39.9 | 275.0 | 142.3 | 61.3 | 3.94 | 52.0 | 0.91 |
| 1,2,3,3-tetrafluoropropene (HFC-1234ye) | 9.6 | 66.3 | 36.9 | 254.6 | 176.9 | 80.5 | 4.21 | 53.0 | 0.93 |
| pentafluoroethyl trifluorovinyl ether (PEVE) | 13.1 | 90.4 | 49.3 | 339.8 | 130.7 | 54.8 | 3.69 | 59.3 | 1.04 |

Example 4

Performance Data

Table 10 shows refrigeration performance, as pressure in the evaporator (Evap) and condenser (Cond), discharge temperature (Disch T), energy efficiency (COP), and capacity (Cap), for compounds of the present invention as compared to CFC-114 and HFC-236fa. The data are based on the following conditions.

| Evaporator temperature | 40.0° F. (4.4° C.) |
| --- | --- |
| Condenser temperature | 110.0° F. (43.3° C.) |
| Subcool temperature | 10.0° F. (5.5° C.) |
| Return gas temperature | 75.0° F. (23.8° C.) |
| Compressor efficiency is | 70% |

TABLE 10

| Compound | Evap Pres (Psia) | Evap Pres (kPa) | Cond Pres (Psia) | Cond Pres (kPa) | Comp Disch T (F.) | Comp Disch T (C.) | COP | Cap (Btu/min) | Cap (kW) |
| --- | --- | --- | --- | --- | --- | --- | --- | --- | --- |
| CFC-114 | 15.4 | 106.5 | 54.3 | 374.2 | 147.2 | 64.0 | 3.97 | 72.9 | 1.28 |
| HFC-236fa | 18.2 | 125.8 | 64.2 | 442.6 | 142.8 | 61.6 | 3.86 | 82.9 | 1.45 |
| 1,1,1,2,3,4,4,4-octafluoro-2-butene (FC-1318my) | 17.2 | 118.8 | 59.1 | 407.4 | 131.8 | 55.4 | 3.68 | 72.1 | 1.26 |
| 1,2,3,3,4,4-hexafluorocyclobutene (FC-C1316cc) | 16.5 | 113.5 | 58.8 | 405.4 | 141.1 | 60.6 | 3.90 | 76.6 | 1.34 |
| 2,3,3,4,4,4-hexafluoro-1-butene (HFC-1336yf) | 14.2 | 98.2 | 50.2 | 346.3 | 139.4 | 59.7 | 3.88 | 65.3 | 1.14 |
| 3,3,4,4,4-pentafluoro-1-butene (HFC-1345fz) | 14.8 | 101.8 | 53.5 | 368.5 | 145.5 | 63.1 | 3.95 | 70.7 | 1.24 |

Example 5

Performance Data

Table 11 shows refrigeration performance, as pressure in the evaporator (Evap) and condenser (Cond), discharge temperature (Disch T), energy efficiency (COP), and capacity (Cap), for compounds of the present invention as compared to HFC-134a, HFC-152a, and HFC-227ea. The data are based on the following conditions.

| | |
|---|---|
| Evaporator temperature | 40.0° F. (4.4° C.) |
| Condenser temperature | 110.0° F. (43.3° C.) |
| Subcool temperature | 10.0° F. (5.5° C.) |
| Return gas temperature | 75.0° F. (23.8° C.) |
| Compressor efficiency is | 70% |

TABLE 11

| Compound | Evap Pres (Psia) | Evap Pres (kPa) | Cond Pres (Psia) | Cond Pres (kPa) | Comp Disch T (F.) | Comp Disch T (C.) | COP | Cap (Btu/min) | Cap (kW) |
|---|---|---|---|---|---|---|---|---|---|
| HFC-134a | 49.6 | 341.6 | 161.2 | 1111.4 | 168.9 | 76.1 | 3.86 | 213.3 | 3.73 |
| HFC-152a | 46.2 | 318.8 | 146.5 | 1009.9 | 200.1 | 93.4 | 4.02 | 209.4 | 3.67 |
| HFC-227ea | 32.3 | 222.7 | 105.5 | 727.4 | 142.9 | 61.6 | 3.67 | 129.3 | 2.26 |
| 2,3,3,3-tetrafluoropropene (HFC-1234yf) | 47.4 | 326.7 | 139.6 | 962.2 | 154.8 | 68.2 | 3.79 | 180.5 | 3.16 |
| 3,3,3-trifluoropropene (HFC-1243zf) | 39.0 | 268.8 | 122.0 | 841.0 | 166.2 | 74.6 | 3.95 | 166.3 | 2.91 |
| 1,2,3,3,3-pentafluoropropene (HFC-1225ye) | 36.1 | 248.9 | 112.9 | 778.4 | 157.8 | 69.9 | 3.86 | 148.9 | 2.61 |
| E-1,3,3,3-tetrafluoropropene (E-HFC-1234ze) | 35.5 | 245.0 | 115.1 | 793.9 | 162.4 | 72.4 | 3.90 | 153.8 | 2.69 |
| trifluoromethyl trifluorovinyl ether (PMVE) | 39.3 | 271.1 | 124.0 | 855.2 | 140.9 | 60.5 | 3.57 | 147.6 | 2.58 |

Example 6

Flammability

Flammable compounds may be identified by testing under ASTM (American Society of Testing and Materials) E681-01, with an electronic ignition source. Such tests of flammability were conducted on compositions of the present disclosure at 101 kPa (14.7 psia), 50 percent relative humidity, and the temperature indicated, at various concentrations in air in order to determine if flammable and if so, find the lower flammability limit (LFL). The results are given in Table 12.

TABLE 12

| Composition | Temperature (° C.) | LFL (vol % in air) |
|---|---|---|
| HFC-1225ye | 100 | Non-flammable |
| HFC-1234yf | 100 | 5.0 |
| E-HFC-1234ze | 100 | 6.0 |
| HFC-1429myz/mzy | 23 | Non-flammable |
| F12E | 23 | Non-flammable |
| HFC-1225ye/HFC-32 (65/35 wt %) | 60 | Non-flammable |
| HFC-1225ye/HFC-32 (63/37 wt %) | 60 | Non-flammable |
| HFC-1225ye/HFC-32 (62/38 wt %) | 60 | 13.0 |
| HFC-1225ye/HFC-32 (60/40 wt %) | 60 | 13.0 |

The results indicate that HFC-1234yf and E-HFC-1234ze are flammable, while HFC-1225ye, HFC-1429myz/mzy, and F12E are non-flammable. For mixtures of HFC-1225ye and HFC-32 (which is known to be flammable in the pure state) it has been determined that 37 weight percent HFC-32 is the highest amount that can be present to maintain the non-flammable characteristic. Those compositions comprising fluoroolefins that are non-flammable are more acceptable candidates as refrigerant or heat transfer fluid compositions.

Example 7

Tip Speed to Develop Pressure

Tip speed can be estimated by making some fundamental relationships for refrigeration equipment that use centrifugal compressors. The torque an impeller ideally imparts to a gas is defined as $$T = m^*(v_2^* r_2 - v_1^* r_1) \quad \text{Equation 1}$$

where
T=torque, Newton-meters
m=mass rate of flow, kg/sec
$v_2$=tangential velocity of refrigerant leaving impeller (tip speed), meters/sec
$r_2$=radius of exit impeller, meters
$v_1$=tangential velocity of refrigerant entering impeller, meters/sec
$r_1$=radius of inlet of impeller, meters Assuming the refrigerant enters the impeller in an essentially axial direction, the tangential component of the velocity $v_1$=0, therefore $$T = m^* v_2^* r_2 \quad \text{Equation 2}$$

The power required at the shaft is the product of the torque and the rotative speed $$P = T^* \omega \quad \text{Equation 3}$$

where
P=power, W
ω=angular velocity, radians/s
therefore, $$P = T^* w = m^* v_2^* r_2^* \omega \quad \text{Equation 4}$$

At low refrigerant flow rates, the tip speed of the impeller and the tangential velocity of the refrigerant are nearly identical; therefore $$r_2*\omega = v_2 \quad \text{Equation 5}$$

and $$P = m*v_2*v_2 \quad \text{Equation 6}$$

Another expression for ideal power is the product of the mass rate of flow and the isentropic work of compression, $$P = m*H_i*(1000J/kJ) \quad \text{Equation 7}$$

where $H_i$=Difference in enthalpy of the refrigerant from a saturated vapor at the evaporating conditions to saturated condensing conditions, kJ/kg.

Combining the two expressions Equation 6 and 7 produces, $$v_2*v_2 = 1000*H_i \quad \text{Equation 8}$$

Although Equation 8 is based on some fundamental assumptions, it provides a good estimate of the tip speed of the impeller and provides an important way to compare tip speeds of refrigerants.

Table 13 below shows theoretical tip speeds that are calculated for 1,2,2-trichlorotrifluoroethane (CFC-113) and compositions of the present invention. The conditions assumed for this comparison are:

| Evaporator temperature | 40.0° F. (4.4° C.) |
| Condenser temperature | 110.0° F. (43.3° C.) |
| Liquid subcool temperature | 10.0° F. (5.5° C.) |
| Return gas temperature | 75.0° F. (23.8° C.) |
| Compressor efficiency is | 70% |

These are typical conditions under which small turbine centrifugal compressors perform.

TABLE 13

| Compound | Hi Btu/lb | Hi*0.7 Btu/lb | Hi*0.7 KJ/Kg | Tip speed (V2) m/s | Tip speed relative to CFC-113 |
|---|---|---|---|---|---|
| CFC-113 | 10.92 | 7.6 | 17.8 | 133.3 | n/a |
| HFC-152-11mmyyz | 11.56 | 8.1 | 18.8 | 137.2 | 103% |
| FC-151-12mcy | 11.86 | 8.3 | 19.3 | 139.0 | 104% |
| HFC-1354mzy | 13.96 | 9.8 | 22.7 | 150.8 | 113% |
| FC-151-12mmtt | 11.93 | 8.4 | 19.4 | 139.4 | 105% |
| FC-C151-10y | 12.48 | 8.7 | 20.3 | 142.5 | 107% |
| HFC-1567fm | 14.21 | 9.9 | 23.1 | 152.1 | 114% |
| PFBE | 12.8 | 9.0 | 20.8 | 144.4 | 108% |
| HFC-1567szz | 13.42 | 9.4 | 21.9 | 147.8 | 111% |
| HFC-1438mzz | 11.73 | 8.2 | 19.1 | 138.2 | 104% |
| FC-151-12mmzz | 11.86 | 8.3 | 19.3 | 139.0 | 104% |
| HFC-153-10mczz | 12.23 | 8.6 | 19.9 | 141.1 | 106% |

The example shows that compounds of the present invention have tip speeds within about 15 percent of CFC-113 and would be effective replacements for CFC-113 with minimal compressor design changes. Most preferred compositions have tip speeds within about 10 percent of CFC-113.

Example 8

Refrigeration Performance Data

Table 14 shows the performance of various refrigerant compositions of the present invention as compared to HFC-134a. In Table 14, Evap Pres is evaporator pressure, Cond Pres is condenser pressure, Comp Disch T is compressor discharge temperature, COP is energy efficiency, and CAP is capacity. The data are based on the following conditions.

| Evaporator temperature | 40.0° F. (4.4° C.) |
| Condenser temperature | 130.0° F. (54.4° C.) |
| Subcool amount | 10.0° F. (5.5° C.) |
| Return gas temperature | 60.0° F. (15.6° C.) |
| Compressor efficiency is | 100% |

Note that the superheat is included in cooling capacity.

TABLE 14

| Composition (wt %) | Evap Pres (Psia) | Evap Pres (kPa) | Cond Pres (Psia) | Cond Pres (kPa) | Comp Disch T (F.) | Comp Disch T (C.) | Cap (Btu/min) | Cap (kW) | COP |
|---|---|---|---|---|---|---|---|---|---|
| HFC-134a | 50.3 | 346 | 214 | 1476 | 156 | 68.9 | 213 | 3.73 | 4.41 |
| HFC-1225ye | 37.6 | 259 | 165 | 1138 | 146 | 63.3 | 162 | 2.84 | 4.41 |
| HFC-1225ye/HFC-152a (85/15) | 39.8 | 274 | 173 | 1193 | 151 | 66.1 | 173 | 3.03 | 4.45 |
| HFC-1225ye/HFC-32 (97/3) | 43.1 | 297 | 184 | 1269 | 149 | 65.0 | 186 | 3.26 | 4.50 |
| HFC-1225ye/HFC-32 (96/4) | 44.2 | 305 | 189 | 1303 | 150 | 65.6 | 191 | 3.35 | 4.51 |
| HFC-1225ye/HFC-32 (95/5) | 46.5 | 321 | 197 | 1358 | 151 | 66.1 | 200 | 3.50 | 4.53 |
| HFC-1225ye/HFC-32 (94/6) | 47.3 | 326 | 200 | 1379 | 153 | 67.2 | 203 | 3.56 | 4.52 |
| HFC-1225ye/HFC-32 (93/7) | 48.8 | 336 | 205 | 1413 | 154 | 67.8 | 210 | 3.68 | 4.53 |
| HFC-1225ye/HFC-32 (90/10) | 53.0 | 365 | 222 | 1531 | 157 | 69.4 | 227 | 3.98 | 4.52 |
| HFC-1243zf/HFC-1225ye (40/60) | 40.8 | 281 | 172 | 1186 | 148 | 64.4 | 170 | 2.97 | 4.39 |
| HFC-1243zf/HFC-1225ye (50/50) | 41.8 | 288 | 174 | 1200 | 149 | 65.0 | 172 | 3.02 | 4.37 |
| HFC-1243zf/HFC-1225ye (60/40) | 42.9 | 296 | 177 | 1220 | 149 | 65.0 | 175 | 3.07 | 4.36 |
| HFC-1243zf/HFC-1225ye (70/30) | 44.1 | 304 | 180 | 1241 | 150 | 65.6 | 178 | 3.12 | 4.35 |
| HFC-1243zf/HFC-1225ye/HFC-125 (40/56/4) | 42.7 | 294 | 179 | 1234 | 148 | 64.4 | 176 | 3.09 | 4.38 |
| HFC-1243zf/HFC-1225ye/HFC-125 (50/46/4) | 43.7 | 301 | 181 | 1248 | 149 | 65.0 | 179 | 3.13 | 4.37 |
| HFC-1243zf/HFC-1225ye/HFC-125 (60/36/4) | 44.8 | 309 | 184 | 1269 | 149 | 65.0 | 182 | 3.18 | 4.36 |

TABLE 14-continued

| Composition (wt %) | Evap Pres (Psia) | Evap Pres (kPa) | Cond Pres (Psia) | Cond Pres (kPa) | Comp Disch T (F.) | Comp Disch T (C.) | Cap (Btu/min) | Cap (kW) | COP |
|---|---|---|---|---|---|---|---|---|---|
| HFC-1243zf/HFC-1225ye/HFC-125 (70/26/4) | 49.9 | 344 | 201 | 1386 | 153 | 67.2 | 202 | 3.54 | 4.40 |
| HFC-1243zf/HFC-1225ye/HFC-32 (40/55/5) | 48.4 | 334 | 199 | 1372 | 153 | 67.2 | 202 | 3.54 | 4.47 |
| HFC-1243zf/HFC-1225ye/HFC-32 (42/55/3) | 45.6 | 314 | 189 | 1303 | 151 | 66.1 | 190 | 3.33 | 4.44 |
| HFC-1243zf/HFC-1225ye/HFC-32 (60/35/5) | 50.3 | 347 | 203 | 1400 | 154 | 67.8 | 206 | 3.60 | 4.43 |
| HFC-1243zf/HFC-1225ye/HFC-32 (62/35/3) | 47.7 | 329 | 194 | 1338 | 152 | 66.7 | 195 | 3.41 | 4.41 |
| HFC-1243zf/HFC-1225ye/HFC-125/HFC-32 (40/55/4/1) | 44.2 | 305 | 184 | 1269 | 149 | 65.0 | 183 | 3.21 | 4.41 |
| HFC-1243zf/HFC-1225ye/HFC-125/HFC-32 (40/55/3/2) | 45.3 | 312 | 188 | 1296 | 150 | 65.6 | 188 | 3.29 | 4.42 |
| HFC-1243zf/HFC-1225ye/HFC-125/HFC-32 (60/35/4/1) | 46.3 | 319 | 189 | 1303 | 150 | 65.6 | 188 | 3.29 | 4.37 |
| HFC-1243zf/HFC-1225ye/HFC-125/HFC-32 (60/35/3/2) | 47.3 | 326 | 193 | 1331 | 151 | 66.1 | 192 | 3.37 | 4.39 |

Several compositions have even higher energy efficiency (COP) than HFC-134a while maintaining lower or equivalent discharge pressures and temperatures. Capacity for the compositions listed in Table 14 is also similar to R134a indicating these compositions could be replacement refrigerants for R134a in refrigeration and air-conditioning, and in mobile air-conditioning applications in particular. Results also show cooling capacity of HFC-1225ye can be improved with addition of other compounds such as HFC-32.

Example 9

Refrigeration Performance Data

Table 15 shows the performance of various refrigerant compositions of the present invention as compared to R404A and R422A. In Table 15, Evap Pres is evaporator pressure, Cond Pres is condenser pressure, Comp Disch T is compressor discharge temperature, EER is energy efficiency, and CAP is capacity. The data are based on the following conditions.

| Evaporator temperature | −17.8° C. |
|---|---|
| Condenser temperature | 46.1° C. |
| Subcool amount | 5.5° C. |
| Return gas temperature | 15.6° C. |
| Compressor efficiency is | 70% |

Note that the superheat is included in cooling capacity.

TABLE 15

| | wt % | Evap Press (kPa)) | Cond P Press (kPa) | Compr Disch T (C.) | CAP (kJ/m3) | EER |
|---|---|---|---|---|---|---|
| Existing Refrigerant Product | | | | | | |
| R22 | | 267 | 1774 | 144 | 1697 | 4.99 |
| R404A | | 330 | 2103 | 101.1 | 1769 | 4.64 |
| R507A | | 342 | 2151 | 100.3 | 1801 | 4.61 |
| R422A | | 324 | 2124 | 95.0 | 1699 | 4.54 |
| Candidate Replacement | | | | | | |
| HFC-32/HFC-1225ye | 20/80 | 200 | 1620 | 117 | 1331 | 4.91 |
| HFC-32/HFC-1225ye | 30/70 | 246 | 1879 | 126 | 1587 | 4.85 |
| HFC-32/HFC-1225ye | 40/60 | 284 | 2101 | 134 | 1788 | 4.74 |
| HFC-32/HFC-1225ye | 35/65 | 256 | 1948 | 130.5 | 1652 | 4.85 |
| HFC-32/HFC-1225ye | 37/63 | 264 | 1991 | 132.2 | 1694 | 4.81 |
| HFC-32/HFC-125/HFC-1225ye | 10/10/'80 | 173 | 1435 | 107.0 | 1159 | 4.97 |
| HFC-32/HFC-125/HFC-1225ye | 15/5.5/79.5 | 184 | 1509 | 111.9 | 1235 | 4.97 |
| HFC-32/HFC-125/HFC-1225ye | 24/13.7/62.3 | 242 | 1851 | 119.7 | 1544 | 4.85 |
| HFC-32/HFC-125/HFC-1225ye | 25/25/50 | 276 | 2041 | 120.0 | 1689 | 4.73 |
| HFC-32/HFC-125/HFC-1225ye | 25/40/35 | 314 | 2217 | 119.0 | 1840 | 4.66 |
| HFC-32/HFC-125/HFC-1225ye | 27.5/17.5/55 | 264 | 1980 | 122.8 | 1653 | 4.78 |
| HFC-32/HFC-125/HFC-1225ye | 30/10/60 | 265 | 1990 | 125.0 | 1664 | 4.78 |

TABLE 15-continued

| | wt % | Evap Press (kPa) | Cond P Press (kPa) | Compr Disch T (C.) | CAP (kJ/m3) | EER |
|---|---|---|---|---|---|---|
| HFC-32/HFC-125/HFC-1225ye | 30/15/55 | 276 | 2046 | 125.0 | 1710 | 4.76 |
| HFC-32/HFC-125/HFC-1225ye | 30/19/51 | 278 | 2056 | 124.8 | 1724 | 4.75 |
| HFC-32/HFC-125/HFC-1225ye | 30/20/50 | 287 | 2102 | 124.0 | 1757 | 4.73 |
| HFC-32/HFC-125/HFC-1225ye | 30/30/40 | 311 | 2218 | 124.0 | 1855 | 4.68 |
| HFC-32/HFC-125/HFC-1225ye | 30/35/35 | 324 | 2271 | 123.0 | 1906 | 4.66 |
| HFC-32/HFC-125/HFC-1225ye | 31/20/49 | 285 | 2090 | 125.5 | 1756 | 4.74 |
| HFC-32/HFC-125/HFC-1225ye | 33/22/45 | 298 | 2157 | 127.0 | 1820 | 4.72 |
| HFC-32/HFC-125/HFC-1225ye | 35/15/50 | 296 | 2157 | 129.0 | 1820 | 4.72 |
| HFC-32/HFC-125/HFC-1225ye | 35/20/45 | 308 | 2212 | 129.0 | 1868 | 4.70 |
| HFC-32/HFC-125/HFC-1225ye | 35/30/35 | 332 | 2321 | 127.0 | 1968 | 4.66 |
| HFC-32/HFC-125/HFC-1225ye | 35/40/25 | 357 | 2424 | 126.0 | 2068 | 4.64 |
| HFC-32/HFC-125/HFC-1225ye | 50/30/20 | 390 | 2584 | 138.0 | 2277 | 4.54 |
| HFC-32/HFC-125/HFC-1225ye | 40/30/30 | 353 | 2418 | 131.0 | 2077 | 4.66 |
| HFC-32/HFC-125/HFC-1225ye | 40/35/25 | 364 | 2465 | 131.0 | 2124 | 4.64 |
| HFC-32/HFC-125/HFC-1225ye | 45/30/25 | 372 | 2505 | 135.0 | 2180 | 4.66 |

Several compositions have energy efficiency (EER) comparable top R404A and R422A. Discharge temperatures are also lower than R404A and R507A. Capacity for the compositions listed in Table 15 is also similar to R404A, R507A, and R422A indicating these compositions could be replacement refrigerants for R404A, R507A, or R422A in refrigeration and air-conditioning.

Example 10

Refrigeration Performance Data

Table 16 shows the performance of various refrigerant compositions of the present invention as compared to HCFC-22 and R410A. In Table 16, Evap Pres is evaporator pressure, Cond Pres is condenser pressure, Comp Disch T is compressor discharge temperature, EER is energy efficiency, and CAP is capacity. The data are based on the following conditions.

| Evaporator temperature | 4° C. |
|---|---|
| Condenser temperature | 43° C. |
| Subcool amount | 6° C. |
| Return gas temperature | 18° C. |
| Compressor efficiency is | 70% |

Note that the superheat is included in cooling capacity.

TABLE 16

| | Evap Press (kPa) | Cond Press (kPa) | Compr Disch Temp (C.) | CAP (kJ/m3) | EER |
|---|---|---|---|---|---|
| Existing refrigerant product | | | | | |
| R22 | 565 | 1648 | 90.9 | 3808 | 9.97 |
| R410A | 900 | 2571 | 88.1 | 5488 | 9.27 |
| Candidate replacement product (Composition wt %) | | | | | |
| HFC-32/HFC-1225ye (40/60) | 630 | 1948 | 86.7 | 4242 | 9.56 |
| HFC-32/HFC-1225ye (45/55) | 666 | 2041 | 88.9 | 4445 | 9.49 |
| HFC-32/HFC-1225ye (50/50) | 701 | 2127 | 91.0 | 4640 | 9.45 |
| HFC-32/HFC-1225ye (30/70) | 536 | 1700 | 82.1 | 3729 | 9.73 |
| HFC-32/HFC-1225ye (35/65) | 575 | 1805 | 84.5 | 3956 | 9.66 |
| HFC-32/HFC-1225ye (37/63) | 590 | 1845 | 85.5 | 4043 | 9.64 |
| HFC-32/HFC-125/HFC-1225ye (60/5/35) | 784 | 2323 | 94.6 | 5087 | 9.42 |
| HFC-32/HFC-125/HFC-1225ye (60/10/30) | 803 | 2365 | 94.2 | 5173 | 9.42 |
| HFC-32/HFC-125/HFC-1225ye (60/15/25) | 822 | 2407 | 93.9 | 5256 | 9.39 |
| HFC-32/HFC-125/HFC-1225ye (50/10/40) | 742 | 2220 | 90.3 | 4820 | 9.42 |
| HFC-32/HFC-125/HFC-1225ye (50/5/45) | 721 | 2173 | 90.7 | 4730 | 9.45 |
| HFC-32/HFC-125/HFC-1225ye (50/15/35) | 762 | 2266 | 90.0 | 4911 | 9.42 |
| HFC-32/HFC-125/HFC-1225ye (40/15/45) | 692 | 2097 | 85.9 | 4518 | 9.45 |
| HFC-32/HFC-125/HFC-1225ye (40/10/50) | 671 | 2047 | 86.2 | 4425 | 9.49 |
| HFC-32/HFC-125/HFC-1225ye (35/15/50) | 654 | 2001 | 83.8 | 4304 | 9.49 |
| HFC-32/HFC-125/HFC-1225ye (37.5/11.5/51) | 643 | 1976 | 85.2 | 4287 | 9.54 |

TABLE 16-continued

|  | Evap Press (kPa) | Cond Press (kPa) | Compr Disch Temp (C.) | CAP (kJ/m3) | EER |
|---|---|---|---|---|---|
| HFC-32/HFC-125/HFC-1225ye (34/6/60) | 593 | 1848 | 83.8 | 4028 | 9.62 |
| HFC-32/HFC-125/HFC-1225ye (30/3/67) | 548 | 1732 | 82.0 | 3788 | 9.70 |
| HFC-32/HFC-125/HFC-1225ye (30/12.7/57.3) | 590 | 1837 | 81.7 | 3980 | 9.60 |
| HFC-32/HFC-125/HFC-1225ye (24/13.7/62.3) | 544 | 1715 | 78.7 | 3713 | 9.66 |
| HFC-32/HFC-125/HFC-1225ye (20/5/75) | 471 | 1522 | 76.9 | 3329 | 9.82 |
| HFC-32/HFC-125/HFC-1225ye (15/5.5/79.5) | 427 | 1398 | 74.1 | 3061 | 9.89 |

Compositions have energy efficiency (EER) comparable to R22 and R410A while maintaining reasonable discharge temperatures. Capacity for certain compositions listed in Table 16 is also similar to R22 indicating these compositions could be replacement refrigerants for R22 in refrigeration and air-conditioning. Additionally, there are compositions listed in Table 16 with capacity approaching or equivalent to that for R410A indicating that those compositions could be replacement refrigerants for R410A in refrigeration and air-conditioning.

Example 11

Refrigeration Performance Data

Table 17 shows the performance of various refrigerant compositions of the present invention as compared to HCFC-22, R410A, R407C, and R417A. In Table 17, Evap Pres is evaporator pressure, Cond Pres is condenser pressure, Comp Disch T is compressor discharge temperature, EER is energy efficiency, and CAP is capacity. The data are based on the following conditions.

| | |
|---|---|
| Evaporator temperature | 4.4° C. |
| Condenser temperature | 54.4° C. |
| Subcool amount | 5.5° C. |
| Return gas temperature | 15.6° C. |
| Compressor efficiency is | 100% |

Note that the superheat is included in cooling capacity.

TABLE 17

|  | wt % | Evap Press (kPa)) | Cond Press (kPa) | Compr Disch T (C.) | CAP (kJ/m$^3$) | EER |
|---|---|---|---|---|---|---|
| Existing Refrigerant Product | | | | | | |
| R22 | | 573 | 2149 | 88.6 | 3494 | 14.73 |
| R410A | | 911 | 3343 | 89.1 | 4787 | 13.07 |
| R407C | | 567 | 2309 | 80.0 | 3397 | 14.06 |
| R417A | | 494 | 1979 | 67.8 | 2768 | 13.78 |
| Candidate Replacement | | | | | | |
| HFC-32/HFC-125/HFC-1225ye | 30/40/30 | 732 | 2823 | 81.1 | 3937 | 13.20 |
| HFC-32/HFC-125/HFC-1225ye | 23/25/52 | 598 | 2429 | 78.0 | 3409 | 13.54 |

Compositions have energy efficiency (EER) comparable to R22, R407C, R417A, and R410A while maintaining low discharge temperatures. Capacity for the compositions listed in Table 17 is also similar to R22, R407C and R417A indicating these compositions could be replacement refrigerants for R22, R407C or R417A in refrigeration and air-conditioning.

What is claimed is:

1. A process for cooling in a refrigeration, air-conditioning or heat pump apparatus suitable for using CFC-11 or HCFC-123 as a refrigerant, said process comprising:
    condensing a composition comprising a refrigerant consisting essentially of 1,1,1,4,4,5,5,5-octafluoro-2-pentene; and thereafter
    evaporating said composition in the vicinity of a body to be cooled, wherein said condensing and evaporating takes place in a chiller.

2. The process of claim 1, wherein prior to said condensing, said composition comprising a refrigerant consisting essentially of 1,1,1,4,4,5,5,5-octafluoro-2-pentene is compressed in a compressor selected from the group consisting of centrifugal compressors, screw compressors, and scroll compressors.

3. A process to produce cooling in a refrigeration, air-conditioning or heat pump apparatus suitable for using CFC-11 or HCFC-123 as a refrigerant, comprising compressing a composition comprising a refrigerant consisting essentially of 1,1,1,4,4,5,5,5-octafluoro-2-pentene, in a centrifugal compressor, condensing said composition, and thereafter evaporating said composition in the vicinity of a body to be cooled.

4. The process of claim 3 wherein said centrifugal compressor comprises a multistage centrifugal compressor.

5. The process of claim 4, wherein said multistage centrifugal compressor comprises a 2 stage centrifugal compressor.

6. A process to produce cooling in a refrigeration, air-conditioning or heat pump apparatus suitable for using CFC-11 or HCFC-123 as a refrigerant, said process comprising:
    condensing a composition comprising a refrigerant consisting essentially of 1,1,1,4,4,5,5,5-octafluoro-2-pentene; and thereafter
    evaporating said composition in the vicinity of a body to be cooled, wherein said condensing and evaporating take place in a heat exchanger selected from the group consisting of fin and tube heat exchangers, microchannel heat exchangers, vertical or horizontal single pass tube or plate type heat exchangers, and single slab/single pass heat exchangers.

7. A method for replacing an original refrigerant or heat transfer fluid composition with a second refrigerant or heat transfer fluid composition said method comprising:
provuding a composition comprising a refrigerant consisting essentially of 1,1,1,4,4,5,5,5-octafluoro-2-pentene as the second refrigerant or heat transfer fluid composition, wherein said original refrigerant or heat transfer fluid composition comprises a refrigerant consisting essentially of CFC-11 or HCFC-123.

8. The method of claim 7, wherein said second refrigerant or heat transfer fluid composition further comprises a stabilizer.

9. The method of claim 7, wherein said original refrigerant or heat transfer fluid composition comprises HCFC-123.

10. The process of claim 1, 3, or 6, wherein said composition further comprises a stabilizer.

11. The process of claim 1, 3, or 6, further comprising replacing a composition comprising a refrigerant consisting essentially of CFC-11 or HCFC-123 with said composition comprising a refrigerant consisting essentially of 1,1,1,4,4,5,5,5-octafluoro-2-pentene.

* * * * *